United States Patent
Donnelly et al.

(10) Patent No.: US 10,994,033 B2
(45) Date of Patent: May 4, 2021

(54) IMAGING METHODS USING 18F-RADIOLABELED BIOLOGICS

(71) Applicant: BRISTOL-MYERS SQUIBB COMPANY, Princeton, NJ (US)

(72) Inventors: David Donnelly, Doylestown, PA (US); David K. Leung, West Windsor, NJ (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 0 days.

(21) Appl. No.: 16/305,286

(22) PCT Filed: May 31, 2017

(86) PCT No.: PCT/US2017/035271
§ 371 (c)(1),
(2) Date: Nov. 28, 2018

(87) PCT Pub. No.: WO2017/210335
PCT Pub. Date: Dec. 7, 2017

(65) Prior Publication Data
US 2019/0184043 A1 Jun. 20, 2019

Related U.S. Application Data

(60) Provisional application No. 62/344,289, filed on Jun. 1, 2016.

(51) Int. Cl.
*A61K 51/08* (2006.01)
*A61K 49/00* (2006.01)
*C07K 16/28* (2006.01)

(52) U.S. Cl.
CPC ........ *A61K 51/088* (2013.01); *A61K 49/0004* (2013.01); *C07K 16/2818* (2013.01)

(58) Field of Classification Search
CPC .............. A61K 49/0004; A61K 51/088; C07K 16/2818
See application file for complete search history.

(56) References Cited

U.S. PATENT DOCUMENTS

| 6,989,452 B2 | 1/2006 | Ng et al. |
| 7,087,600 B2 | 8/2006 | Ng et al. |
| (Continued) | | |

FOREIGN PATENT DOCUMENTS

| WO | 02/096910 A1 | 12/2002 |
| WO | 07/038658 A2 | 4/2007 |
| (Continued) | | |

OTHER PUBLICATIONS

Abstracts "DEGRO 2016", Strahlentherapie Und Onkologie, vol. 192(1): 1-161 (2016), XP035803487, ISSN: 0179-7158, DOI:10.1007/S00066-016-0974-Z [retrieved on May 11, 2016].

(Continued)

*Primary Examiner* — Marcus H Taningco
(74) *Attorney, Agent, or Firm* — Nelson Mullins Riley & Scarborough LLP; Jane E. Remillard, Esq.; Cynthia L. Kanik

(57) ABSTRACT

The invention relates to water soluble $^{18}$F-prosthetic groups and the synthesis and use $^{18}$F-labeled biological molecules containing the $^{18}$F-prosthetic groups for imaging various processes within the body, for detecting the location of molecules associated with disease pathology, and for monitoring disease progression are disclosed.

21 Claims, 7 Drawing Sheets

Specification includes a Sequence Listing.

```
1   GVSDV PRDLE VVAAT PTSLL ISWRA QLSPS FYYRI TYGET
41  GGNSP VQEFT VPNDV MTATI SGLKP GVDYT ITVYA VTTHG
81  VYFYS PISIN YRTPC
```

(56) References Cited

U.S. PATENT DOCUMENTS

| | | | |
|---|---|---|---|
| 7,129,261 | B2 | 10/2006 | Ng et al. |
| 7,556,925 | B2 | 7/2009 | Koide et al. |
| 7,943,743 | B2 | 5/2011 | Korman et al. |
| 8,008,449 | B2 | 8/2011 | Korman et al. |
| 8,221,765 | B2 | 7/2012 | Camphausen et al. |
| 8,324,362 | B2 | 12/2012 | Chen et al. |
| 8,343,501 | B2 | 1/2013 | Emanuel et al. |
| 8,470,332 | B2 | 6/2013 | Camphausen et al. |
| 8,524,244 | B2 | 9/2013 | Camphausen et al. |
| 8,609,613 | B2 | 12/2013 | Chen et al. |
| 8,728,483 | B2 | 5/2014 | Camphausen et al. |
| 8,808,665 | B2 | 8/2014 | McBride et al. |
| 8,853,154 | B2 | 10/2014 | Cload et al. |
| 8,933,199 | B2 | 1/2015 | Cload et al. |
| 8,969,289 | B2 | 3/2015 | Gosselin et al. |
| 8,993,265 | B2 | 3/2015 | Cload et al. |
| 9,017,655 | B2 | 4/2015 | Emanuel et al. |
| 9,234,028 | B2 | 1/2016 | Camphausen et al. |
| 9,328,157 | B2 | 5/2016 | Chen et al. |
| 9,469,676 | B2 | 10/2016 | Camphausen et al. |
| 9,493,546 | B2 | 11/2016 | Cload et al. |
| 9,522,951 | B2 | 12/2016 | Davis et al. |
| 9,540,424 | B2 | 1/2017 | Gosselin et al. |
| 9,562,089 | B2 | 2/2017 | Camphausen et al. |
| 9,605,039 | B2 | 3/2017 | Lipovsek et al. |
| 9,662,373 | B2 | 5/2017 | Cload et al. |
| 9,771,411 | B2 | 9/2017 | Emanuel et al. |
| 9,862,758 | B2 | 1/2018 | Chen et al. |
| 9,902,762 | B2 | 2/2018 | Camphausen et al. |
| 9,920,108 | B2 | 3/2018 | Camphausen et al. |
| 10,406,251 | B2 | 9/2019 | Morin et al. |
| 2006/0004081 | A1 | 1/2006 | Chen et al. |
| 2006/0024317 | A1 | 2/2006 | Boyd et al. |
| 2006/0246059 | A1 | 11/2006 | Lipovsek et al. |
| 2006/0247295 | A1 | 11/2006 | Gangwar et al. |
| 2009/0208410 | A1* | 8/2009 | Berndorff .......... A61K 51/1018 424/1.49 |
| 2012/0309250 | A1 | 12/2012 | Velev et al. |
| 2013/0309250 | A1 | 11/2013 | Cogswell et al. |
| 2013/0310317 | A1 | 11/2013 | Camphausen et al. |
| 2013/0323249 | A1 | 12/2013 | Zhou et al. |
| 2014/0271467 | A1 | 9/2014 | Hackel et al. |
| 2015/0252097 | A1 | 9/2015 | Camphausen et al. |
| 2015/0361159 | A1 | 12/2015 | Lipovsek et al. |
| 2015/0368319 | A1 | 12/2015 | Yamniuk et al. |
| 2016/0287734 | A1* | 10/2016 | Rashidian .......... A61K 51/1096 |
| 2016/0376346 | A1 | 12/2016 | Camphausen et al. |
| 2017/0088602 | A1 | 3/2017 | Cload et al. |
| 2017/0114042 | A1* | 4/2017 | Koike ................. C07D 401/14 |
| 2017/0137494 | A1 | 5/2017 | Davis et al. |
| 2017/0145464 | A1 | 5/2017 | Gosselin et al. |
| 2017/0166627 | A1 | 6/2017 | Camphausen et al. |
| 2017/0174748 | A1 | 6/2017 | Mitchell et al. |
| 2017/0183393 | A1 | 6/2017 | Lipovsek |
| 2017/0190761 | A1 | 7/2017 | Camphausen et al. |
| 2017/0258948 | A1 | 9/2017 | Morin et al. |
| 2017/0275342 | A1 | 9/2017 | Lipovsek et al. |
| 2017/0354718 | A1 | 12/2017 | Cload et al. |
| 2018/0037631 | A1 | 2/2018 | Emanuel et al. |
| 2018/0326098 | A1 | 11/2018 | Donnelly |
| 2019/0015532 | A1* | 1/2019 | Kjaer ................. A61K 38/4846 |
| 2019/0184042 | A1 | 6/2019 | Morin et al. |
| 2019/0184043 | A1 | 6/2019 | Donnelly et al. |
| 2019/0343972 | A1 | 11/2019 | Morin et al. |

FOREIGN PATENT DOCUMENTS

| | | |
|---|---|---|
| WO | 07/059404 A2 | 5/2007 |
| WO | 2007/051081 A1 | 5/2007 |
| WO | 08/083312 A2 | 7/2008 |
| WO | 08/103693 A2 | 8/2008 |
| WO | 2013/010573 A1 | 1/2013 |
| WO | 2013/173223 A1 | 11/2013 |
| WO | 2014/086364 A1 | 6/2014 |
| WO | 2014/126902 A1 | 8/2014 |
| WO | 2015/143199 A1 | 9/2015 |
| WO | 2016/022994 A2 | 2/2016 |
| WO | 2016/077518 A1 | 5/2016 |
| WO | 2016/086021 A1 | 6/2016 |
| WO | 2016/086036 A2 | 6/2016 |
| WO | 2016/162368 A1 | 10/2016 |
| WO | 2017/053617 A1 | 3/2017 |
| WO | 2017/053619 A1 | 3/2017 |
| WO | 2017/072273 A1 | 5/2017 |
| WO | 2017/072280 A1 | 5/2017 |
| WO | 2017/210302 A1 | 12/2017 |
| WO | 2017/210335 A1 | 12/2017 |

OTHER PUBLICATIONS

Berndt, M. et al., "Labeling of low-density lipoproteins using the 18F-labeled thiol-reactive reagent N-[6-(4-[18F] fluorobenzylidene)aminooxyhexyl]maleimide," Nuclear Medicine and Biology, vol. 34:5-15 (2007).

Campbell-Verduyn, L.S. et al., "Strain-Promoted Copper-Free "Click" Chemistry for 18F Radiolabeling of Bombesin," Angewandte Chemie International Edition, vol. 50 (47):11117-11120 (2011)XP55250606.

Chatterjee, S. et al., "A humanized antibody for imaging immune checkpoint ligand PD-L1 expression in tumors," Oncotarget, vol. 7(9):10215-10227 (2016), XP055389519, Retrieved from the Internet: URL:http://www.impactjournals.com/oncotarget/index.php? Journal=oncotarget&page=article&op=download&path □ =7143 &path □ =20347[retrieved on Jul. 7, 2017].

Chatterjee, S. et al., "Rapid PD-L1 detection in tumors with PET using a highly specific peptide," Biochemical and Biophysical Research Communications, vol. 483(1):258-263, (2016) XP029887248.

Donnelly, D. et al., "Discovery of a novel 18F prosthetic group that enables radiolabeling of anti-human PD-L1 Adnectins," The Journal of Nuclear Medicine: Annual Meeting of the Society of Nuclear Medicine and Molecular Imaging, vol. 58, No. Suppl. 1 p. 68 (2017) XP008185772, Society of Nuclear Medicine, US, Denver, Colorado, ISSN: 0161-5505, Retrieved from the Internet: URL:http://jnm.snmjournals.org/content/58/supplement 1/68 [retrieved on Aug. 24, 2017].

Gill, H.S., et al., "Preparation of 18F-labeled peptides using the copper(I)-catalyzed azide-alkyne 1,3-dipolar cycloaddition.," Nature Protocols, vol. 6:1718-1719 (2011).

Hackel, B. et al., "Use of 64Cu-labeled Fibronectin Domain with EGFR-Overexpressing Tumor Xenograft: Molecular Imaging", Radiology, vol. 263(1):179-188 (2012) XP055255254.

Heskamp S. et al., "SPECT/CT imaging of tumor PD-L1 expression using radiolabeled anti-PD-L1 antibodies," (Abstract 116), Journal of Nuclear Medicine, vol. 56 (Suppl 3) 1 page (May 2015)XP002773040, & Annual Meeting of the Society of Nuclear Medicine-and Molecular Imaging, Jun. 6-10, 2015 Retrieved from the Internet: URL:http://jnm.snmjournals.org/content/56/supplement 3/116.short [retrieved on Aug. 18, 2017].

Heskamp, S. et al., "Noninvasive Imaging of Tumor PD-L1 Expression Using Radiolabeled Anti-PD-L1 Antibodies," Cancer Research, vol. 75 (14):2928-2936 (2015) XP055255277.

Inkster, J. et al., "2-Fluoropyridine prosthetic compounds for the 18F labeling of bombesin analogues," Bioorganic & Medicinal Chemistry Letters, vol. 23:3920-3926 (2013).

International Preliminary Report on Patentability, PCT/US2017/035271, dated Dec. 4, 2018, 10 pages.

International Search Report and Written Opinion, PCT/US2017/035271, dated Sep. 11, 2017, 16 pages.

Josefsson, A. et al., "Imaging, Biodistribution, and Dosimetry of Radionuclide-Labeled PD-L1 Antibody in an Immunocompetent Mouse Model of Breast Cancer," Cancer Research, vol. 76 (2):472-479 (2016) XP055398622, ISSN: 0008-5472, DOI: 10.1158/0008-5472 [retrieved on May 11, 2016].

Koide S. et al., "Target-binding proteins based on the 10th human fibronectin type III domain(10Fn3)," Methods in Enzymology, Academ. Press, USA, vol. 503: 135-156 (2012).

Kuhnast, B. et al., "PEG-[18F]FPyKYNE, a fluoropyridine-based alkyne reagent designed for the fluorine-18 labelling of macromol-

(56) References Cited

OTHER PUBLICATIONS ecules using click chemistry," Journal of Labelled Compounds and Radiopharmaceuticals, vol. 51 (9):336-342 (2008) XP55250465.

Kuhnast, B. et al., "PEG-[18F]FPyZIDE and PEG-[18F]FPyKYNE, Two New Fluoropyridine-Based Reagents for the Fluorine-18 Labeling of Macromolecules Using Click Chemistry," Journal of Labelled Compounds and Radiopharmaceuticals, p. S184, Jun. 17, 2009, XP055250504.

Lesniak, W. et al., "PD-L1 Detection in Tumors Using [64Cu]Atezolizumab with PET," Bioconjugate Chemistry, vol. 27(9):2103-2110 (2016).

Maute R. et al., "Engineering high-affinity PD-1 variants for optimized immunotherapy and immuno-PET imaging," PNAS, vol. 112 (47):E6506-E6514 (2015) XP002772779, ISSN: 0027-8424.

Maxwell, B. et al.,"The synthesis of a carbon-14 labeled pegylated Adnectin(TM) for placental transfer studies in guinea pigs," Journal of Labellled Compounds and Radiopharmaceuticals, vol. 56(9-10):492-494 (2013) XP055255267.

McCabe, K. et al., "Positive progress in immunoPET—not just a coincidence," Cancer Biotherapy and Radiopharmacueticals, vol. 25(3):253-261 (2010) XP009150571.

Natarajan, A. et al., "A Novel Engineered Anti-CD20 Tracer Enables Early Time PET Imaging in a Humanized Transgenic Mouse Model of B-cell Non-Hodgkins Lymphoma," Clinical Cancer Research, vol. 19 (24):6820-6829 (2013), XP055398629, ISSN: 1078-0432, DOI:10.1158/1078-0432.CCR-13/0626.

Niemeijer, Anna-Larissa N. et al: "Whole body PD-1 and PD-L1 PET with 89Zr-nivolumab and 18F-BMS-986192 in pts with NSCLC," Journal of Clinical Oncology, Abstract Only, May 2017, XP002773215, Retrieved from the Internet: <URL:http://ascopubs.org/author/Poot%2C+Alex+J> [retrieved on Aug. 24, 2017].

Patterson, C. et al., "Development of a New Positron Emission Tomography Tracer for Targeting Tumor Angiogenesis: Synthesis, Small Animal Imaging, and Radiation Dosimetry," Molecules, vol. 18(5):5594-5610 (2013) XP055255261.

Price, E. et al., "Matching chelators to radiometals for radiopharmaceuticals," Chem Soc Rev., vol. 43:260-290 (2014).

Proceedings of the World Molecular Imaging Congress 2015, Honolulu, Hawaii, Sep. 2-5, 2015, "Late-Breaking Abstracts," Molecular Imaging & Biology, vol. 18(1):51554-51859 (2016) XP035974151, ISSN: 1536-1632, DOI:10.1007/S11307-016-0968-3 [retrieved on May 24, 2016].

Sachin, K et al., "F-18 Labeling Protocol of Peptides Based on Chemically Orthogonal Strain-Promoted Cycloaddition under Physiologically Friendly Reaction Conditions," Bioconjugate Chemistry, vol. 23 (8):1680-1686 (2012) XP55043362.

Salsano, M. et al., "PET imaging using radiolabeled antibodies: future direction in tumor diagnosis and correlate applications," Research and Reports in Nuclear Medicine,vol. 3:9-17(2013) XP055255276.

Schrama, D. et al., "Antibody targeted drugs as cancer therapeutics," Nature Rev. Drug Disc., vol. 5: 147-159 (2006).

Valdivia, A. et al., "A fast, simple, and reproducible automated synthesis of [18F]FPyKYNE-c(RGDyK) for alpha v beta 3 receptor positron emission tomography imaging," Journal of Labelled Compounds and Radiopharmaceuticals, vol. 55(2):57-60 (2011) XP55250449.

Wang H. et al.,"Development of a Carbon-14 Labeling Approach to Support Disposition Studies with a Pegylated Biologic," Drug Metabolism and Disposition, vol. 40(9):1677-1685 (2012)XP055255270.

Yampolsky, L. et al., "The Exchangeability of Amino Acids in Proteins," Genetics, vol. 170: 1459-1472 (2005).

Chow, P. "Radiosynthesis and Preclinical PET Evaluation of 89Zr-Nivolumab (BMS-936558) in Healthy Non-Human Primates," Proceedings of the World Molecular Imaging Congress 2015, Honolulu, Hawaii, Sep. 2-5, 2015: Late-Breaking Abstracts Molecular Imaging and Biology, vol. 18, No. Suppl.1, p. 1669, (May 2016) XP002773214, ISSN: 1536-1632,Retrieved from the Internet: <URL:https://rd.springer.com/content/pdf/10.1007%2Fs11307-016-0968-3.pdf> Abstract, control ID: 2324486 [retrieved on Aug. 24, 2017].

Inkster, J. et al., "Radiosynthesis and bioconjugation of [18F]FPy5yne, a prosthetic group for the 18F labeling of bioactive peptides," J. Label Compd. Radiopharm, vol. 51: 444-452. (2008).

Michel, K. et al., Development and evaluation of endothelin-A receptor (radio)ligands for positron emission tomography, J Med Chem., vol. 54(4):939-48 (2011).

Schrigten, D. et al., "A New Generation of Radiofluorinated Pyrimidine-2,4,6-triones as MMP-Targeted Radiotracers for Positron Emission Tomography," Med. Chem., vol. 55(1): 223-232 (2012).

* cited by examiner

SEQUENCE LISTING

```
<160> NUMBER OF SEQ ID NOS: 36

<210> SEQ ID NO 1
<211> LENGTH: 95
<212> TYPE: PRT
<213> ORGANISM: Homo sapiens

<400> SEQUENCE: 1

Gly Val Ser Asp Val Pro Arg Asp Leu Glu Val Val Ala Ala Thr Pro
1               5                  10                  15

Thr Ser Leu Leu Ile Ser Trp Arg Ala Gln Leu Ser Pro Ser Phe Tyr
            20                  25                  30

Tyr Arg Ile Thr Tyr Gly Glu Thr Gly Gly Asn Ser Pro Val Gln Glu
        35                  40                  45

Phe Thr Val Pro Asn Asp Val Met Thr Ala Thr Ile Ser Gly Leu Lys
    50                  55                  60

Pro Gly Val Asp Tyr Thr Ile Thr Val Tyr Ala Val Thr His Gly
65                  70                  75                  80

Val Tyr Phe Tyr Ser Pro Ile Ser Ile Asn Tyr Arg Thr Pro Cys
                85                  90                  95

<210> SEQ ID NO 2
```

```
<211> LENGTH: 88
<212> TYPE: PRT
<213> ORGANISM: Artificial Sequence
<220> FEATURE:
<223> OTHER INFORMATION: Synthetic

<400> SEQUENCE: 2

Glu Val Val Ala Ala Thr Pro Thr Ser Leu Leu Ile Ser Trp Ser Tyr
1               5                   10                  15

Asp Gly Pro Ile Asp Arg Tyr Tyr Arg Ile Thr Tyr Gly Glu Thr Gly
                20                  25                  30

Gly Asn Ser Pro Val Gln Glu Phe Thr Val Pro Pro Asp Gln Lys Thr
            35                  40                  45

Ala Thr Ile Ser Gly Leu Lys Pro Gly Val Asp Tyr Thr Ile Thr Val
    50                  55                  60

Tyr Ala Val Arg Leu Glu Glu Ala His Tyr Asn Arg Glu Phe Pro Ile
65                  70                  75                  80

Ser Ile Asn Tyr Arg Thr Pro Cys
                85

<210> SEQ ID NO 3
<211> LENGTH: 94
<212> TYPE: PRT
<213> ORGANISM: Homo sapiens

<400> SEQUENCE: 3

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
            50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 4
<211> LENGTH: 86
<212> TYPE: PRT
<213> ORGANISM: Homo sapiens

<400> SEQUENCE: 4

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Glu Thr Gly
                20                  25                  30

Gly Asn Ser Pro Val Gln Glu Phe Thr Val Pro Gly Ser Lys Ser Thr
            35                  40                  45

Ala Thr Ile Ser Gly Leu Lys Pro Gly Val Asp Tyr Thr Ile Thr Val
    50                  55                  60

Tyr Ala Val Thr Gly Arg Gly Asp Ser Pro Ala Ser Ser Lys Pro Ile
65                  70                  75                  80

Ser Ile Asn Tyr Arg Thr
                85
```

```
<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Met Gly Val Ser Asp Val Pro Arg Asp Leu
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gly Val Ser Asp Val Pro Arg Asp Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa may or may not be present; If one Xaa is
      present, Xaa is Met OR Gly; If both Xaa are present, then it is
      Met Gly

<400> SEQUENCE: 7

Xaa Xaa Ser Asp Val Pro Arg Asp Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa may or may not be present; If one Xaa is
      present, Xaa is Met OR Gly; If both Xaa are present, then it is
      Met Gly

<400> SEQUENCE: 8

Xaa Xaa Asp Val Pro Arg Asp Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa may or may not be present; If one Xaa is
      present, Xaa is Met OR Gly; If both Xaa are present, then it is
      Met Gly

<400> SEQUENCE: 9
```

```
Xaa Xaa Val Pro Arg Asp Leu
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa may or may not be present; If one Xaa is
      present, Xaa is Met OR Gly; If both Xaa are present, then it is
      Met Gly

<400> SEQUENCE: 10

Xaa Xaa Pro Arg Asp Leu
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa may or may not be present; If one Xaa is
      present, Xaa is Met OR Gly; If both Xaa are present, then it is
      Met Gly

<400> SEQUENCE: 11

Xaa Xaa Arg Asp Leu
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa may or may not be present; If one Xaa is
      present, Xaa is Met OR Gly; If both Xaa are present, then it is
      Met Gly

<400> SEQUENCE: 12

Xaa Xaa Asp Leu
1

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Met Ala Ser Thr Ser Gly
1               5

<210> SEQ ID NO 14
<211> LENGTH: 4
<212> TYPE: PRT
<213> ORGANISM: Artificial Sequence
<220> FEATURE:
```

```
<223> OTHER INFORMATION: Synthetic

<400> SEQUENCE: 14

Glu Ile Glu Lys
1

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Glu Gly Ser Gly Cys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Glu Ile Glu Lys Pro Cys Gln
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Glu Ile Glu Lys Pro Ser Gln
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Glu Ile Glu Lys Pro
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Glu Ile Glu Lys Pro Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic
```

<400> SEQUENCE: 20

Glu Ile Glu Lys Pro Cys
1               5

<210> SEQ ID NO 21
<211> LENGTH: 4
<212> TYPE: PRT
<213> ORGANISM: Artificial Sequence
<220> FEATURE:
<223> OTHER INFORMATION: Synthetic

<400> SEQUENCE: 21

Glu Ile Asp Lys
1

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Glu Ile Asp Lys Pro Cys Gln
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Glu Ile Asp Lys Pro Ser Gln
1               5

<210> SEQ ID NO 24
<211> LENGTH: 4
<212> TYPE: PRT
<213> ORGANISM: Artificial Sequence
<220> FEATURE:
<223> OTHER INFORMATION: Synthetic

<400> SEQUENCE: 24

Pro Ile Asp Lys
1

<210> SEQ ID NO 25
<211> LENGTH: 4
<212> TYPE: PRT
<213> ORGANISM: Artificial Sequence
<220> FEATURE:
<223> OTHER INFORMATION: Synthetic

<400> SEQUENCE: 25

Pro Ile Glu Lys
1

<210> SEQ ID NO 26
<211> LENGTH: 5
<212> TYPE: PRT
<213> ORGANISM: Artificial Sequence
<220> FEATURE:
<223> OTHER INFORMATION: Synthetic

```
<400> SEQUENCE: 26

Pro Ile Asp Lys Pro
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic

<400> SEQUENCE: 27

Pro Ile Glu Lys Pro
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Pro Ile Asp Lys Pro Ser
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Pro Ile Glu Lys Pro Ser
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Pro Ile Asp Lys Pro Cys
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic

<400> SEQUENCE: 31

Pro Ile Glu Lys Pro Cys
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32
```

```
Pro Ile Asp Lys Pro Ser Gln
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Pro Ile Glu Lys Pro Ser Gln
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic

<400> SEQUENCE: 34

Pro Ile Asp Lys Pro Cys Gln
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Pro Ile Glu Lys Pro Cys Gln
1               5

<210> SEQ ID NO 36
<211> LENGTH: 20
<212> TYPE: PRT
<213> ORGANISM: Artificial Sequence
<220> FEATURE:
<223> OTHER INFORMATION: Synthetic

<400> SEQUENCE: 36

Met Glu Thr Asp Thr Leu Leu Leu Trp Val Leu Leu Leu Trp Val Pro
1               5                   10                  15

Gly Ser Thr Gly
            20
```

IMAGING METHODS USING 18F-RADIOLABELED BIOLOGICS

CROSS-REFERENCE TO RELATED APPLICATIONS

This application is a 35 U.S.C. 371 national stage filing of International Application No. PCT/US2017/035271, filed May 31, 2017, which claims priority to U.S. Provisional Application No. 62/344,289, filed Jun. 1, 2016. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Nov. 26, 2018, is named MXI-552US_Sequence Listing.txt and is 10,107 bytes in size.

FIELD

The invention relates to $^{18}$F-prosthetic groups and the synthesis and use of $^{18}$F-labeled compositions for imaging various processes within the body, for detecting the location of molecules associated with disease pathology, and for monitoring disease progression.

BACKGROUND

Positron emission tomography (PET) is a non-invasive imaging technique that has become one of the most widely used methods in diagnostic medicine and drug development, with high sensitivity (fmoles), high resolution (4-10 mm) and tissue accretion that can be quantitated. The valuable in vivo functional information about biological processes in living subjects provided by PET imaging also provides a unique translational medical advantage in that the same tool can be used both preclinically and clinically.

PET relies on the design and synthesis of molecules labeled with a positron-emitting radioisotopes including $^{18}$F, $^{64}$Cu, $^{11}$C, $^{15}$O, $^{13}$N, $^{66}$Ga, $^{68}$Ga, $^{76}$Br, $^{89}$Zr, $^{94m}$Tc, $^{86}$Y and $^{124}$I. In vivo, these radiotracers or radioligands emit positrons from the nucleus of the isotope with different energies depending on the isotope used. The energy of the ejected positron controls the average distance that it travels before it collides with an electron resulting in the emission of two 511 keV gamma rays in opposite directions. The gamma rays produced by this positron annihilation event are detected by the PET imaging scanner to produce planar and tomographic images that reveal distribution of the radiotracer as a function of time. Accordingly, isotopes that are pure positron emitters with low ejection energy isotopes are preferred for PET imaging to minimize the distance traveled by the positron before annihilation and dosimetry problems caused by other emissions such as gamma rays, alpha particles or beta particles.

In addition, the half-life of the isotope used in PET imaging must be long enough to allow synthesis and analysis of the radiotracer molecule, injection into the patient, in vivo localization, clearance from non-target tissues and the production of a clear image. $^{18}$F ($\beta^+$635 keV 97%, t½ 110 min) is one of the most widely used PET emitting isotopes because of its low positron emission energy, lack of side emissions and suitable half-life.

Traditionally, labeling biological molecules, such as peptides and proteins, with $^{18}$F has been challenging due to the harsh conditions (high temperatures, organic solvents and strong basic conditions) required for labeling with this radionuclide. One approach for labeling proteins with $^{18}$F is the use of a prosthetic group which can withstand harsh fluorination conditions. Numerous prosthetic groups have been reported (e.g., reviewed in Nucl. Med. Bio. 34:5, 2007), but many of these $^{18}$F-labeled prosthetic groups require organic solvents and are not amenable for labeling protein or protein like molecules in aqueous media or have other undesirable properties.

Accordingly, there is still a continuing need for rapid, simple methods of $^{18}$F-labeling targeting moieties, such as proteins and peptides, to produce radiotracer compositions which retain sufficient specific activity and stability for use in in vivo imaging methodologies.

SUMMARY

The present invention is based is based at least in part on the discovery of an $^{18}$F-labeled prosthetic group that contains a nitro-pyridine linked to a polyethylene glycol (PEG) moiety and a terminal azide, which prosthetic group is water soluble and less volatile than other agents used for $18^F$-labeling, and that reactions incorporating this $^{18}$F-labeled prosthetic group into biological molecules (e.g., peptides and proteins) can be monitored by UV. These advantageous features provide an efficient, rapid and reproducible method of producing $^8$F-labeled-biomolecules under conditions which retain the biological activity of the biomolecule. In certain embodiments, biomolecules (e.g., peptides and proteins) containing bifunctional conjugating moieties (e.g., with ring constrained alkyne groups, such as bifunctional chelators) form covalent bonds with the terminal azide of the $^{18}$F-labeled prosthetic group via a "click" biorthogonal reaction to produce radiolabeled probes that are stable under physiological conditions. The UV absorbance of the resultant product further provides a practical, sensitive and rapid analytical method for determining the radiochemical purity of the product.

$^{18}$F is an attractive PET radionuclide with a 1.8 hour radioactive half life, which provides a same day imaging tool, and where the targeting agent to which it is linked has a similar half-life, produces excellent images with less radiation exposure to the patient. As further shown in the Examples, an $^{18}$F-labelled anti-PD-L1 Adnectin specifically and efficiently labelled human PD-L1 positive tumors in mice, human lung tumor tissue, and PD-L1 positive tumors in cynomolgus monkeys.

In one aspect, provided herein is a $^{18}$F-labeled prosthetic group with the following structure,

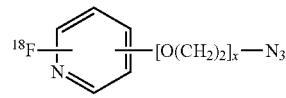

or a pharmaceutically acceptable salt thereof, wherein x is an integer from 1 to 8. In some embodiments, x is an integer from 2 to 6. In some embodiments x is an integer from 3 to 5. In some embodiments, x is 4. In some embodiments, the $[O(CH_2)_2]_x$ moiety is present in the 1-2, 1-3 or 1-4 configuration relative to the nitrogen on the pyridine ring. In related embodiments, $^{18}$F is attached to the pyridine ortho to the N atom. In some embodiments, the pharmaceutically acceptable salt is selected from the group consisting of fluoro, bromo, chloro and iodo salts. In one embodiment, the salt is a trifluoromethanesulfonate salt. In some embodiments, the $^{18}$F-radiolabeled prosthetic group or pharmaceutically acceptable salt is water soluble. In some embodiments, the $^{18}$F-radiolabeled prosthetic group or pharmaceutically acceptable salt is nonvolatile.

In some embodiments, the $^{18}$F-radiolabeled compound has the structure

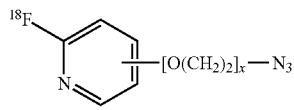

or a pharmaceutically acceptable salt thereof, wherein x is an integer from 1 to 8. In some embodiments, x is an integer from 2 to 6. In some embodiments x is an integer from 3 to 5. In some embodiments, x is 4. In some embodiments, the [O(CH$_2$)$_2$]$_x$ moiety is present in the 1-2, 1-3 or 1-4 configuration relative to the nitrogen on the pyridine ring. In some embodiments, the pharmaceutically acceptable salt is selected from the group consisting of fluoro, bromo, chloro and iodo salts. In one embodiment, the salt is a trifluoromethanesulfonate salt. In some embodiments, the $^{18}$F-radiolabeled prosthetic group or pharmaceutically acceptable salt is nonvolatile.

In some embodiments, the $^{18}$F-radiolabeled compound has the structure

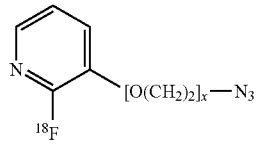

or a pharmaceutically acceptable salt thereof, wherein x is an integer from 1 to 8. In some embodiments, x is an integer from 2 to 6. In some embodiments x is an integer from 3 to 5. In some embodiments, x is 4. In some embodiments, the pharmaceutically acceptable salt is selected from the group consisting of fluoro, bromo, chloro and iodo salts. In one embodiment, the salt is a trifluoromethanesulfonate salt. In some embodiments, the $^{18}$F-radiolabeled prosthetic group or pharmaceutically acceptable salt is nonvolatile.

In some embodiments, the $^{18}$F-radiolabeled compound has the structure

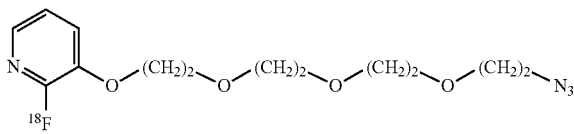

or a pharmaceutically acceptable salt thereof.

In certain embodiments, the pyridine ring of the $^{18}$F-labeled prosthetic group contains one or more additional substituents which do not interfere with fluorination of the molecule. In some embodiments, the additional substituent is a C$_{1-6}$ alkyl, for example, methyl, ethyl or propyl.

In a related aspect, provided herein is an $^{18}$F-radiolabeled prosthetic group having the structure

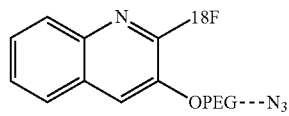

wherein "OPEG" is [O(CH$_2$)$_2$]$_x$, and x is an integer from 1 to 8, or a pharmaceutically acceptable salt thereof. In some embodiments, x is an integer from 2 to 6. In some embodiments, x is an integer from 3 to 5. In one embodiment, x is 4. In some embodiments, the $^{18}$F-radiolabeled prosthetic group or pharmaceutically acceptable salt is nonvolatile.

In certain aspects, provided herein is an $^{18}$F-radiolabeled protein-based probe comprising a $^{18}$F-radiolabeled prosthetic group as described herein, a bifunctional chelator or conjugating (BFC) moiety and a protein, wherein the radiolabeled protein-based probe has the following structure,

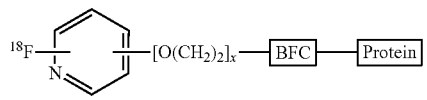

or pharmaceutically acceptable salt thereof.

In certain aspects, provided herein is an $^{18}$F-radiolabeled protein-based probe comprising a $^{18}$F-radiolabeled prosthetic group as described herein, a bifunctional chelator or conjugating (BFC) and a protein, wherein the radiolabeled protein-based probe has the following structure,

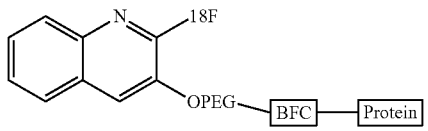

or a pharmaceutically acceptable salt thereof.

In some embodiments, the BFC is a cyclooctyne comprising a reactive group that forms a covalent bond with an amine, carboxyl, carbonyl or thiol functional group on the protein. In some embodiments, the cyclooctyne is selected from the group consisting of dibenzocyclooctyne (DIBO), biarylazacyclooctynone (BARAC), dimethoxyazacyclooctyne (DIMAC) and dibenzocyclooctyne (DBCO). In some embodiments, the cyclooctyne is DBCO.

In some embodiments, the BFC further comprises a polyethylene glycol (PEG)$_y$ spacer arm, wherein y is an integer from 1 to 8. In some embodiments, y is an integer from 2 to 6. In some embodiments, y is 4 or 5.

In some embodiments, the BFC is DBCO-PEG4-NHS-Ester, DBCO-Sulfo-NHS-Ester, DBCO-PEG4-Acid, DBCO-PEG4-Amine or DBCO-PEG4-Maleimide. In some embodiments, the BFC is DBCO-PEG4-Maleimide.

In certain embodiments, provided herein is an $^{18}$F-radiolabeled protein-based probe with the following structure,

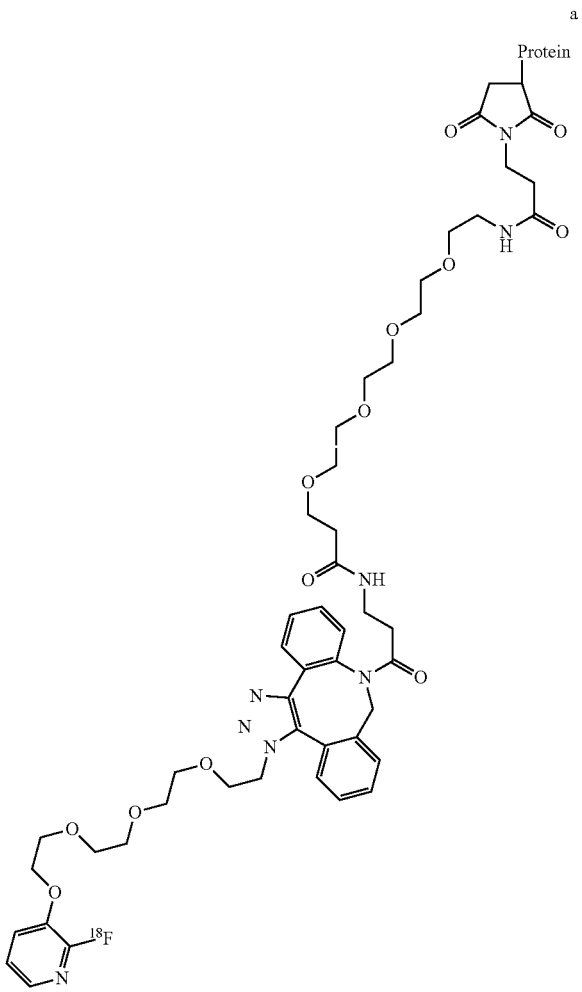

a wherein the maleimide group of the BFC is covalently linked to the thiol group on a cysteine residue of the protein. In some embodiments, the cysteine residue is at the C-terminus of the protein.

In related embodiments, the protein portion of the $^{18}$F-radiolabeled protein-based probe comprises or consists of a peptide, consisting, e.g., of less than 100, 50, 25, 20, 15 or 10 amino acid residues. In certain embodiments, the protein portion of the $^{18}$F-radiolabeled protein-based probe comprises a ligand. In some embodiments, the protein portion of the probe comprises an antibody or antibody fragment. In some embodiments, the protein portion of the probe comprises a fibronectin based scaffold (FBS). Any other type of protein may be used.

In related embodiments, the protein portion of the $^{18}$F-radiolabeled protein-based probe binds to a biological molecule associated with a disease. In some embodiments, the disease is selected from the group consisting of solid cancers, hematopoietic cancers, hematological cancers, autoimmune disease, neurodegenerative disease, cardiovascular disease and pathogenic infections. In certain embodiments, the probe binds to a tumor-associated antigen. In certain embodiments, the probe binds to a protein present on a pathogenic organism, e.g., a virus, bacterium or fungus.

In certain embodiments, the $^{18}$F-radiolabeled protein-based probe provided herein may be in the form of a pharmaceutical composition.

In a related aspect, provided herein is a method of obtaining an image of an $^{18}$F-radiolabeled protein-based probe as provided herein, the method including the steps of (a) administering the $^{18}$F-radiolabeled protein-based probe to a subject; and (b) imaging in vivo the distribution of the $^{18}$F-radiolabeled protein-based probe by positron emission tomography (PET) scanning. In some embodiments, the imaged distribution of the $^{18}$F-radiolabeled protein-based probe is indicative of the presence or absence of a disease or predictive of whether a subject is likely to respond to a treatment and/or should be receiving a given treatment.

In a related aspect, provided herein is a method of diagnosing the presence of a disease in a subject, the method including the steps of (a) administering to a subject in need thereof an $^{18}$F-radiolabeled protein-based probe as provided herein which binds to a target molecule associated with the presence of the disease; and (b) obtaining an radio-image of at least a portion of the subject to detect the presence or absence of the $^{18}$F-radiolabeled protein-based probe; wherein the presence and location of the $^{18}$F-radiolabeled protein-based probe above background is indicative of the presence and location of the disease.

In a related aspect, provided herein is a method of monitoring the progress of a disease in a subject, the method including the steps of (a) administering to a subject in need thereof an $^{18}$F-radiolabeled protein-based probe as provided herein which binds to a target molecule associated with the presence of the disease at a first time point and obtaining an image of at least a portion of the subject to determine the amount of the diseased cells or tissue; and (b) administering to the subject the $^{18}$F-radiolabeled protein-based probe at one or more subsequent time points and obtaining an image of at least a portion of the subject at each time point; wherein the dimension and location of the diseased cells or tissue at each time point is indicative of the progress of the disease.

In a related aspect, provided herein is a method of quantifying diseased cells or tissues in a subject, the method including the steps of (a) administering to a subject having diseased cells or tissues with an $^{18}$F-radiolabeled protein-based probe as described herein which binds to a target molecule located with the diseased cells or tissues; and (b) detecting radioactive emissions of the $^{18}$F in the diseased cells or tissue, wherein the level and distribution of the radioactive emissions in the diseased cells or tissues is a quantitative measure of the diseased cells or tissues.

In a related aspect, provided herein is a method of screening for an agent for treating a disease including the steps of (a) contacting a cells expressing a target protein associated with the disease with an $^{18}$F-radiolabeled protein-based probe as provided herein which binds to the target protein in the presence and absence of a candidate agent; and (b) imaging the cells in the presence and absence of the candidate agent using positron emission tomography (PET), wherein a decrease in the amount of radioactive emissions in the presence of the candidate agent is indicative of that the agent binds to the target protein.

In some embodiments of these methods, the disease is selected from the group consisting of solid cancers, hematopoietic cancers, hematological cancers, autoimmune disease, neurodegenerative disease, cardiovascular disease and pathogenic infection (e.g., viral, bacterial or fungal infections).

In a related aspect, provided herein is a method of obtaining a quantitative image of tissues or cells expressing a target protein, the method including the steps of contacting the cells or tissue with an $^{18}$F-radiolabeled protein-based probe as provided herein which binds to the target protein, and detecting or quantifying the tissue expressing the target protein using positron emission tomography (PET).

Provided herein are methods for determining whether a subject is likely to respond to a therapy, wherein the method comprises detecting qualitatively or quantitatively a protein in the subject, and if the protein is qualitatively or quantitatively detected in the subject, then the subject is likely to respond to a therapy. For example, in some embodiments, PD-L1 is detected in a subject having cancer, and the presence of a certain amount of PD-L1 is indicative of whether a subject will respond to a therapy with a PD-1 or PD-L1 antagonist. Predictive levels of PD-L1 protein are required for certain cancers and therapies, e.g., for PD-1 or PD-L1 antagonist therapies, such as KEYTRUDA or TECENTRIQ.

Also provided are methods for treating a subject having a disease, e.g., cancer, comprising detecting qualitatively or quantitatively a protein in the subject, and if the protein is qualitatively or quantitatively detected in the subject, then treating the subject with a therapy designed for treating subjects having the disease and a given level of the protein. For example, a method may comprise treating a subject having cancer by administering to the subject an imaging agent to PD-L1, e.g., as described herein, and determining qualitatively or quantitatively the level of PD-L1, wherein if PD-L1 is present (e.g., in certain amounts), the subject is administered a cancer therapy requiring the presence of a given level of PD-L1, e.g., a PD-1 antagonist.

In some embodiments of the methods provided herein, the $^{18}$F-radiolabeled protein-based probe comprises a ligand. In some embodiments, the $^{18}$F-radiolabeled protein-based probe comprises an antibody or antibody fragment. In some embodiments, the $^{18}$F-radiolabeled protein-based probe comprises a fibronectin based scaffold (FBS). In some embodiments, the $^{18}$F-radiolabeled protein-based probe binds to a tumor-associated antigen. In still other embodiments, the $^{18}$F-radiolabeled protein-based probe binds to a protein present on a pathogenic organism (e.g., a virus, bacterium or fungus).

Also provided herein are kits containing the reaction precursors for producing the $^{18}$F-radiolabeled protein-based probes provided herein (e.g., a non-radiolabeled prosthetic group, BFC-linked protein probe and reagents for carrying out a bioorthogonal click reaction), and instructions for producing the $^{18}$F-radiolabeled protein-based probe.

Accordingly, in one aspect, provided herein is a method of producing a $^{18}$F-labeled prosthetic group having the following structure,

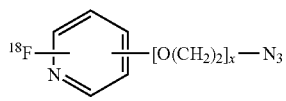

wherein x is an integer from 1 to 8, the method including the steps of (a) providing a solution of a compound a with the following structure:

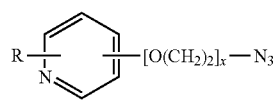

a wherein x is an integer from 1 to 8, and R is NO$_2$, Br, F or

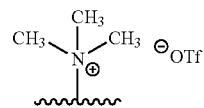

and is ortho to the N atom of the pyridine ring; (b) providing a mixture of $^{18}$F in $^{18}$O water, 4,7,13,16,21,24-hexaoxa-1,10-diazabicyclo[8.8.8]hexacosane and a weak base; (c) drying the mixture from step (b) to form a solid; and (d) reacting the solution from step (a) with the solid from step (c) to form the $^{18}$F-labeled compound.

In certain embodiments, the method produces an $^{18}$F-pyridine prosthetic group with the following structure b

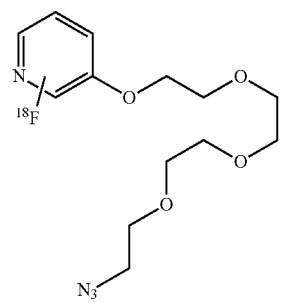

b (where $^{18}$F is ortho to the N atom), and includes the steps of (a) providing a solution of the compound of the structure

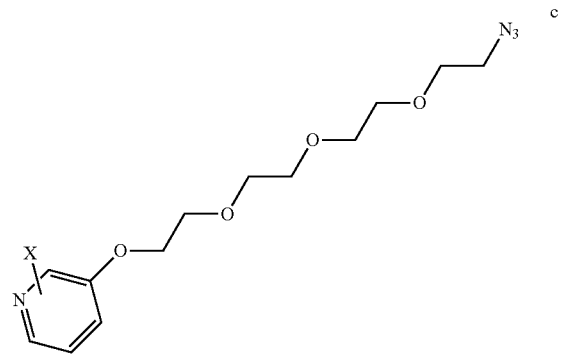

c (where X is ortho to the N atom) where X is NO$_2$, Br or

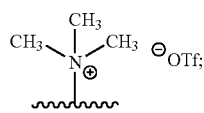

(b) providing a mixture of $^{18}$F in $^{18}$O water, 4,7,13,16,21,24-hexaoxa-1,10-diazabicyclo[8.8.8]hexacosane and weak base; (c) drying the mixture from step (b) to form a solid; and (d) reacting the solution from step (a) with the solid from step (c) to form the $^{18}$F-labeled compound.

In certain embodiments, the starting compound from step a) described above, X is NO$_2$. In certain embodiments, X is attached to the carbon atom ortho to the N atom and the PEG-N$_3$ side chain. In certain embodiments the weak base in step b) is $K_2CO_3$, cesium carbonate or tetrabutylammonium hydroxide. In one embodiment, the weak base in step b) is $K_2CO_3$.

In a related aspect, a method for the $^{18}F$ labeling of a protein is provided which includes the step of coupling the $^{18}F$-radiolabeled prosthetic group of formula b with the protein to be radiolabeled in a "click reaction" to form the $^{18}F$-radiolabeled protein. In some embodiments, the bioorthogonal click reaction is metal free (e.g., copper free click reaction). In some embodiments, the protein comprises a bifunctional conjugating (BFC) moiety (e.g., a bifunctional chelator). In some embodiments, the protein comprises a cyclooctyne BFC. In some embodiments, the protein comprises DBCO-PEG4-Maleimide or is covalently linked to it.

Other features and advantages of the instant disclosure will be apparent from the following detailed description and examples, which should not be construed as limiting.

DETAILED DESCRIPTION

Figure 1:
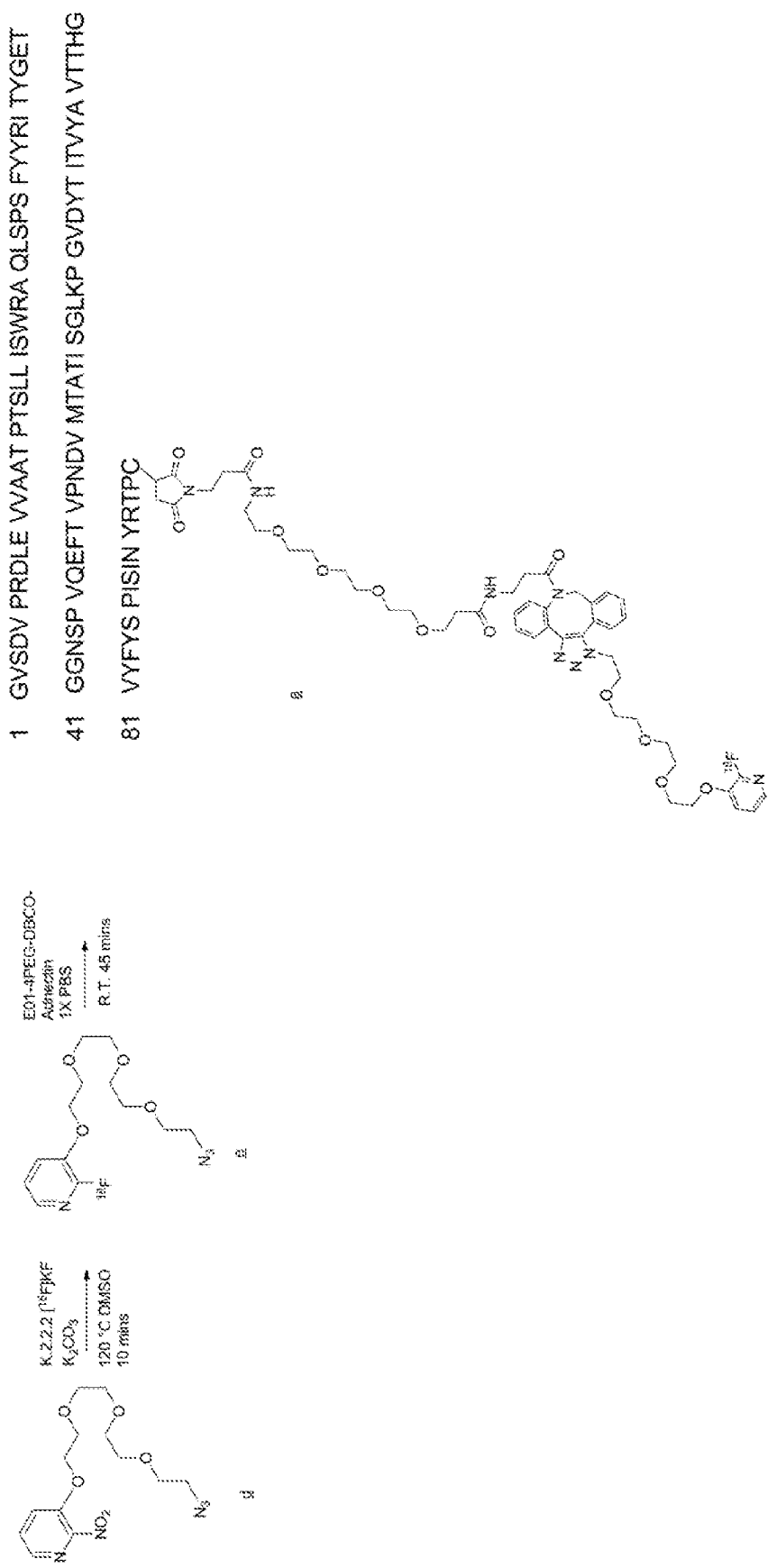
FIG. 1 is a schematic for the chemical synthesis of [$^{18}F$]-E01-4PEG-DBCO-FPPEGA. The E01 portion of the molecule has the sequence set forth in SEQ ID NO: 1.

Described herein are $^{18}F$-prosthetic groups and methods for producing the $^{18}F$-prosthetic groups. Also described herein are radiolabeled compositions containing the $^{18}F$-prosthetic groups and the use of these radiolabeled compositions to diagnose, localize, monitor and/or assess diseased cells and/or tissues, and related biological conditions.

Definitions

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of mass spectroscopy, NMR, HPLC, protein chemistry, biochemistry, recombinant DNA techniques and pharmacology are employed.

As used herein, the singular forms "a", "an" and "the" include plural referents unless the context clearly dictates otherwise. The use of "or" or "and" means "and/or" unless stated otherwise. Furthermore, use of the term "including" as well as other forms, such as "include", "includes", and "included", is not limiting.

As used herein, "about" means within plus or minus ten percent of a number. For example, "about 100" would refer to any number between 90 and 110.

As used herein, "medical imaging" refers to the techniques and processes used to create images of the subject's body (or parts thereof) for clinical purposes (medical procedures seeking to reveal, diagnose or monitor disease) or medical science (including the study of normal anatomy and physiology).

As used herein, "positron emission tomography" or "PET" refers to a non-invasive, nuclear medicine technique that produces a three-dimensional image of tracer location in the body. The method detects pairs of gamma rays emitted indirectly by a positron-emitting radionuclide (tracer), which is introduced into the body on a biologically active molecule. PET imaging tools have a wide variety of uses and aid in drug development both preclinically and clinically. Exemplary applications include direct visualization of in vivo saturation of targets; monitoring uptake in normal tissues to anticipate toxicity or patient to patient variation; quantifying diseased tissue; tumor metastasis; and monitoring drug efficacy over time, or resistance over time.

The term "bioorthogonal chemistry" refers to any chemical reaction that can occur inside of living systems without interfering with native biochemical processes. The term includes chemical reactions that are chemical reactions that occur in vitro at physiological pH in, or in the presence of water. To be considered bioorthogonol, the reactions are selective and avoid side-reactions with other functional groups found in the starting compounds. In addition, the resulting covalent bond between the reaction partners should be strong and chemically inert to biological reactions and should not affect the biological activity of the desired molecule.

The term "click chemistry" refers to a set of reliable and selective bioorthogonal reactions for the rapid synthesis of new compounds and combinatorial libraries. Properties of for click reactions include modularity, wideness in scope, high yielding, stereospecificity and simple product isolation (separation from inert by-products by non-chromatographic methods) to produce compounds that are stable under physiological conditions. In radiochemistry and radiopharmacy, click chemistry is a generic term for a set of labeling reactions which make use of selective and modular building blocks and enable chemoselective ligations to radiolabel biologically relevant compounds in the absence of catalysts. A "click reaction" can be with copper, or it can be a copper-free click reaction.

The term "prosthetic group" or "bifunctional labeling agent" refers to a small organic molecule containing a radionulide (e.g., $^{18}F$) that is capable of being linked to peptides or proteins.

The term "chelator ligand" as used herein with respect to radiopharmaceutical chemistry refers to a bifunctional chelator or bifunctional conjugating (BFC) moiety (used interchangeably herein) that covalently links a radiolabeled prosthetic group to a biologically active targeting molecule (e.g., peptide or protein). BFCs utilize functional groups such as carboxylic acids or activated esters for amide couplings, isothiocyanates for thiourea couplings and maleimides for thiol couplings.

As used herein, "target" as a general reference to a "biological target" refers to a cell, tissue (e.g., cancer or tumor), molecule thereof, a pathogenic microorganism (e.g., bacteria, virus, fungus, plant, prion, protozoa or portion thereof) or molecule associated with a biological pathway, or a biological phenomenon, such as tissue inflammation, plaque formation, etc.

The term "targeting ligand", "targeting agent" or "targeting molecule" are used interchangeably to refer to a molecule, such as peptide, protein, glycoprotein, etc., that binds to another molecule. In certain embodiments, a targeting agent is bound to the $^{18}$F-prosthetic group in order to "target" a molecule associated with a particular cell, tissue, pathogen or biological pathway.

"Polypeptide" as used herein refers to any sequence of two or more amino acids, regardless of length, post-translation modification, or function. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life).

Polypeptide modifications can include the attachment of another structure such as a cyclic compound or other molecule to the polypeptide and can also include polypeptides that contain one or more amino acids in an altered configuration (i.e., R or S; or, L or D).

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or nonreducing condition using Coomassie blue or, preferably, silver stain. Isolated polypeptide includes the polypeptide in situ within recombinant cells since at least one component of the polypeptide's natural environment will not be present. Ordinarily, however, isolated polypeptides will be prepared by at least one purification step.

The terms "specifically binds," "specific binding," "selective binding, and "selectively binds," as used interchangeably herein refers to a peptide or polypeptide that exhibits affinity for a biological target, but does not significantly bind (e.g., less than about 10% binding) to other molecules as measured by a technique available in the art such as, but not limited to, Scatchard analysis and/or competitive binding assays (e.g., competition ELISA, BIACORE assay).

The term "preferentially binds" as used herein refers to the situation in which a peptide or protein binds a selected biological target at least about 20% greater than it binds a different biological target as measured by a technique available in the art such as, but not limited to, Scatchard analysis and/or competitive binding assays (e.g., competition ELISA, BIACORE assay).

The term "$K_D$," as used herein, is intended to refer to the dissociation equilibrium constant of a protein-protein interaction (e.g., $^{18}$F-radiolabeled-protein based probe-target molecule)—or the affinity of an $^{18}$F-radiolabeled-protein based probe for a target protein, as measured using a surface plasmon resonance assay or a cell binding assay. A "desired $K_D$," as used herein, refers to a $K_D$ of an $^{18}$F-radiolabeled-protein based probe that is sufficient for the purposes contemplated. For example, a desired $K_D$ may refer to the $K_D$ of an $^{18}$F-radiolabeled-protein based probe required to elicit a functional effect in an in vivo imaging assay or in vitro assay, e.g., a cell-based luciferase assay.

The term "$k_{ass}$", as used herein, is intended to refer to the association rate constant for the association of an $^{18}$F-radiolabeled-protein based probe into an $^{18}$F-radiolabeled-protein based probe/target protein complex.

The term "$k_{diss}$", as used herein, is intended to refer to the dissociation rate constant for the dissociation of an $^{18}$F-radiolabeled-protein based probe from the $^{18}$F-radiolabeled-protein based probe/target protein complex.

The term "$IC_{50}$", as used herein, refers to the concentration of an $^{18}$F-radiolabeled-protein based probe that inhibits a response, either in an in vitro or an in vivo assay, to a level that is 50% of the maximal inhibitory response, i.e., halfway between the maximal inhibitory response and the untreated response.

The term "PK" is an acronym for "pharmacokinetic" and encompasses properties of a compound including, by way of example, absorption, distribution, metabolism, and elimination by a subject. A "PK modulation protein" or "PK moiety" as used herein refers to any protein, peptide, or moiety that affects the pharmacokinetic properties of a biologically active molecule when fused to or administered together with the biologically active molecule. Examples of a PK modulation protein or PK moiety include PEG, human serum albumin (HSA) binders (as disclosed in U.S. Publication Nos. 2005/0287153 and 2007/0003549, PCT Publication Nos. WO 2009/083804 and WO 2009/133208), human serum albumin and variants thereof, transferrin and variants thereof, Fc or Fc fragments and variants thereof, and sugars (e.g., sialic acid).

The "serum half-life" of a protein or compound can generally be defined as the time taken for the serum concentration of the polypeptide to be reduced by 50%, in vivo, for example due to degradation of the sequence or compound and/or clearance or sequestration of the sequence or compound by natural mechanisms. The half-life can be determined in any manner known per se, such as by pharmacokinetic analysis. Suitable techniques will be clear to the person skilled in the art, and may for example generally involve the steps of suitably administering to a subject a suitable dose of the amino acid sequence or compound described herein; collecting blood samples or other samples from the subject at regular intervals; determining the level or concentration of the amino acid sequence or compound described herein in said blood sample; and calculating, from (a plot of) the data thus obtained, the time until the level or concentration of the amino acid sequence or compound described herein has been reduced by 50% compared to the initial level upon dosing. Reference is, for example, made to the standard handbooks, such as Kenneth, A. et al., Chemical Stability of Pharmaceuticals: A Handbook for Pharmacists and in Peters et al., Pharmacokinete Analysis: A Practical Approach (1996). Reference is also made to Gibaldi, M. et al., Pharmacokinetics, 2nd Rev. Edition, Marcel Dekker (1982).

Half-life can be expressed using parameters such as the $t_{1/2}$-alpha, $t_{1/2}$-beta, HL_Lambda_z, and the area under the curve (AUC). In the present specification, an "increase in half-life" refers to an increase in any one of these parameters, any two of these parameters, any three of these parameters or all four of these parameters. An "increase in half-life" in particular refers to an increase in the $t_{1/2}$-beta, and/or HL_Lambda_z, either with or without an increase in the $t_{1/2}$-alpha and/or the AUC or both.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

The terms "diagnosis" or "detection" can be used interchangeably. Whereas diagnosis usually refers to defining a tissue's specific histological status, detection recognizes and locates a tissue, lesion or organism containing a particular detectable target.

The term "detectable" refers to the ability to detect a signal over the background signal. The term "detectable signal" as used herein in the context of imaging agents and diagnostics, is a signal derived from non-invasive imaging techniques such as, but not limited to, positron emission tomography (PET). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between the detectable signal and the background. Standards and/or calibration curves can be used to determine the relative intensity of the detectable signal and/or the background.

A "detectably effective amount" of a composition comprising an imaging agent described herein is defined as an amount sufficient to yield an acceptable image using equipment that is available for clinical use. A detectably effective amount of an imaging agent provided herein may be administered in more than one injection. The detectably effective amount can vary according to factors such as the degree of susceptibility of the individual, the age, sex, and weight of the individual, idiosyncratic responses of the individual, and the like. Detectably effective amounts of imaging compositions can also vary according to instrument and methodologies used. Optimization of such factors is well within the level of skill in the art.

As used herein, "administering," as used in the context of imaging agents refers to the physical introduction of a composition comprising an imaging agent to a subject, using any of the various methods and delivery systems known to those skilled in the art. Preferred routes of administration for the imaging agents described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an imaging agent described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The terms "co-administration" or the like, as used herein, are meant to encompass administration of the selected pharmaceutical agents to a single patient, and are intended to include regimens in which the agents are administered by the same or different route of administration or at the same or different time.

The terms "patient" and "subject" refer to a human.

The term "sample" can refer to a tissue sample, cell sample, a fluid sample, and the like. The sample may be taken from a subject. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue.

The term "isotopically pure" means that the element, compound, or composition contains a greater proportion of one isotope in relation to other isotopes. In certain embodiments, the element, compound, or composition is greater than about 40%, 50%, or 60% isotopically pure.

As used herein, a labeled molecule is "purified" when the labeled molecule is partially or wholly separated from unlabeled molecules, so that the fraction of labeled molecules is enriched compared to the starting mixture. A "purified" labeled molecule may comprise a mixture of labeled and unlabeled molecules in almost any ratio, including but not limited to about 5:95; 10:90; 15:85; 20:80; 25:75; 30:70; 40:60; 50:50; 60:40; 70:30; 75:25; 80:20; 85:15; 90:10; 95:5; 97:3; 98:2; 99:1 or 100:0.

The group "OTf" refers to triflate having the formula $CF_3SO_3$ or trifluoromethanesulfate.

The term "halo" or, alternatively, "halogen" or "halide" means fluoro, chloro, bromo or iodo.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

Various aspects described herein are described in further detail in the following subsections.

I. $^{18}$F Radiolabeled Prosthetic Groups

In one aspect, provided herein is an $^{18}$F-radiolabeled compound containing a prosthetic group for use in a bioorthogonal reaction involving 1,3-dipolar cycloaddition between an azide and a cyclooctyne which proceeds selectively under water tolerant conditions. The $^{18}$F-radiolabeled prosthetic groups of the invention are soluble in 100% aqueous, and there is no need for an organic phase to link the prosthetic group to a peptide or protein molecule. This feature is particularly advantageous as many biologics (e.g., peptides or proteins), cannot withstand even small amounts of organic solvents, with degradation and aggregation issues.

Additionally, unlike aliphatic prosthetic groups, with the instant prosthetic group, the $^{18}$F fluorination reaction can be monitored with UV. The $^{18}$F-radiolabeled prosthetic groups described herein are not volatile. Moreover, $^{18}$F-radiolabeled prosthetic groups provided may be incorporated into biologics using a copper free click chemistry, e.g., as described in the Examples, thus avoiding the stability issues observed in some biologics when copper mediated click chemistry is used.

In one aspect, provided herein is a PEGylated $^{18}$F-pyridine covalently bound to an azide with the following structure,

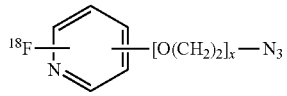

or a pharmaceutically acceptable salt thereof, wherein x is an integer from 1 to 8. In some embodiments, x is an integer from 2 to 6. In some embodiments x is an integer from 3 to 5. In some embodiments, x is 4. In related embodiments, $^{18}$F is attached to the pyridine ortho to the N atom. In some embodiments, the $[O(CH_2)_2]_x$ moiety is present in the 1-3 configuration relative to the nitrogen on the pyridine ring. In some embodiments, the $[O(CH_2)_2]_x$ moiety is present in the 1-2 configuration relative to the nitrogen on the pyridine ring. In other embodiments, the $[O(CH_2)_2]_x$ moiety is present in the 1-4 configuration relative to the nitrogen on the pyridine ring.

In some embodiments, the $^{18}$F-radiolabeled compound has the structure

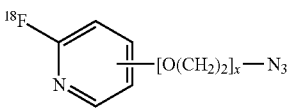

or a pharmaceutically acceptable salt thereof, wherein x is an integer from 1 to 8. In some embodiments, x is an integer from 2 to 6. In some embodiments x is an integer from 3 to 5. In some embodiments, x is 4. In some embodiments, the $[O(CH_2)_2]_x$ moiety is present in the 1-3 configuration relative to the nitrogen on the pyridine ring. In some embodiments, the $[O(CH_2)_2]_x$ moiety is present in the 1-2 configuration relative to the nitrogen on the pyridine ring. In other embodiments, the $[O(CH_2)_2]_x$ moiety is present in the 1-4 configuration relative to the nitrogen on the pyridine ring.

In some embodiments, the $^{18}$F-radiolabeled compound has the structure

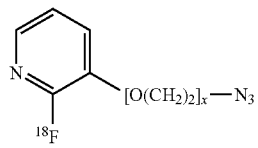

wherein x is an integer from 1 to 8. In some embodiments, x is an integer from 2 to 6. In some embodiments x is an integer from 3 to 5. In some embodiments, x is 4.

In some embodiments, the $^{18}$F-radiolabeled compound is [$^{18}$F]-3-(2-(2-(2-(2-azidoethoxy)ethoxy)ethoxy)ethoxy)-2-fluoropyridine ($^{18}$F-FPPEGA) and has the structure

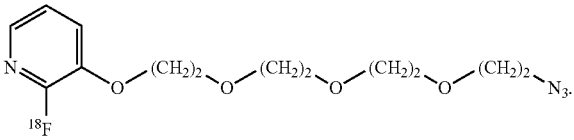

In alternative embodiments, the $^{18}$F-radiolabeled prosthetic group may contain additional groups on the pyridine ring which do not interfere with the fluorination reaction. In certain embodiments, additions to the pyridine ring include $C_{1-6}$ alkyl groups, for example methyl, ethyl and propyl.

In still other embodiments, the $^{18}$F-radiolabeled prosthetic group is a fused ring system with the following structure:

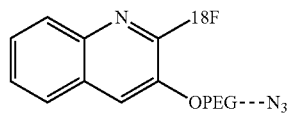

wherein "OPEG" is $[O(CH_2)_2]_x$, and x is an integer from 1 to 8. In some embodiments, x is an integer from 2 to 6. In some embodiments x is an integer from 3 to 5. In some embodiments, x is 4.

In a related aspect, provided herein is a method of preparing a PEGylated $^{18}$F-pyridine covalently bound to an azide with the following structure,

wherein x is an integer from 1 to 8, the method comprising the steps of (a) providing a solution of a compound a with the following structure:

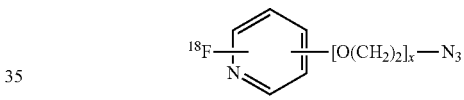

wherein x is an integer from 1 to 8, and R is NO$_2$, Br, F or

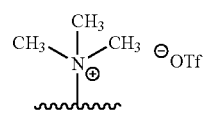

and is ortho to the N atom of the pyridine ring;

(b) providing a mixture of $^{18}$F in $^{18}$O water, 4,7,13,16,21,24-hexaoxa-1,10-diazabicyclo[8.8.8]hexacosane and a weak base;

(c) drying the mixture from step (b) to form a solid; and (d) reacting the solution from step (a) with the solid from step (c) to form the $^{18}$F-labeled compound.

In certain embodiments, the method produces a $^{18}$F-pyridine prosthetic group with the following structure b

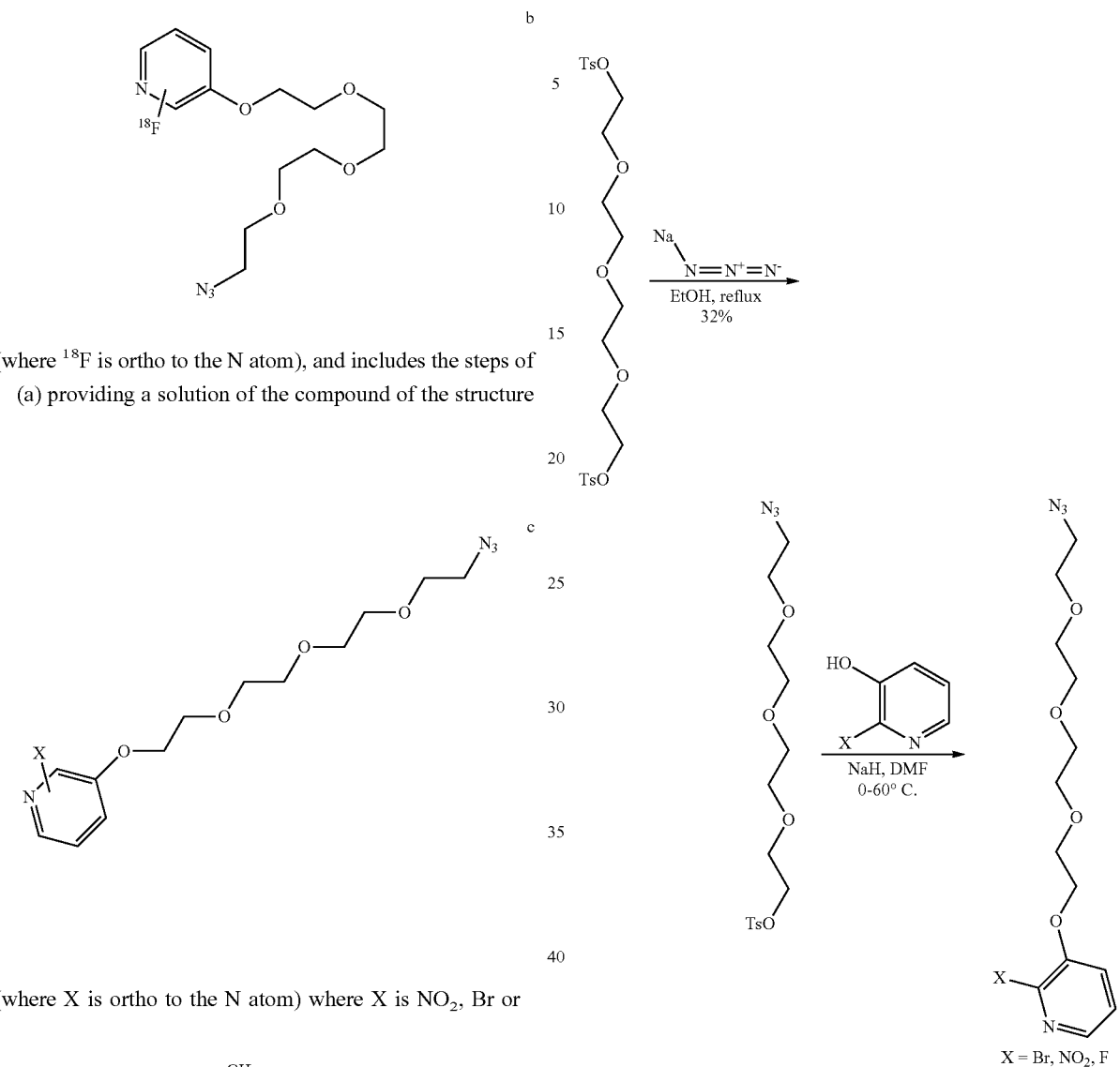

(where $^{18}$F is ortho to the N atom), and includes the steps of
(a) providing a solution of the compound of the structure (where X is ortho to the N atom) where X is NO$_2$, Br or (b) providing a mixture of $^{18}$F in $^{18}$O water, 4,7,13,16,21,24-hexaoxa-1,10-diazabicyclo[8.8.8]hexacosane and weak base, such as K$_2$CO$_3$;
(c) drying the mixture from step (b) to form a solid; and
(d) reacting the solution from step (a) with the solid from step (c) to form the $^{18}$F-labeled compound.

In certain embodiments, the method further comprises the step of producing a compound with the following structure a according to the Scheme I shown below:

In certain embodiments, the method comprises producing the $^{18}$F-pyridine prosthetic group [$^{18}$F]-3-(2-(2-(2-(2-azido-ethoxy)ethoxy)ethoxy)ethoxy)-2-fluoropyridine ($^{18}$F-FPPEGA), e, from d, according to the following reaction conditions:

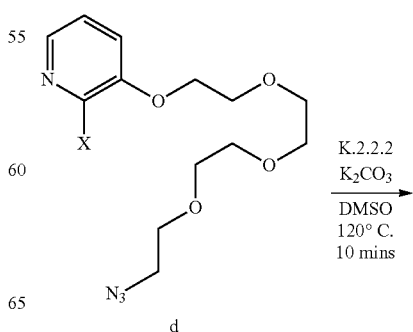

-continued

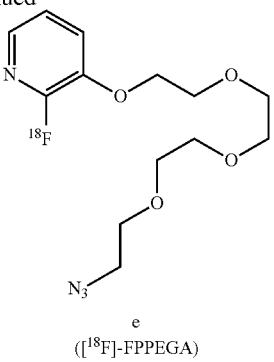

e
([$^{18}$F]-FPPEGA)

II. $^{18}$F-Radiolabeled Biological Probes

In certain aspects, provided herein are $^{18}$F-radiolabeled probes or agents with the following structure,

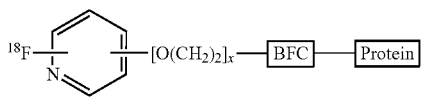

wherein x is an integer from 1 to 8. In some embodiments, x is an integer from 2 to 6. In some embodiments x is an integer from 3 to 5. In some embodiments, x is 4.

BFC

Bifunctional chelators or conjugating (BFC) moieties, which can be used in the radiolabeled compositions disclosed herein, are commercially available (e.g., Sigma Aldrich; Click Chemistry Tools), or may be synthesized according to well-known chemical reactions.

In certain embodiments, the BFC is selected from cyclooctyne based agents (e.g., DBCO, DIBO), DFO, DOTA and its derivatives (CB-DO2A, 3p-C-DEPA, TCMC, Oxo-DO3A), TE2A, CB-TE2A, CB-TE1A1P, CB-TE2P, MM-TE2A, DM-TE2A, diamsar and derivatives, NODASA, NODAGA, NOTA, NETA, TACN-TM, DTPA, 1B4M-DTPA, CHX-A"-DTPA, TRAP (PRP9), NOPO, AAZTA and derivatives (DATA), H$_2$dedpa, H$_4$octapa, H$_2$azapa, H$_5$decapa, H$_6$phospa, HBED, SHBED, BPCA, CP256, PCTA, HEHA, PEPA, EDTA, TETA, and TRITA based chelating agents, and close analogs and derivatives thereof. Suitable combinations of chelating agents and radionuclides are extensively described in Price et al., *Chem Soc Rev* 2014; 43:260-90.

In certain embodiments, the BFC is a cyclooctyne comprising a reactive group that forms a covalent bond with an amine, carboxyl, carbonyl or thiol functional group on the targeting protein or peptide. Reactive groups on the cyclooctyne include esters, acids, hydroxyl groups, aminooxy groups, maliemides, α-halogenketones and α-halogenacetamides.

In certain embodiments, the BFC is a cyclooctyne, such as dibenzocyclooctyne (DIBO), biarylazacyclooctynone (BARAC), dimethoxyazacyclooctyne (DIMAC) and dibenzocyclooctyne (DBCO). In certain embodiments, the cyclootyne is DBCO.

In certain embodiments, the cyclooctyne comprises a hydrophilic polyethylene glycol (PEG)$_y$ spacer arm, wherein y is an integer from 1 to 8. In certain embodiments, y is an integer from 2 to 6. In certain embodiments, y is 4 or 5.

In certain embodiments, the BFC is DBCO-PEG4-NHS-Ester or DBCO-Sulfo-NHS-Ester which react specifically and efficiently with a primary amine (e.g., side chain of lysine residues or aminosilane-coated surfaces). In certain embodiments, the BFC is DBCO-PEG4-Acid with terminal carboxylic acid (—COOH) that can be reacted with primary or secondary amine groups in the presence activators (e.g. EDC) forming a stable amide bond. In certain embodiments, the BFC is DBCO-PEG4-Amine which reacts with carboxyl groups in the presence of activators (e.g. EDC, or DCC) or with activated esters (e.g. NHS esters) forming stable amide bonds.

In certain embodiments, the BFC is DBCO-PEG4-Maleimide which reacts with sulfhydryl groups on cysteine residues, e.g., cysteine residues near the C-terminus of the polypeptide.

In certain embodiments, for labeling a protein, the protein is first modified to incorporate a cysteine for attaching the prosthetic group. For example, a cysteine may be added to the C-terminus of the protein. In certain embodiments, PxCy, wherein P is proline, C is cysteine, x is an integer that is at least 0 (e.g., 0, 1 or 2) and y is an integer that is at least 1, is added to the C-terminus of the protein. Methods for making modifications to proteins are well-known in the art.

In certain embodiments, the $^{18}$F-radiolabeled probe or agent has the following structure a,

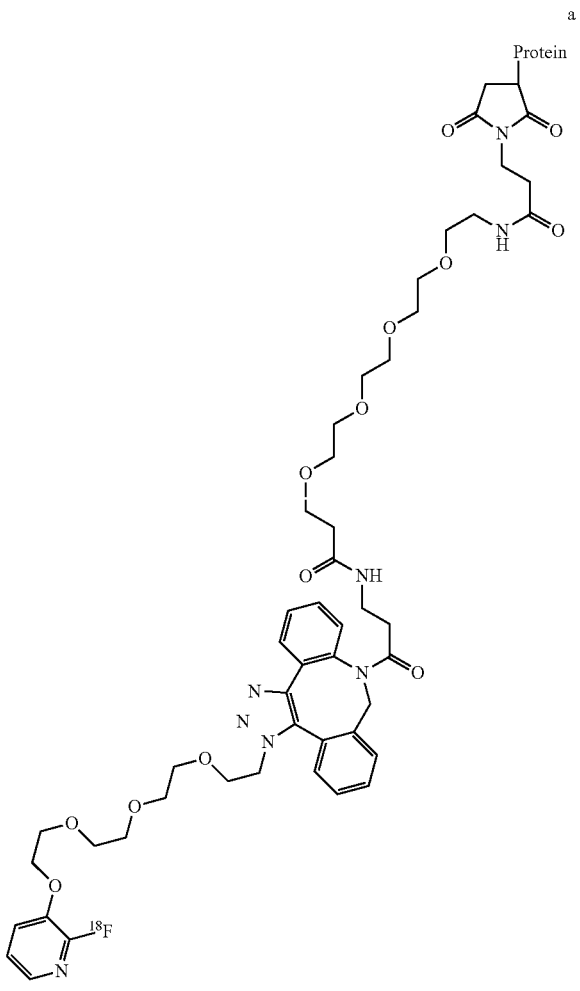

a wherein, the BFC is conjugated to the protein at a cysteine residue.

The $^{18}$F-radiolabeled targeting agents described herein may be produced using bioorthogonal, metal free click chemistry in medium suitable for direct use in vivo (e.g., saline) according to the procedures described herein.

III. Protein/Peptide Targeting Molecules

The $^{18}$F-prosthetic groups provided herein may be attached to virtually any targeting molecule, so long as it contains a derivatizable group that may be modified without affecting the interaction between the targeting molecule and the in vivo biological target (e.g., cell or tissue).

In some embodiments, the targeting molecule is a peptide (e.g., 2-5, 2-10, 2-20, 2-50 or 2-100 amino acid residues long) or protein, including, but not limited to, antibodies, antibody fragments, fibronectin based molecules and ligands (e.g., hormones, growth factors, cytokines, chemokines, interleukins and angiogenic factors). In some embodiments, the targeting molecule will comprise one or more binding sites for a target, e.g., associated with a disease or condition, such as a tumor associated or autoimmune antigen, or a protein displayed by a pathogenic organism such as a virus, bacterium, fungus or protozoan.

In some embodiments, the $^{18}$F-labeled peptides or protein may be selected to bind directly to a targeted cell, tissue, pathogenic organism or other target for imaging and/or detection. In other embodiments, $^{18}$F labeled protein or peptide may be selected to bind directly or indirectly to the in vivo target molecule. For example, a first protein or peptide may administered to the subject, followed by a second $^{18}$F-labeled molecule which binds to the first.

Exemplary proteins for use in the radiolabeled probes described herein include any known antibody or fragment or derivative thereof or alternative scaffold protein, such as Adnectins, or peptide or protein that specifically binds to a target, and does not significantly cross-react with unrelated targets.

In preferred embodiments, the targeting molecule, e.g., $^{18}$F-[targeting protein]-4PEG-DBCO-FPPEGA has a half-life, e.g., in blood or serum, of 30 minutes to 3 hours, 30 minutes to 120 minutes, 60 minutes to 120 minutes or 80 minutes to 100 minutes. In certain embodiments, the half-life of the targeting molecule is about the same as that of $^{18}$F, about 110 minutes.

Peptides

Peptides having as few as two amino acid residues, preferably two to ten residues, may be used and may also be coupled to other moieties. The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

In some embodiments, peptides which may be used include ligands, peptide vaccines, and epitopes. The peptides used as targetable constructs are conveniently synthesized on an automated peptide synthesizer using a solid-phase support and standard techniques of repetitive orthogonal deprotection and coupling. N-terminal residues may be acetylated to increase serum stability. Such protecting groups will be known to the skilled artisan. See Greene and Wuts Protective Groups in Organic Synthesis, 1999 (John Wiley and Sons, N.Y.).

Antibodies

In certain embodiments, the targeting molecule used in the radiotracer composition described herein is an antibody. The term "antibody" as used to herein may include whole antibodies and any antigen binding fragments (i.e., "antigen-binding portions") or single chains thereof. By way of example "antibody" may refer to both naturally occurring and non-naturally occurring antibodies; monoclonal and polyclonal antibodies; chimeric and humanized antibodies; human and nonhuman antibodies; bispecific antibodies; wholly synthetic antibodies; and single chain antibodies, and antigen-binding fragments of any of these, e.g., as further described herein. As used herein, the term "antigen" refers to any natural or synthetic immunogenic substance, such as a protein, peptide, or hapten.

The targeting molecules described herein may incorporate any antibody or fragment known in the art that has binding specificity for a target antigen, e.g., associated with a disease state or condition. Antibodies useful as targeting molecules may be commercially obtained from a wide variety of sources (e.g., ATTC, Manassas, Va.), and/or have published variable region sequences which may be produced according to art recognized recombinant techniques. In some embodiments, exemplary antibodies for use in the present methods include an anti-CTLA-4 antibody, an anti-PD-1 antibody, an anti-PDL-1 antibody, an anti-OX40 (also known as CD134, TNFRSF4, ACT35 and/or TXGP1L) antibody, or an anti-LAG-3 antibody or an antigen binding portion of any of these antibodies.

Antibodies used in the compositions and methods described herein can be produced using a variety of known techniques. Immunization protocols and techniques for isolation of immunized splenocytes are well established in the art. The production of monoclonal antibodies using the standard somatic cell hybridization technique described by Kohler and Milstein, Nature 256: 495 (1975), as well as viral or oncogenic transformation of B lymphocytes, phage display technique using libraries of human antibody genes are also routine. In addition, standard methodologies for the production of chimeric and humanized antibodies are readily available (see e.g., U.S. Pat. No. 4,816,567 to Cabilly et al.; U.S. Pat. No. 5,225,539 to Winter, and U.S. Pat. Nos. 5,530,101; 5,585,089; 5,693,762 and 6,180,370 to Queen et al.).

In certain embodiments, the targeting molecule used in the radiotracer composition is an antigen binding fragment. In order for the radiotracer to be effective for imaging, the biologic providing the molecular target specificity would need to have a plasma half-life compatible with the half-life of $^{18}$F. Thus, smaller proteins, e.g., antigen-binding fragments of antibodies or portions or derivatives of antigen binding fragments, are preferred. As used herein, the term "antigen-binding portion" or "antigen-binding fragment" of an antibody refers to one or more fragments of an antibody that retains the ability to specifically bind to an antigen. Examples of binding fragments encompassed within the term "antigen-binding portion" of an antibody include (i) a Fab fragment, a monovalent fragment consisting of the $V_L$, $V_H$, CL and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR), (vii) a combination of two or more isolated CDRs which may optionally be joined by a synthetic linker, and (viii) non CDR antigen binding portions of antibodies, e.g., Fcabs (see, e.g., WO009/132876). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see e.g., Bird et al. (1988) *Science* 242:423-426; and Huston et al. (1988) *Proc. Natl. Acad. Sci. USA* 85:5879-5883). Such single chain antibodies, domain antibodies, single-chain variable fragments, Fcab fragments, Fcabs and Fab fragments are intended to be encompassed within the term "antigen-binding portion" of an antibody. These and other potential constructs are described at Chan & Carter (2010) *Nat. Rev. Immunol.* 10:301. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

In certain embodiments, the antibody or antigen binding fragment used in the imaging agent is modified to modulate, e.g., decrease the half-life of the antibody or rapid clearance for use in the medical imaging methods described herein. Modifications such as I253A (Hornick et al. (2000) *J. Nucl. Med.* 41:355) and H435A/R I253A or H310A (Kim et al. (2000) *Eur. J. Immunol.* 29:2819) in Fc of human IgG1 can decrease FcRn binding. See also Kenanova et al. (2005) *Cancer Res.* 65:622. Other means to enhance clearance include formatting the antigen binding domains of the present invention as antibody fragments lacking the ability to bind FcRn, such as Fab fragments. Such modification can reduce the circulating half-life of an antibody from a couple of weeks to a matter of hours. Selective PEGylation of antibody fragments can then be used to fine-tune (increase in increments) the half-life of the antibody fragments if necessary. Chapman et al. (1999) *Nat. Biotechnol.* 17:780.

Radiotracer compositions containing an antibody or antigen binding fragment thereof can be assayed for retention of binding specificity in vitro and/or in vivo. Methods for analyzing binding affinity, cross-reactivity, and binding kinetics of various antibody compositions include standard assays known in the art, for example, ELISA, Western Blotting, flow cytometry, and BIACORE® surface plasmon resonance (SPR) analysis using a BIACORE® 2000 SPR instrument (Biacore AB, Uppsala, Sweden).

Fibronectin Based Protein (FBS)

In some embodiments, the targeting molecule used in the radiotracer compositions described herein is a FBS protein. Generally, FBS protein molecules have inherently rapid blood clearance rates, which can be advantageous for use with $^{18}F$ in imaging technologies by minimizing the amount of time needed for background probe signals from non-relevant tissue. Rapid clearing probers allow high contrast images to be collected the same day the probe is injected, and very importantly, can also serve to reduce overall radiation exposure to the subject.

As used herein, a "fibronectin based scaffold" or "FBS" protein or moiety refers to proteins or moieties that are based on a fibronectin type III ("Fn3") repeat. Fn3 is a small (about 10 kDa) domain that has the structure of an immunoglobulin (Ig) fold (i.e., an Ig-like β-sandwich structure, consisting of seven β-strands and six loops). Fibronectin has 18 Fn3 repeats, and while the sequence homology between the repeats is low, they all share a high similarity in tertiary structure. Fn3 domains are also present in many proteins other than fibronectin, such as adhesion molecules, cell surface molecules, e.g., cytokine receptors, and carbohydrate binding domains. For reviews see Bork et al., *Proc. Natl. Acad. Sci. USA,* 89(19):8990-8994 (1992); Bork et al., *J. Mol. Biol.,* 242(4):309-320 (1994); Campbell et al., *Structure,* 2(5):333-337 (1994); Harpez et al., *J. Mol. Biol.,* 238(4):528-539 (1994)). The term "FBS" protein or moiety is intended to include scaffolds based on Fn3 domains from these other proteins (i.e., non fibronectin molecules).

An Fn3 domain is small, monomeric, soluble, and stable. It lacks disulfide bonds and, therefore, is stable under reducing conditions. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole"). There are at least 15 different Fn3 modules in human Fibronectin, and while the sequence homology between the modules is low, they all share a high similarity in tertiary structure.

The loops in Fn3 molecules are structurally similar to complementary determining regions (CDRs) of antibodies, and when altered, may be involved in binding of the Fn3 molecule to a target, e.g., a target protein. Other regions of Fn3 molecules, such as the beta or beta-like strands and N-terminal or C-terminal regions, when altered, may also be involved in binding to a target. Any or all of loops AB, BC, CD, DE, EF and FG may participate in binding to a target. Any of the beta or beta-like strands may be involved in binding to a target. Fn3 domains may also bind to a target through one or more loops and one or more beta or beta-like strands. Binding may also require the N-terminal or C-terminal regions. An FBS domain for use in a protein may comprise all loops, all beta or beta-like strands, or only a portion of them, wherein certain loops and/or beta or beta-like strands and/or N- or C-terminal regions are modified (or altered), provided that the FBS domain preferably binds specifically to a target. For example, an FBS domain may comprise 1, 2, 3, 4, 5 or 6 loops, 1, 2, 3, 4, 5, 6, 7, or 8 beta strands, and optionally an N-terminal and/or C-terminal region, wherein one or more loops, one or more beta strands, the N-terminal region and/or the C-terminal regions are modified relative to the wild-type FBS domain.

An example of FBS proteins that are based on human $^{10}Fn3$ domains are adnectins (Adnexus, a wholly owned subsidiary of Bristol-Myers Squibb). Adnectins are human $^{10}Fn3$ molecules in which CDR-like loop regions, β-strands, N-terminal and/or C-terminal regions of a $^{10}Fn3$ domain has been modified to evolve a protein capable of binding to a compound of interest. For example, U.S. Pat. No. 7,115,396 describes $^{10}Fn3$ domain proteins wherein alterations to the BC, DE, and FG loops result in high affinity TNFα binders. U.S. Pat. No. 7,858,739 describes Fn3 domain proteins wherein alterations to the BC, DE, and FG loops result in high affinity VEGFR2 binders.

Imaging agents comprising Adnectins binding specifically to a target and comprising an Fn3 domain in which one or more of the solvent accessible loops and/or beta strands has been randomized or mutated. In certain embodiments, the Fn3 domain is an Fn3 domain derived from the wild-type tenth module of the human fibronectin type III domain ($^{10}Fn3$):

(SEQ ID NO: 3)
VSDVPRDLEVVAATPTSLLISWDAPAVTVRYYRITYGETGGNSPVQEFTV

PGSKSTATISGLKPGVDYTITVYAVTGRGDSPASSKPISINYRT (94 amino acids; AB, CD, and EF loops are underlined; the core $^{10}$Fn3 domain begins with amino acid 9 ("E") and ends with amino acid 94 ("T") and corresponds to an 86 amino acid polypeptide). The core wild-type human $^{10}$Fn3 domain is set forth in SEQ ID NO: 4.

Exemplary imaging agents comprise a $^{10}$Fn3 polypeptide that is at least 40%, 50%, 60%, 65%, 70%, 75%, 80%, 85%, or 90% identical to the human $^{10}$Fn3 domain, shown in SEQ ID NO: 3, or its core sequence, as shown in SEQ ID NO: 4. Much of the variability will generally occur in one or more of the loops or one or more of the beta strands or N- or C-terminal regions. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO: 3 or 4, provided that such variation does not disrupt the stability of the polypeptide in physiological conditions.

In certain embodiments, the invention provides an anti-[human target] Adnectin comprising a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain. In some embodiments, Adnectins comprise a $^{10}$Fn3 domain comprising an amino acid sequence at least 80%, 85%, 90%, 95%, 98%, 99% or 100% identical to the non-loop regions of SEQ ID NO: 3 or 4, wherein at least one loop selected from BC, DE, and FG is altered. In certain embodiments, the BC and FG loops are altered, in certain embodiments, the BC and DE loops are altered, in certain embodiments, the DE and FG loops are altered, and in certain embodiments, the BC, DE, and FG loops are altered, i.e., the $^{10}$Fn3 domains comprise non-naturally occurring loops. In certain embodiments, the AB, CD and/or the EF loops are altered. By "altered" is meant one or more amino acid sequence alterations relative to a template sequence (corresponding human fibronectin domain) and includes amino acid additions, deletions, substitutions or a combination thereof. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In exemplary embodiments, an $^{18}$F labeled Adnectin imaging agent binding specifically to a human target molecule comprises an alternative N-terminal region having from 1-20, 1-15, 1-10, 1-8, 1-5, 1-4, 1-3, 1-2, or 1 amino acids in length can be added to the N-terminal region of SEQ ID NO: 3 or 4. Exemplary alternative N-terminal regions include (represented by the single letter amino acid code) M, MG, G, MGVSDVPRDL and GVSDVPRDL. Other suitable alternative N-terminal regions, which may be linked, e.g., to the N-terminus of an adnectin core sequence, include, for example, $X_n$SDVPRDL, $X_n$DVPRDL, $X_n$VPRDL, $X_n$PRDL, $X_n$RDL, $X_n$DL, or $X_n$L, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus. In some embodiments, the alternative N-terminal region comprises the amino acid sequence MASTSG.

In exemplary embodiments, an $^{18}$F labeled Adnectin imaging agent binding specifically to a human target molecule comprises an alternative C-terminal region having from 1-20, 1-15, 1-10, 1-8, 1-5, 1-4, 1-3, 1-2, or 1 amino acids in length can be added to the C-terminal region of SEQ ID NO: 3 or 4. Specific examples of alternative C-terminal region sequences include, for example, polypeptides comprising, consisting essentially of, or consisting of, EIEK, EGSGC, EIEKPCQ, EIEKPSQ, EIEKP, EIEKPS, or EIEKPC. In some embodiments, the alternative C-terminal region comprises EIDK, and in particular embodiments, the alternative C-terminal region is either EIDKPCQ or EIDKPSQ.

In certain embodiments, an $^{18}$F labeled Adnectin imaging agent binding specifically to a human target molecule comprises an alternative C-terminal moiety, which can be linked to the C-terminal amino acids RT (i.e., amino acid 94) and comprises the amino acids $P_mX_n$, wherein P is proline, X is any amino acid, m is an integer that is at least 1 and n is 0 or an integer that is at least 1. A cysteine is useful for linking the $^{18}$F prosthetic group. In certain embodiments, the alternative C-terminal moiety comprises the amino acids PC. In certain embodiments, the alternative C-terminal moiety comprises the amino acids PI, PC, PID, PIE, PIDK, PIEK, PIDKP, PIEKP, PIDKPS, PIEKPS, PIDKPC, PIEKPC, PIDKPSQ, PIEKPSQ, PIDKPCQ, or PIEKPCQ. An exemplary Adnectin having PC at its C-terminus is provided in the Examples.

In certain embodiments, an FBS moiety is based on an Fn3 repeat other than the 10$^{th}$ repeat of the type III domain of fibronectin, e.g., human fibronectin. For example, an FBS moiety may be similar to any of the other fibronectin type III repeats, e.g., the 1$^{st}$, 2$^{nd}$, 3$^{rd}$, 4$^{th}$, 5$^{th}$ 6$^{th}$, 7$^{th}$ 8$^{th}$, 9$^{th}$, 11$^{th}$, 12$^{th}$, 13$^{th}$, 14$^{th}$, 15$^{th}$, 16$^{th}$, 17$^{th}$, and 18$^{th}$ Fn3 repeats. In yet other embodiments, an FBS moiety may be from a molecule other than fibronectin. Exemplary FBS moieties may be derived from tenascin, a protein that is composed of 15 Fn3 domains with similar sequence similarities to one another as found in fibronectin. These repeats are described, e.g., in Jacobs et al., *Protein Engineering, Design & Selection*, 25:107 (2012). Based on the homology of the repeats in the fibronectin molecule and those in the tenascin molecule, artificial molecules based on these homologies have been created. Proteins comprising a consensus amino acid sequence based on the homology of the domains in the fibronectin molecule are referred to as Fibcon and FibconB (WO 2010/093627 and Jacobs et al. (2012) supra.) and those based on the homology of the domains in the tenascin molecule are referred to as Tencon (WO 2010/051274, WO 2010/051310 and WO 2011/137319, which are specifically incorporated by reference herein). A Fibcon, FibconB or Tencon moiety, or target binding variants thereof, whether by itself or linked to a heterologous moiety may be fused as described herein. Fn3 domains from other proteins, e.g., cell surface hormone and cytokine receptors, chaperonins, and carbohydrate-binding domains, may be conjugated as described herein.

FBS proteins specific for any desired target molecule can be generated and tested using art recognized methods. Methods for testing the binding properties of FBS proteins are also well-known. For example, one way to rapidly make and test Fn3 domains with specific binding properties is the nucleic acid-protein fusion technology of Adnexus, a Bristol-Myers Squibb R&D Company. This disclosure utilizes the in vitro expression and tagging technology, termed 'PROfusion' which exploits nucleic acid-protein fusions (RNA- and DNA-protein fusions) to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558, 6,261,804, 6,214,553, 6,281,344, 6,207,446, 6,518,018 and 6,818,418; Roberts et al., *Proc. Natl. Acad. Sci.,* 1997; 94:12297-12302; and Kurz et al., *Molecules,* 2000; 5:1259-64, all of which are herein incorporated by reference.

Exemplary FBS proteins or moieties include, but are not limited to those which bind to mesothelian, glypican, TL1A, CD8, myostatin, LPA1 receptors, TNF-alpha, VEGFR2, PCSK9, IL-23, EGFR or IGF1R and those which are described, e.g., in WO 2010/093627, WO 2011/130324, WO 2009/083804, WO 2009/133208, WO 02/04523, WO 2012/016245, WO 2009/023184, WO 2010/051310, WO 2011/020033, WO 2011/051333, WO 2011/051466, WO 2011/092233, WO 2011/100700, WO 2011/130324, WO 2011/130328, WO 2011/137319, WO 2010/051274, WO 2009/086116, WO 09/058379, WO2013/067029 and WO2012/016245 (all of which are specifically incorporated by reference herein): any of the FBS proteins or moieties described in these publications may be used as described herein.

In some embodiments, the FBS protein binds to PD-L1. In some embodiments, the FBS protein comprises the amino acid sequence of SEQ ID NO: 1 or SEQ ID NO: 2. These molecules are also described in PCT/US 15/62485 and PCT/US 15/62502, both of which are specifically incorporated by reference herein for all its teachings.

In certain embodiments, an imaging agent, e.g., comprising an FBS protein, is linked to a moiety that modulates, e.g., increases, its blood PK by small increments to enhance the imaging contrast or increase avidity of the $^{18}$F-labeled targeting agent. In some embodiments, the clearance rate of the polypeptide in a mammal (e.g., mouse, rat, or human) is, or is increased by greater than two-fold, greater than three-fold, greater than four-fold or greater than five-fold relative to the unmodified FBS protein. Moieties that slow clearance of a protein from the blood, herein referred to as "PK moieties", include polyoxyalkylene moieties (e.g., polyethylene glycol), sugars (e.g., sialic acid), and well-tolerated protein moieties (e.g., Fc and fragments and variants thereof, transferrin, or serum albumin). The FBS protein may also be fused to albumin or a fragment (portion) or variant of albumin as described in U.S. Publication No. 2007/0048282, or may be fused to one or more serum albumin binding FBS proteins, as described herein.

Other PK moieties that can be used in the invention include those described in Kontermann et al., (*Current Opinion in Biotechnology* 2011; 22:868-76), herein incorporated by reference. Such PK moieties include, but are not limited to, human serum albumin fusions, human serum albumin conjugates, human serum albumin binders (e.g., Adnectin PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

In some embodiments, the invention provides $^{18}$F-labeled FBS proteins fused to a PK moiety that is a polymeric sugar. In some embodiments, the PK moiety is a polyethylene glycol moiety. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

The term "PEG" is used broadly to encompass any polyethylene glycol molecule, without regard to size or to modification at an end of the PEG, and can be represented by the formula: $X-O(CH_2CH_2O)_{n-1}CH_2CH_2OH$, where n is 2 or more, e.g., 20 to 2300 and X is H or a terminal modification, e.g., a $C_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs. Branched PEGs are described in, for example, European Published Application No. 473084A and U.S. Pat. No. 5,932,462.

One or more PEG molecules may be attached at different positions on the protein, and such attachment may be achieved by reaction with amines, thiols or other suitable reactive groups. The amine moiety may be, for example, a primary amine found at the N-terminus of a polypeptide or an amine group present in an amino acid, such as lysine or arginine. In some embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus.

PEGylation may be achieved by site-directed PEGylation, wherein a suitable reactive group is introduced into the protein to create a site where PEGylation preferentially occurs. In some embodiments, the protein is modified to introduce a cysteine residue at a desired position, permitting site-directed PEGylation on the cysteine. Mutations may be introduced into a protein coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein.

Alternatively, surface residues may be predicted by comparing the amino acid sequences of binding polypeptides, given that the crystal structure of the framework, based on which binding polypeptides are designed and evolved, has been solved (see Himanen et al., *Nature* 2001; 414:933-8) and thus the surface-exposed residues identified. PEGylation of cysteine residues may be carried out using, for example, PEG-maleimide, PEG-vinylsulfone, PEG-iodoacetamide, or PEG-orthopyridyl disulfide.

The PEG is typically activated with a suitable activating group appropriate for coupling to a desired site on the polypeptide. PEGylation methods are well-known in the art and further described in Zalipsky, S., et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky (1995) *Advanced Drug Reviews* 16: 157-182.

PEG may vary widely in molecular weight and may be branched or linear. Typically, the weight-average molecular weight of PEG is from about 100 Daltons to about 150,000 Daltons. Exemplary weight-average molecular weights for PEG include about 1,000, Daltons, about 2,000 Daltons, about 5,000 Daltons, about 10,000, Daltons, about 20,000 Daltons, about 40,000 Daltons, about 60,000 Daltons and about 80,000 Daltons. In certain embodiments, the molecular weight of PEG is about 5,000 Daltons. Branched versions of PEG having a total molecular weight of any of the foregoing can also be used. In some embodiments, the PEG has two branches. In other embodiments, the PEG has four branches. In one embodiment, the PEG is a bis-PEG (NOF Corporation, DE-200MA).

Similar to antibodies, selective PEGylation of adnectins can be used to fine-tune (increase in increments) the half-life of the adnectins if necessary.

Conventional separation and purification techniques known in the art can be used to purify PEGylated FBS proteins, such as size exclusion (e.g., gel filtration) and ion exchange chromatography. Products may also be separated using SDS-PAGE. Products that may be separated include mono-, di-, tri-, poly- and un-PEGylated Adnectins, as well as free PEG. The percentage of mono-PEG conjugates can be controlled by pooling broader fractions around the elution peak to increase the percentage of mono-PEG in the composition. About 90% mono-PEG conjugates represent a good balance of yield and activity.

IV. Targets

Exemplary in vivo target molecules which bind the $^{18}$F-labeled probes described herein are those associated with various diseases or conditions, such as a malignant disease, a cardiovascular disease, an infectious disease, an inflammatory disease, an autoimmune disease, or a neurological disease. Target molecules may also be biomarkers for certain therapies, e.g., PD-L1.

Provided herein are $^{18}$F labeled imaging agents, e.g., [$^{18}$F]-moiety-4PEG-DBCO-FPPEGA, wherein the moiety binds specifically to a target molecule, such as a target protein on the surface of human cells. In certain embodiments, the moiety is a peptide; an antibody, or antigen binding portion thereof or a variant of an antibody; an alternative scaffold, such as an Fn3 (e.g., a human Fn3) domain, such as an FBS, e.g., a human $^{10}$Fn3 domain. In certain embodiments, the moiety binds to a cell surface molecule, e.g., a cell surface molecule on a tumor cell or a cell in the tumor, e.g., a tumor infiltrating lymphocyte that is located in the tumor. In certain embodiments, the moiety binds to a cell surface molecule on an immune cell, e.g., a T cell (e.g., a Treg cell), a Teff cell, a B cell, a macrophage, a dendritic cell, an NK cell or a Langerhans cell.

In certain embodiments, an $^{18}$F labeled imaging agent comprises a moiety that binds specifically to an immuno-oncology target (receptor or ligand), such as a co-stimulatory receptor on an immune cell (e.g., T cell or NK cell) or an inhibitor on an immune cell (e.g., a T cell or NK cell), which targets modulate immune responses. In one embodiment, the moiety binds to one of the following molecules or ligand or receptor thereof: an immunoglobulin super family (IgSF) member; a member of the B7 family, which includes B7-1, B7-2, B7-H1 (PD-L1), B7-DC (PD-L2), B7-H2 (ICOS-L), B7-H3, B7-H4, B7-H5 (VISTA), and B7-H6; a member of the TNF receptor superfamily or its ligand, e.g., CD40, CD40L, OX-40, OX-40L, CD70, CD27L, CD30, CD30L, 4-1BBL, CD137, GITR, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR (see, e.g., Tansey (2009) Drug Discovery Today 00:1); a protein that inhibits an immune cell (e.g., immune checkpoint inhibitors), such as CTLA-4, PD-1, PD-L1, PD-L2, and LAG-3, TIM-3, Galectin 9, CEACAM-1, BTLA, CD69, Galectin-1, TIGIT, CD113, GPR56, VISTA, 2B4, CD48, GARP, CD73, PD1H, LAIR1, TIM-1, TIM-4, CD39; a protein that stimulates an immune response, such as B7-1, B7-2, CD28, 4-1BB (CD137), 4-1BBL, GITR, GITRL, ICOS, ICOS-L, OX40, OX40L, CD70, CD27, CD40, DR3 and CD28H; any of the following cell surface molecules: KIR, cytokine or interleukin receptors, IL-6, IL-10, TGF-ß, VEGF, CSF-iR, CD25 and IDO.

In some embodiments, the targeting molecule binds to an antigen or receptor of a pathogen, including but not limited to fungi, viruses, parasites and bacteria. Examples of pathogenic viruses detectable by methods described herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus. Examples of bacteria and fungi include, *Streptococcus agalactiae, Legionella pneumophilia, Streptococcus pyogenes, Escherichia coli, Neisseria gonorrhoeae, Neisseria meningitidis, Pneumococcus, Hemophilis influenzae B, Treponema pallidum*, Lyme disease spirochetes, *Pseudomonas aeruginosa, Mycobacterium leprae, Brucella abortus, Mycobacterium tuberculosis* and *Chlostridium tetani. Some examples of pathogenic bacteria causing infections detectable by methods described herein include chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, and Lyme disease bacteria.*

Some examples of pathogenic fungi causing infections detectable by methods described herein include *Candida (albicans, krusei, glabrata, tropicalis*, etc.), *Cryptococcus neoformans, Aspergillus (fumigatus, niger*, etc.), Genus Mucorales (*mucor, absidia, rhizopus*), *Sporothrix schenkii, Blastomyces dermatitidis, Paracoccidioides brasiliensis, Coccidioides immitis* and *Histoplasma capsulatum.*

Some examples of pathogenic parasites causing infections detectable by methods described herein include *Entamoeba histolytica, Balantidium coli, Naegleriafowleri, Acan-*

*thamoeba* sp., *Giardia lambia*, *Cryptosporidium* sp., *Pneumocystis carinii*, *Plasmodium vivax*, *Babesia microti*, *Trypanosoma brucei*, *Trypanosoma cruzi*, *Leishmania donovani*, *Toxoplasma gondii*, *Nippostrongylus brasiliensis*.

V. Biophysical and Biochemical Characterization

Binding of the protein targeting molecules described herein to a target molecule may be assessed in terms of equilibrium constants (e.g., dissociation, $K_D$) and in terms of kinetic constants (e.g., on-rate constant, $k_{on}$ and off-rate constant, $k_{off}$). A protein targeting molecule will generally bind to a target molecule with a $K_D$ of less than 500 nM, 100 nM, 10 nM, 1 nM, 500 pM, 200 pM, or 100 pM, although higher $K_D$ values may be tolerated where the $k_{off}$ is sufficiently low or the $k_{on}$ is sufficiently high.

Exemplary assays for determining the binding affinity of a protein targeting molecule include, but are not limited to, solution phase methods such as the kinetic exclusion assay (KinExA) (Blake et al., *JBC* 1996; 2.71:27677-85; Drake et al., *Anal Biochem* 2004; 328:35-43), surface plasmon resonance (SPR) with the Biacore system (Uppsala, Sweden) (Welford et al., *Opt. Quant. Elect* 1991; 23:1; Morton and Myszka, *Methods in Enzymology* 1998; 295:268) and homogeneous time resolved fluorescence (HTRF) assays (Newton et al., *J Biomol Screen* 2008; 13:674-82; Patel et al., *Assay Drug Dev Technol* 2008; 6:55-68).

In certain embodiments, biomolecular interactions can be monitored in real time with the Biacore system, which uses SPR to detect changes in the resonance angle of light at the surface of a thin gold film on a glass support due to changes in the refractive index of the surface up to 300 nm away. Biacore analysis generates association rate constants, dissociation rate constants, equilibrium dissociation constants, and affinity constants. Binding affinity is obtained by assessing the association and dissociation rate constants using a Biacore surface plasmon resonance system (Biacore, Inc.). A biosensor chip is activated for covalent coupling of the target. The target is then diluted and injected over the chip to obtain a signal in response units of immobilized material. Since the signal in resonance units (RU) is proportional to the mass of immobilized material, this represents a range of immobilized target densities on the matrix. Association and dissociation data are fit simultaneously in a global analysis to solve the net rate expression for a 1:1 bimolecular interaction, yielding best fit values for $k_{on}$, $k_{off}$ and $R_{max}$ (maximal response at saturation). Equilibrium dissociation constants for binding. $K_D$'s are calculated from SPR measurements as $k_{off}/k_{on}$.

In some embodiments, the protein targeting molecules described herein exhibit a $K_D$ of binding to its target in the SPR affinity assay of 500 nM or less, 400 nM or less, 300 nM or less, 200 nM or less, 150 nM or less, 100 nM or less, 90 nrM or less, 80 nM or less, 70 nM or less, 60 nM or less, 50 nM or less, 40 nM or less, 30 nM or less, 20 nM or less, 15 nM or less, 10 nM or less, 5 nM or less, or 1 nM or less.

It should be understood that the assays described herein above are exemplary, and that any method known in the art for determining the binding affinity between proteins (e.g., fluorescence based-transfer (FRET), enzyme-linked immunosorbent assay, and competitive binding assays (e.g., radioimmunoassays)) can be used to assess the binding affinities of the protein targeting molecules described herein.

Protein Production

The targeting proteins described herein, e.g., peptides, antigen-binding fragments of antibodies and Adnectins may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. An exemplary N-terminal leader sequence for production of polypeptides in a mammalian system is: METDTLLL-WVLLLWVPGSTG, which is removed by the host cell following expression.

For prokaryotic host cells that do not recognize and process a native signal sequence, the signal sequence is substituted by a prokaryotic signal sequence selected, for example, from the group of the alkaline phosphatase, penicillinase, 1 pp, or heat-stable enterotoxin II leaders.

For yeast secretion the native signal sequence may be substituted by, e.g., a yeast invertase leader, a factor leader (including *Saccharomyces* and *Kluyveromyces* alpha-factor leaders), or acid phosphatase leader, the *C. albicans* glucoamylase leader, or the signal sequence described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein described herein, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein described herein. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding protein described herein by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein described herein. One useful transcription termination component is the bovine growth hormone polyadenylation region. See WO 94/11026 and the expression vector disclosed therein.

The recombinant DNA can also include any type of protein tag sequence that may be useful for purifying the protein. Examples of protein tags include, but are not limited to, a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York (1985)), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (Bio/Technology, 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides described herein would make expression in *E. coli* as the preferred method for expression. The protein is then purified from culture media or cell extracts.

Also described herein are cell lines that express a targeting protein, e.g., an Adnectin. Creation and isolation of cell lines producing a targeting protein can be accomplished using standard techniques known in the art, such as those described herein.

Host cells are transformed with the herein-described expression or cloning vectors for protein production and cultured in conventional nutrient media modified as appropriate for inducing promoters, selecting transformants, or amplifying the genes encoding the desired sequences.

Targeting proteins can also be obtained in aglycosylated form by producing them in, e.g., prokaryotic cells (e.g., *E. coli*). For example, aglycosylated forms of the Adnectins described herein exhibit the same affinity, potency, and mechanism of action as glycosylated Adnectins when tested in vitro.

The host cells used to produce the proteins of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma)) are suitable for culturing the host cells. In addition, many of the media described in Ham et al., Meth. Enzymol., 58:44 (1979), Barites et al., Anal. Biochem., 102:255 (1980), U.S. Pat. Nos. 4,767,704, 4,657,866, 4,927,762, 4,560,655, 5,122,469, 6,048,728, 5,672,502, or RE 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins described herein can also be produced using cell-free translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Proteins described herein can also be produced by chemical synthesis (e.g., by the methods described in Solid Phase Peptide Synthesis, 2nd Edition, The Pierce Chemical Co., Rockford, Ill. (1984)). Modifications to the protein can also be produced by chemical synthesis.

The proteins of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, or preferably at least 95% pure, and most preferably at least 98% pure. Regardless of the exact numerical value of the purity, the polypeptide is sufficiently pure for use as a pharmaceutical product.

VI. Formulations

Further provided are compositions, e.g., a pharmaceutical compositions, containing one or a combination of $^{18}$F-labeled targeting agents, described herein, formulated together with a pharmaceutically acceptable carrier. Such compositions may include one or a combination of (e.g., two or more different) agents described herein. For example, a pharmaceutical composition described herein can comprise a combination of $^{18}$F-labeled targeting agent and a drug.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, $^{18}$F-labeled targeting agent may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the $^{18}$F-labeled targeting agent in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of $^{18}$F-labeled targeting agent which can be combined with a carrier material to produce a single dosage form will vary depending upon the subject being treated, and the particular mode of administration. The amount of $^{18}$F-labeled targeting agent which can be combined with a carrier material to produce a single dosage form will generally be that amount of the composition which produces a detectable effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

VII. Administration and Imaging

The $^{18}$F-labeled targeting agents described herein are useful in a variety of in vivo imaging applications (e.g., for tissue or whole body imaging). In certain embodiments, the $^{18}$F-labeled targeting agent can be used to image target-positive cells or tissues, e.g., target expressing tumors. For example, the labeled $^{18}$F-labeled targeting agent is administered to a subject in an amount sufficient to uptake the $^{18}$F-labeled targeting agent into the tissue of interest. The subject is then imaged using an imaging system such as PET for an amount of time appropriate for the $^{18}$F radionuclide. The $^{18}$F-labeled targeting agent-bound to cells or tissues expressing the targeting agent are then detected by the imaging system.

PET imaging with an F labeled imaging agent, e.g., [$^{18}$F]-[targeting molecule]-4PEG-DBCO-FPPEGA, may be used to qualitatively or quantitatively detect the target molecule targeted by the targeting molecule. An imaging agent may be used as a biomarker, and the presence or absence of a positive signal (i.e., presence of the target molecule) in a subject may be indicative that, e.g., the subject would be responsive to a given therapy, e.g., a cancer therapy, or that the subject is responding or not to a therapy.

In certain embodiments, the progression or regression of disease (e.g., tumor) can be imaged as a function of time or treatment. For instance, the size of the tumor can be monitored in a subject undergoing cancer therapy (e.g., chemotherapy, radiotherapy) and the extent of regression of the tumor can be monitored in real-time based on detection of the $^{18}$F labeled imaging, e.g., [$^{18}$F]-[targeting molecule]-4PEG-DBCO-FPPEGA. The distribution of target molecule within one or more tumors or healthy cells may also be visualized, and monitored prior and/or during a treatment and/or a disease.

In certain embodiments, imaging of tissues expressing the target is effected before, during, and after administration of the labeled anti-target imaging agent, such as [$^{18}$F]-[targeting molecule]-4PEG-DBCO-FPPEGA to a subject.

In certain embodiments, the subject receiving an imaging agent, e.g., PD-L1 imaging agent, is a mammal, for example, a human, dog, cat, ape, monkey, rat, or mouse.

In certain embodiments, the imaging agents described herein are useful for PET imaging of lungs, heart, kidneys, liver, and skin, and other organs, or tumors associated with these organs which express the target molecule.

In certain embodiments, the imaging agents, such as [$^{18}$F]-[targeting molecule]-4PEG-DBCO-FPPEGA imaging agents, provide a contrast of at least 50%, 75%, 2, 3, 4, 5 or more. The Examples show that the anti-PD-L1 Adnectins that were used provided a PET contrast of 2 or more, and that the affinity of the Adnectins was less important.

The imaging agents, e.g., [$^{18}$F]-[targeting molecule]-4PEG-DBCO-FPPEGA imaging agents that bind specifically given targets, are preferably administered intravenously, e.g., as a bolus injection.

In certain embodiments, the imaging agents described herein, e.g., [$^{18}$F]-[targeting molecule]-4PEG-DBCO-FPPEGA imaging agents, are used to detect target positive cells in a subject by administering to the subject an imaging agent disclosed herein, and detecting the imaging agent, the detected imaging agent defining the location of the target positive cells in the subject. In certain embodiments, the imaging agent is detected by positron emission tomography.

In certain embodiments, the imaging agents described herein, e.g., [$^{18}$F]-[targeting molecule]-4PEG-DBCO-FPPEGA imaging agents, are used to detect target expressing tumors in a subject by administering to the subject the imaging agent disclosed herein, and detecting the imaging agent, the detected imaging agent defining the location of the tumor in the subject. In certain embodiments, the imaging agent is detected by positron emission tomography.

In certain embodiments, an image of an imaging agent described herein, e.g., [$^{18}$F]-[targeting molecule]-4PEG-DBCO-FPPEGA imaging agents, is obtained by administering the imaging agent to a subject and imaging in vivo the distribution of the imaging agent by positron emission tomography.

Disclosed herein are methods of obtaining a quantitative image of tissues or cells expressing a target, the method comprising contacting the cells or tissue with an anti-target imaging agent, e.g., [$^{18}$F]-[targeting molecule]-4PEG-DBCO-FPPEGA imaging agents, and detecting or quantifying the tissue expressing the target using positron emission tomography.

Also disclosed herein are methods of detecting a target-expressing tumor comprising administering an imaging-effective amount of an anti-target imaging agent, e.g., [$^{18}$F]-[targeting molecule]-4PEG-DBCO-FPPEGA imaging agent, to a subject having a target-expressing tumor, and detecting the radioactive emissions of said imaging agent in the tumor using positron emission tomography, wherein the radioactive emissions are detected in the tumor.

Also disclosed herein are methods of diagnosing the presence of a target-expressing tumor in a subject, the method comprising
  (a) administering to a subject in need thereof an anti-target imaging agent described herein, e.g., [$^{18}$F]-[targeting molecule]-4PEG-DBCO-FPPEGA imaging agents; and
  (b) obtaining a radio-image of at least a portion of the subject to detect the presence or absence of the imaging agent;
wherein the presence and location of the imaging agent above background is indicative of the presence and location of the target-expressing tumor.

Also disclosed are methods for predicting whether a subject will respond to a therapy, wherein a response to therapy depends on the presence of certain levels of a target protein in a tissue, e.g., a tumor. For example, a method may comprise (a) administering to a subject in need thereof an anti-target imaging agent described herein, e.g., [$^{18}$F]-[targeting molecule]-4PEG-DBCO-FPPEGA imaging agents; and (b) obtaining a radio-image of at least a portion of the subject to detect the presence or absence of the imaging agent, wherein the presence of the target (or of certain levels of the target) indicates that the subject is likely to respond to a therapy.

In certain embodiments, a method comprises (a) administering to a subject having cancer an anti-target imaging agent, e.g., an anti-PD-L1 imaging agent, described herein, e.g., [$^{18}$F]-[targeting molecule]-4PEG-DBCO-FPPEGA imaging agents; and (b) obtaining a radio-image of at least a portion of the subject to detect the presence or absence of the imaging agent, wherein the presence of the target, e.g., PD-L1 (or of certain levels of the target) indicates that the subject is likely to respond to a cancer therapy.

Also provided herein are methods for determining whether a subject having cancer is likely to respond to an immunotherapy, e.g., with a PD-1 or PD-L1 antagonist, the method comprising (a) administering to the subject having cancer a PD-L1 imaging agent, e.g., described herein; and (b) obtaining an image (static or dynamic) of at least a portion of the subject after step (a), and if the subject has a level of PD-L1 in one tumor or across several tumors that is equal to or above that required for treatment with a PD-1 or PD-L1 antagonist (e.g., OPDIVO™, KEYTRUDA™ or TECENTRIQ™), then treating the subject with an anti-tumor therapy, e.g., a PD-1 or PD-L1 antagonist e.g., OPDIVO™, KEYTRUDA™ or TECENTRIQ™.

Also provided are methods of treating a subject having a disease with a therapy that requires the presence of certain levels of a target protein in a tissue, e.g., a tumor, comprising (a) administering to a subject in need thereof an imaging agent that detects a target protein, e.g., described herein, and obtaining an image (static or dynamic) of at least a portion of the subject to determine the presence of target protein in one or more tissues, e.g., tumors; and if the subject has a level of target protein in one tissue or across several tumors that is equal to or above that required for the treatment with the therapy, then, (a) administering to the therapy.

In certain embodiments, a method of treating a subject having cancer, comprises (a) administering to a subject in need thereof an imaging agent comprising a PD-L1 imaging agent, e.g., described herein, and obtaining an image (static or dynamic) of at least a portion of the subject to determine the presence of PD-L1 in one or more tumors; and if the subject has a level of PD-L1 in one tumor or across several tumors that is equal to or above that required for treatment with a PD-1 or PD-L1 antagonist (e.g., OPDIVO™, KEYTRUDA™ or TECENTRIQ™), then, (a) administering to the subject an anti-tumor therapy, e.g., an agent that inhibits the interaction between PD-1 and PD-L1 (a PD-1 or PD-L1 antagonist), e.g., OPDIVO™, KEYTRUDA™ or TECENTRIQ™.

Also disclosed herein are methods of monitoring the progress of an anti-tumor therapy against target-expressing tumors in a subject, the method comprising (a) administering to a subject in need thereof an anti-target imaging agent described herein, e.g., [$^{18}$F]-[targeting molecule]-4PEG-DBCO-FPPEGA imaging agent, at a first time point and obtaining an image of at least a portion of the subject to determine the size of the tumor;

(b) administering an anti-tumor therapy to the subject;

(c) administering to the subject the imaging agent at one or more subsequent time points and obtaining an image of at least a portion of the subject at each time point; wherein the dimension and location of the tumor at each time point is indicative of the progress of the disease.

PET Imaging

Typically, for imaging purposes it is desirable to provide the recipient with a dosage of protein or peptide that is in the range of from about 1 mg to 200 mg as a single intravenous infusion, although a lower or higher dosage also may be administered as circumstances dictate. Typically, it is desirable to provide the recipient with a dosage that is in the range of from about 0.1 mg to 10 mg per square meter of body surface area of the protein or peptide for the typical adult, although a lower or higher dosage also may be administered as circumstances dictate. Examples of dosages proteins or peptides that may be administered to a human subject for imaging purposes are about 0.1 to 200 mg, about 0.1 to 70 mg, about 0.1 to 20 mg, and about 0.1 to 10 mg, although higher or lower doses may be used.

Examples of dosages of imaging agents that may be administered to a human subject for imaging purposes are 10 μg to 1000 μg, 100 μg to 1000 μg, 100 μg to 500 μg, 200 μg to 500 μg, and 300 μg to 400 μg, although higher or lower doses may be used. For example, an $^{18}$F labeled anti-target Adnectin, e.g., [$^{18}$F]-[targeting molecule]-4PEG-DBCO-FPPEGA imaging agent may be administered in an amount, e.g., as a bolus injection, to a human ranging from 10 g to 1000 μg, 100 μg to 1000 μg, 100 μg to 500 μg, 200 μg to 500 μg, and 300 μg to 400 μg. In certain embodiments, an $^{18}$F labeled anti-target Adnectin, e.g., [$^{18}$F]-[targeting molecule]-4PEG-DBCO-FPPEGA imaging agent, is administered to a human subject in an amount of about 350 μg, which corresponds to about 4.4 μg/kg for an 80 kg subject.

In certain embodiments, administration occurs in an amount of radiolabeled imaging agent, e.g., [$^{18}$F]-[targeting molecule]-4PEG-DBCO-FPPEGA imaging agent, of between 0.005 μg/kg of body weight to 50 μg/kg of body weight per day, e.g., between 0.02 μg/kg of body weight to 10 μg/kg, e.g., per day, between 0.1 μg/kg of body weight to 10 μg/kg of body weight, e.g., per day, between 1 μg/kg of body weight to 10 μg/kg of body weight, e.g., per day, between 2 μg/kg of body weight to 6 μg/kg of body weight, e.g., per day or between 4 μg/kg of body weight to 5 μg/kg of body weight, e.g., per day. The mass associated with a PET tracer is in the form of the natural isotope (e.g., $^{19}$F for a $^{18}$F PET tracer). In certain embodiments, an $^{18}$F imaging agent, e.g., [$^{18}$F]-[targeting molecule]-4PEG-DBCO-FPPEGA imaging agent is administered to a human subject in an amount between 0.1p g/kg of body weight to 10 μg/kg of body weight, e.g., per day, between 1 μg/kg of body weight to 10 μg/kg of body weight, e.g., per day, between 2 μg/kg of body weight to 6 μg/kg of body weight, e.g., per day or between 4 μg/kg of body weight to 5 μg/kg of body weight, e.g., per day.

Dosage regimens are adjusted to provide the optimum detectable amount for obtaining a clear image of the tissue or cells which uptake the $^{18}$F-labeled targeting agent. It is especially advantageous to formulate parenteral compositions in dosage unit form for ease of administration and uniformity of dosage. Dosage unit form as used herein refers to physically discrete units suited as unitary dosages for the subjects to which the $^{18}$F-labeled targeting agent is to be administered. The specification for the dosage unit forms described herein are dictated by and directly dependent on (a) the unique characteristics of the targeting portion of the $^{18}$F-labeled targeting agent; (b) the tissue or cells to be targeted; (c) the limitations inherent in the imaging technology used.

For administration of an imaging agent, e.g., [$^{18}$F]-[targeting molecule]-4PEG-DBCO-FPPEGA imaging agent, the dosage used will depend upon the disease type, targeting compound used, the age, physical condition, and gender of the subject, the degree of the disease, the site to be examined, and others. In particular, sufficient care has to be taken about exposure doses to a subject. A saturating dose of $^{18}$F radiolabel may be administered to the patient. For example, the amount of radioactivity of the imaging agent, e.g., [$^{18}$F]-[targeting molecule]-4PEG-DBCO-FPPEGA imaging agent, may range from 3.7 megabecquerels (MBq) to 3.7 gigabecquerels (GBq), from 18 MBq to 740 MBq, from 100 MBq to 500 MBq, from 100 MBq to 400 MBq, from 100 MBq to 333 MBq, from 100 MBq to 250 MBq, from 150 MBq to 250 MBq, from 200 MBq to 250 MBq or from 200 MBq to 225 MBq. Alternatively, the dosage may be measured by millicuries, for example. In some embodiments, the amount of imaging agent, e.g., [$^{18}$F]-[targeting molecule]-4PEG-DBCO-FPPEGA imaging agent, administered for imaging studies is 1 to 10 mCi, 3 to 10 mCi, 3 to 8 mCi, 4 to 7 mCi or 5 to 6 mCi. In some embodiments, an effective amount will be the amount of compound sufficient to produce emissions in the range of from 1 to 10 mCi, 3 to 10 mCi, 3 to 8 mCi, 4 to 7 mCi or 5 to 6 mCi. In certain embodiments, an imaging agent, e.g., [$^{18}$F]-[targeting molecule]-4PEG-DBCO-FPPEGA imaging agent, is administered to a human subject in an amount of 1 to 10 mCi, 3 to 10 mCi, 3 to 8 mCi, 4 to 7 mCi or 5 to 6 mCi.

In certain embodiments, an imaging agent, e.g., [$^{18}$F]-[targeting molecule]-4PEG-DBCO-FPPEGA imaging agent, is administered as a composition comprising 1-5% of the $^{18}$F labeled imaging agent, e.g., [$^{18}$F]-[targeting molecule]-4PEG-DBCO-FPPEGA imaging agent, and 95-99%, respectively, of the non-radiolabeled precursor, e.g., [targeting molecule]-4PEG-DBCO. In certain embodiments, the ratio is 2% of the $^{18}$F labeled imaging agent, and 98% of the non-radiolabeled precursor. The ratio may vary, provided that, preferably, the total amount of protein administered to the subject for imaging remains a microdose, i.e., <30 nM.

Actual dosage levels of the active ingredients in the pharmaceutical compositions described herein may be varied so as to obtain an amount of the active ingredient which is effective to achieve the desired uptake of the $^{18}$F-labeled targeting agent in the cells or tissues of a particular patient, composition, and mode of administration, without being toxic to the patient. It will be understood, however, that the total daily usage of the $^{18}$F-labeled targeting agent of the present disclosure will be decided by the attending physician or other attending professional within the scope of sound medical judgment. The specific effective dose level for any particular subject will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; other drugs, compounds and/or materials used in combination with the particular compositions employed, the age, sex, weight, condition, general health and prior medical history of the patient being treated, and like factors well known in the medical arts. In certain embodiments, the amount of $^{18}$F-radiolabeled probe administered into a human subject required for imaging will be determined by the prescribing physician with the dosage generally varying according to the quantity of emission from the $^{18}$F-radionuclide.

In certain embodiments, the $^{18}$F-labeled targeting agent described herein can be formulated to ensure proper distribution in vivo. For example, the blood-brain barrier (BBB) excludes many highly hydrophilic compounds. Agents may cross the BBB by formulating them, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994).

Exemplary PET Procedure

The following illustrative procedure may be utilized when performing PET imaging studies on patients in the clinic. A venous catheter, e.g., a 20 G two-inch venous catheter, is inserted into the contralateral ulnar vein for radiotracer administration. Administration of the PET tracer is often timed to coincide with time of maximum (T max) or minimum (T min) of the imaging agent or precursor concentration in the blood.

The patient is positioned in the PET camera and a tracer dose of the PET tracer [$^{18}$F]-[targeting molecule]-4PEG-DBCO-FPPEGA imaging agent (<20 mCi) is administered via i.v. catheter. A subject may, prior to administration of the PET tracer, drink a liter of water to promote the renal clearance of unbound tracer from the circulation in order to enhance signal to background ratio and/or empty his bladder. Either arterial or venous blood samples may be taken at appropriate time intervals throughout the PET scan in order to, e.g., analyze and quantitate the fraction of unmetabolized PET tracer in plasma. Images may be acquired for up to 120 min. Within ten minutes of the injection of radiotracer and at the end of the imaging session, 1 ml blood samples may be obtained, e.g., for determining the plasma concentration of any labeled or unlabeled imaging agent or precursor or metabolite.

Two types of PET procedures may be used. One type involves obtaining single time point estimates of tracer uptake or static imaging that provides a spatial map of regional tracer concentration. With static imaging, only an average value is measured (e.g. Standardized Uptake Value, SUV). The second type is referred to as dynamic tracer imaging, which can provide considerably more information about in vivo biology by delineating both the temporal and spatial pattern of tracer uptake. See, e.g., Muzi et al. Magn Reson Imaging. 2012 30(9): 1203-1215. Imaging agents, such as such as [$^{18}$F]-[targeting molecule]-4PEG-DBCO-FPPEGA imaging agents, may be used in either static tracer imaging or dynamic tracer imaging.

For quantification of tracer uptake, the clinician may visually identify tumor lesions on a PET or CT scan and determine a region-of-interest (ROI) around these lesions. Imaging agent-uptake in these ROI's may be corrected for body weight and injected dose and quantified as standardized uptake value (SUVmax and SUVmean).

Tomographic images are obtained through image reconstruction. For determining the distribution of radiotracer, ROIs may be drawn on the reconstructed image including, but not limited to, the lungs, liver, heart, kidney, skin, or other organs and tissue (e.g., cancer tissue). Radiotracer uptakes over time in these regions are used to generate time activity curves (TAC) obtained in the absence of any intervention or in the presence of the unlabeled targeting molecule at the various dosing paradigms examined. Data may be expressed as radioactivity per unit time per unit volume (pci/cc/mCi injected dose).

PET may be accompanied by a low-dose or diagnostic CT-scan for anatomic reference purposes.

VIII. Exemplary PET Procedures with $^{18}$F Labeled Imaging Agents

By labeling a targeting molecule with Fluoride-18 ($^{18}$F), serial [$^{18}$F]-[targeting molecule]-4PEG-DBCO-FPPEGA imaging agents PET scanning can be used to assess whole body distribution, pharmacokinetics (PK) and pharmacodynamics (PD) and to relate findings to treatment effects. This could help in patient selection and possibly serve as an (early) biomarker for response to PD1/PD-L1 checkpoint inhibitors in the future.

Exemplary PET procedures with $^{18}$F labeled imaging agents, such as [$^{18}$F]-[targeting molecule]-4PEG-DBCO-FPPEGA imaging agents, are as follows.

In one embodiment, a method comprises (a) administering to a subject, e.g., a human, an imaging agent, e.g., an [$^{18}$F]-[targeting molecule]-4PEG-DBCO-FPPEGA imaging agent, at a dose of about 3-10 mCi (100-333 MBq); and (b) conducting a PET scan of the subject about 1-120 minutes (such as 30-120, 30-60 or 60-120 minutes) after step (a). The PET scan may be a static PET scan or a dynamic PET scan. If the PET scan is a static PET scan, the PET scan may occur 30-120, 30-60 or 60-120 minutes after administration of the imaging agent, and if the PET scan is a dynamic PET scan, it may occur 1-120, 30-120, 30-60 or 60-120 minutes after administration of the imaging agent, such as 1, 35, 70 and 105 minutes post injection. A dynamic PET scan may take a total duration of 30 to 120 minutes, such as 30 to 60 minutes, e.g., 30 minutes or 60 minutes, with variable frame lengths. The scan may be a whole body scan or a partial body scan, e.g., a scan of a single tumor. For example, a dynamic PET scan may be a scan of a single tumor and a static PET scan may be a whole body scan. In certain embodiments, the dose administered is about 200-225 MBq (i.e., ±10%) or about 6 mCi (i.e., ±10%).

In certain embodiments, a subject is a subject with cancer, and the method comprises (a) administering to the subject a PD-L1 imaging agent, e.g., an $^{18}$F labeled imaging agent, e.g., an [$^{18}$F]-[targeting molecule]-4PEG-DBCO-FPPEGA imaging agent, at a dose of about 3-10 mCi (100-333 MBq); and (b) conducting a PET scan of the subject about 1-120 minutes (such as 30-120, 30-60 or 60-120 minutes) after step (a), wherein steps (a) and (b) are conducted prior to the initiation of a cancer treatment. In certain embodiments, a subject is a subject with cancer, and the method comprises (a) administering to the subject an imaging agent, e.g., an $^{18}$F labeled PD-L1 Adnectin imaging agent, at a dose of about 3-10 mCi (100-333 MBq); and (b) conducting a PET scan of the subject about 1-120 minutes (such as 30-120, 30-60 or 60-120 minutes) after step (a), wherein steps (a) and (b) are conducted at at least 2 time points, e.g., one of which is prior to the initiation of a cancer treatment, and one of which is during the cancer treatment, or wherein both time points are during the cancer treatment. The two time points may be separated by, e.g., a time of 1-10 weeks, such as 2-8 weeks, such as 5-7 weeks, such as 6 weeks. In certain embodiments, steps (a) and (b) are conducted at at least 3, 4, 5 or more time points, wherein the successive time points are separated by, e.g., a time of 1-10 weeks, such as 2-8 weeks, such as 5-7 weeks, such as 6 weeks.

In certain embodiments, a subject is a subject with cancer and the subject is being treated with an immunotherapy, e.g., a PD-1 antagonist and/or a PD-L1 antagonist, and the method comprises (a) administering to the subject an agent, e.g., an [$^{18}$F]-[targeting molecule]-4PEG-DBCO-FPPEGA imaging agent, at a dose of about 3-10 mCi (100-333 MBq); and (b) conducting a PET scan of the subject about 1-120 minutes (such as 30-120, 30-60 or 60-120 minutes) after step (a), wherein steps (a) and (b) are conducted at at least 2, 3, 4 or 5 time points, e.g., one of which is prior to the initiation of the immunotherapy treatment, and one of which is during the immunotherapy treatment, or wherein both time points are during the immunotherapy treatment.

In certain embodiments, a subject is a subject with cancer and the subject is being treated with an immunotherapy, e.g., a PD-1 antagonist and/or a PD-L1 antagonist, and the method comprises (a) administering to the subject an imaging agent, e.g., an [$^{18}$F]-[targeting molecule]-4PEG-DBCO-FPPEGA imaging agent, at a dose of about 3-10 mCi (100-333 MBq); and (b) conducting a PET scan of the subject about 1-120 minutes (such as 30-120, 30-60 or 60-120 minutes) after step (a), wherein steps (a) and (b) are conducted at at least 1, 2, 3, 4 or 5 time points, e.g., one of which is prior to the initiation of the immunotherapy treatment, and if there are more than one iteration of steps (a) and (b), one of which is during the immunotherapy treatment, or wherein all time points are during the immunotherapy treatment, and wherein the results of the PET scan are informative for further treatment of the subject. For example, the results of the PET scan may indicate that the tumors of the subject are not reduced in size during the treatment, which suggests that the treatment may not be successful and should be changed or stopped. Alternatively, a first scan, prior to treatment, may indicate that the subject does not express the target molecule in a majority of tumors, and that a treatment with a PD-1 antagonist and/or a PD-L1 antagonist, would not be successful.

Methods in which more than one iteration of steps (a) and (b) are used may comprise comparing a PET scan conducted at a first time point with a PET scan conducted at a second time point, and/or later time point. Such comparison may inform on a patient's evolution of the disease, a patient's response to a treatment, a patient's potential adverse reaction or other.

In certain embodiments, a subject is a subject with cancer and the subject is being treating with an immunotherapy, e.g., a PD-1 antagonist and/or a PD-L1 antagonist, and the method comprises (a) administering to the subject an imaging agent, e.g., an [$^{18}$F]-[targeting molecule]-4PEG-DBCO-FPPEGA imaging agent, at a dose of about 3-10 mCi (100-333 MBq); and (b) conducting a PET scan of the subject about 1-120 minutes (such as 30-120, 30-60 or 60-120 minutes) after step (a), wherein steps (a) and (b) are conducted at at least 1, 2, 3, 4 or 5 time points, e.g., one of which is prior to the initiation of the immunotherapy treatment, and if there are more than one iteration of steps (a) and (b), one of which is during the immunotherapy treatment, or wherein all time points are during the immunotherapy treatment, wherein the imaging agent is an antibody, an antigen binding fragment of an antibody or derivative thereof, an Adnectin or an antigen binding peptide that binds an antigen set forth herein.

Also provided is a method of predicting whether a subject having a disease that is responsive to a therapy only if the subject expresses a target protein, is likely to respond to the therapy, comprising (a) administering to a subject having the disease an imaging agent comprising a molecule binding to the target protein, and obtaining an image (static or dynamic) of at least a portion of the subject to determine the presence of the target molecule in one or more tissues; and, if the target molecule is detected in one or more tumors, then, the subject is likely to respond to the therapy.

In certain examples, provided are methods of predicting whether a subject having cancer is likely to respond to a therapy with a PD-1 or PD-L1 antagonist, comprising (a) administering to a subject in need thereof an imaging agent, comprising an anti-PD-L1 imaging agent, e.g., as described herein, and obtaining an image (static or dynamic) of at least a portion of the subject to determine the presence of PD-L1 in one or more tumors; and, if PD-L1 is detected in one or more tumors, then, the subject is likely to respond to a therapy with a PD-1 or PD-L1 antagonist, and the therapy may be administered to the subject.

The methods may comprise administering an anti-tumor therapy when at least 1%, 5%, 10%, 20%, 30%, 40%. 50%, 60%, 70%, 80%, 90%, or 95% of the cells in a tumor specimen are PD-L1 positive, or on average across several tumors. In certain embodiments, an anti-tumor therapy, e.g., a PD-1 or PD-L1 antagonist, is not administered to the subject, unless the subject is PD-L1 positive in at least 1%, 5%, 10%, 20%, 30%, 40%, 50%, 60%, 70%, 80%, 90%, or 95% of the cells in a tumor specimen, or on average across several tumors. In certain embodiments, an anti-tumor therapy is administered if the level of PD-L detected in one or more tumors is at least equal to the level of PD-L1 that is necessary for receiving treatment with an a PD-1 or PD-L1 antagonist therapeutic.

Also provided herein are methods for treating a subject having a disease that is responsive to a therapy only if the subject expresses a given target protein, comprising
(a) administering to a subject in need thereof an imaging agent binding to the target protein, and obtaining an image (static or dynamic) of at least a portion of the subject to determine the presence of the target protein in one or more tissues; and, if the target protein is detected in one or more tissues, then,
(b) administering to the subject the therapy.

In certain embodiments, provided herein are methods for treating a subject having cancer, comprising (a) administering to a subject in need thereof an imaging agent comprising an anti-PD-L1 imaging agent, and obtaining an image (static or dynamic) of at least a portion of the subject to determine the presence of PD-L1 in one or more tumors; and, if PD-L1 is detected in one or more tumors, then (b) administering to the subject an anti-tumor therapy, e.g., an agent that inhibits the interaction between PD-1 and PD-L1 (a PD-1 or PD-L1 antagonist), e.g., OPDIVO™, KEYTRUDA™ or TECENTRIQ™.

Also provided herein are methods for determining whether a subject having cancer is likely to respond to an immunotherapy, e.g., with a PD-1 or PD-L1 antagonist, the method comprising (a) administering to the subject having cancer a PD-L1 imaging agent, e.g., an $^{18}$F labeled PD-L1 imaging agent, at a dose of about 3-10 mCi (100-333 MBq); and (b) conducting a PET scan of the subject about 1-120 minutes (such as 30-120, 30-60 or 60-120 minutes) after step (a), and if the subject has a level of PD-L1 in one tumor or across several tumors that is equal to or above that required for treatment with a PD-1 or PD-L1 antagonist (e.g., OPDIVO™, KEYTRUDA™ or TECENTRIQ™), then the subject is likely to respond to an anti-tumor therapy, e.g., a PD-1 or PD-L1 antagonist e.g., OPDIVO™, KEYTRUDA™ or TECENTRIQ™.

Provided herein is a method of treating a subject having cancer, comprising (a) administering to the subject a PD-L1 imaging agent, e.g., an $^{18}$F labeled PD-L1 imaging agent, at a dose of about 3-10 mCi (100-333 MBq); and (b) conducting a PET scan of the subject about 1-120 minutes (such as 30-120, 30-60 or 60-120 minutes) after step (a), and if the subject has a level of PD-L1 in one tumor or across several tumors that is equal to or above that required for treatment with a PD-1 or PD-L1 antagonist (e.g., OPDIVO™, KEYTRUDA™ or TECENTRIQ™), then administering to the subject an anti-tumor therapy, e.g., a PD-1 or PD-L1 antagonist e.g., OPDIVO™, KEYTRUDA™ or TECENTRIQ™ The following methods are also encompassed herein:

Use of a Her2-binding protein (such as an Fcab described in WO2009/132876 or in WO2015/049537) in an $^{18}$F labeled imaging agent for use as a complementary/companion diagnostic test to support use of therapeutics targeting Her2, including the Fcabs described in WO2009/132876 or WO2015/049537, trastuzumab, pertuzumab, or ado-trastuzumab emtansine, in Her2-overexpressing tumors. For example, in one embodiment, a Her-2 binding protein, e.g., a Her-2 binding Fcab (e.g., FS102), or an antigen-binding fragment of trastuzumab or pertuzumab is reacted to form an [$^{18}$F]-[Her2 binding protein]-4PEG-DBCO-FPPEGA imaging agent, and the imaging agent is administered to a subject prior to or during treatment with an anti-Her2 agent, e.g., FS102, trastuzumab, pertuzumab, or ado-trastuzumab emtansine.

Use of a fucosyl-GM1-binding protein (such as an antigen binding fragment derived from the antibody BMS-986012, WO2007067992) in an $^{18}$F labeled imaging agent for use as a complementary/companion diagnostic to support the use of a fucosyl-GM1-binding therapeutic, such as BMS-986012, in fucosyl-GM1 expressing or high-expressing tumors. For example, in one embodiment, a fucosyl-GM1 binding protein, e.g., an antigen binding fragment of BMS-986012 or antibody described in WO2007067992, is reacted to form [$^{18}$F]-[fucosyl-GM1 binding protein]-4PEG-DBCO-FPPEGA imaging agent, and the imaging agent is administered to a subject prior to or during treatment with an fucosyl-GM1 binding therapeutic, e.g., BMS-986012.

Use of a fucosyl-GM1-binding protein (such as an antigen binding fragment derived from the antibody BMS-986012, WO2007067992) in an $^{18}$F labeled imaging agent for use as a complementary/companion diagnostic to support the use of a fucosyl-GM1-binding ADC, such an ADC derived from BMS-986012, in fucosyl-GM1 expressing or high-expressing tumors.

Labelling a Met-binding protein (such as an antibody fragment) for use as a complementary/companion diagnostic test to support use of a Met-targeted antibody (such as onartuzumab) or a small-molecule Met inhibitor (such as tivantinib) in Met-high expressing tumors.

Labelling a CD30-binding protein for use as a complementary/companion diagnostic test to support use of a CD30-targeted ADC (such as brentuximab vedotin, Seattle Genetics) in CD30-expressing tumors.

Labelling a protein that binds to a target on the surface of tumor infiltrating lymphocytes or other immune cells, or a target on the surface of tumor cells that signals to immune cells or otherwise modulates the host anti-tumor response, such as PD-1, PD-L, PD-L2, CTLA-4, B7.1, SLAMF7, CSF1R, TIM3, LAG3, KIR, CD27, or CD137, for use as a complementary/companion diagnostic test to support use of an inhibitor or agonist of the target, or other immune-modulating agent, to promote an anti-tumor immune response.

Labelling a specific target-binding protein for use as a complementary/companion diagnostic test to support use of a specific target-binding ADC in tumors expressing the specific target. Examples of the target include, but are not limited to, Her2 (ado-trastuzumab emtansine, Genentech), CD30 (brentuximab vedotin, Seattle Genetics), Ly6E (Genentech), CD79b (Genentech), CD33 (Seattle Genetics), CD70 (Seattle Genetics), LIV-1 (Seattle Genetics), SLITRK6 (Seattle Genetics), Nectin-4 (Seattle Genetics), mesothelin (BMS-986148; Terrett et al., U.S. Pat. No. 8,268, 970 B2 (2012); antibody 6A4), and Glypican3 (BMS-986183; Terrett et al., U.S. Pat. No. 8,680,247 B2 (2014); antibody 4A6).

The amino acid sequences of the recited patents and patent applications and those of the recited antibodies are specifically incorporated by reference herein.

In applications describing use of an antibody-drug conjugate (ADC), applications using an alternative specific target-binding protein (such as Adnectins, single-domain antibodies, domain antibodies, single-chain variable fragments, Fcab fragments, or Fab fragments) conjugated to a drug are also envisioned. Also provided herein are the following methods:

Labelling a protein that binds to a target on the surface of tumor cells for use as a diagnostic test to support use of an inhibitor or agonist of the target, to inhibit tumor growth, promote differentiation or senescence, or activate cell death pathways. A method of treating cancer by inhibiting tumor growth, promoting differentiation or senescence, or activating cell death pathways, with an agonist or antagonist of a target on the surface of tumor cells, may comprise administering to a subject having cancer, an imaging agent that detects the target, and if the target is detected, then treating the subject with the agonist or antagonist of the target.

Labelling a protein that binds to a target on the surface of tumor cells, or other cells in the tumor microenvironment such as stromal cells or endothelial cells, for use as a diagnostic test to support use of an inhibitor or agonist of the target, to inhibit tumor growth, promote differentiation or senescence, or activate cell death pathways. A method of treating cancer with an agonist or antagonist of a target on the surface of tumor cells or other cells in the tumor microenvironment such as stromal cells or endothelial cells, may comprise administering to a subject having cancer, an imaging agent that detects the target, and if the target is detected then treating the subject with the agonist or antagonist of the target, to inhibit tumor growth, promote differentiation or senescence, or activate cell death pathways.

Labelling a protein that binds to a target on the surface of tumor cells that has limited distribution on normal tissues, for use as a diagnostic test or staging test for cancer.

Non-oncology applications, such as identifying the specific immune cell populations in auto-immune diseases to assist in diagnosis or selection of therapy, are also envisioned.

An imaging agent may specifically bind to any of the following target molecules: (i) an agonist of a co-stimulatory receptor and/or (ii) an antagonist of an inhibitory signal on T cells, both of which result in amplifying antigen-specific T cell responses (immune checkpoint regulators). Exemplary targets include: members of the immunoglobulin super family (IgSF); a member of a family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6; a member of the TNF family of molecules that bind to cognate TNF receptor family members, which include CD40 and CD40L, OX-40, OX-40L, CD70, CD27L, CD30, CD30L, 4-1BBL, CD137, GITR, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT.beta.R, LIGHT, DcR3, HVEM, VEGI/TL1A, TRAMP/DR3, EDAR, EDA1, XEDAR, EDA2, TNFR1, Lymphotoxin a/TNFβ, TNFR2, TNFα, LTβR, Lymphotoxin a 1 (32, FAS, FASL, RELT, DR6, TROY, NGFR (see, e.g., Tansey (2009) Drug Discovery Today 00:1); CTLA-4, PD-1, PD-L1, PD-L2, and LAG-3, TIM-3, Galectin 9, CEACAM-1, BTLA, CD69, Galectin-1, TIGIT, CD113, GPR56, VISTA, 2B4, CD48, GARP, CD73, PD1H, LAIR1, TIM-1, TIM-4, CD39, B7-1, B7-2, CD28, 4-1BB (CD137), 4-1BBL, GITR, GITRL, ICOS, ICOS-L, OX40, OX40L, CD70, CD27, CD40, DR3 and CD28H; inhibitory receptors on NK cells or agonists of activating receptors on NK cells, e.g., KIR; CSF-1; CSF-iR; TGF-beta; molecules on immune cells, e.g., T reg cells, macrophages, monocytes, CD73, BTLA, VISTA, LAG-3, B7-H3, B7-H4, IDO, TIGIT, MICA/B, or arginase; CD40, CD226, CD28, OX40, GITR, CD137, CD27, HVEM, or CD127; OX40, CD2, CD27, CDS, ICAM-1, LFA-1 (CD11a/CD18), ICOS (CD278), 4-1BB (CD137), 20 GITR, CD30, CD40, BAFFR, HVEM, CD7, LIGHT, NKG2C, SLAMF7, NKp80, CD160, B7-H3 or CD83 ligand. PD-1, PD-L1, PD-L2, CTLA4, TIM3, LAG3, VISTA, BTLA, TIGIT, LAIR1, CD160, 2B4 and/or TGFR beta, and HVEM.

Antigen binding fragments of the following antibodies may be used for preparing imaging agents as described herein: Yervoy™ (ipilimumab) or Tremelimumab (to CTLA-4), galiximab (to B7.1), BMS-936558 (to PD-1), CT-011 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4), lirilumab, CSF-1R such as CSF-iR antagonist antibodies including RG7155 (WO11/70024, WO11/107553, WO11/131407, WO13/87699, WO13/119716, WO13/132044) or FPA-008 (WO11/140249; WO13169264; WO14/036357); anti-PD-1 antibody nivolumab (BMS-936558) or an antibody that comprises the CDRs or variable regions of one of antibodies 17D8, 2D3, 4H1, 5C4, 7D3, 5F4 and 4A11 described in WO 2006/121168; anti-PD1 antibody MK-3475 (Lambrolizumab) described in WO2012/145493; AMP-514 described in WO 2012/145493; and CT-011 (Pidilizumab; previously CT-AcTibody or BAT; see, e.g., Rosenblatt et al. (2011) J. Immunotherapy 34:409); PD-1 antibodies described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368; PD-1 antibodies disclosed in WO2013/

173223; anti-PD-L1 antibody BMS-936559 (referred to as 12A4 in WO 2007/005874 and U.S. Pat. No. 7,943,743); an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743; anti-PD-L1 antibody MEDI4736 (also known as Anti-B7-H1) or MPDL3280A (also known as RG7446); anti-PD-L1 antibodies disclosed in WO2013/173223, WO2011/066389, WO2012/145493, U.S. Pat. Nos. 7,635,757 and 8,217,149; Yervoy™ (ipilimumab or antibody 10D1, described in PCT Publication WO 01/14424), tremelimumab (formerly ticilimumab, CP-675,206), anti-CTLA-4 antibody described in any of the following publications: WO 98/42752; WO 00/37504; U.S. Pat. No. 6,207,156; Hurwitz et al. (1998) Proc. Natl. Acad. Sci. USA 95(17):10067-10071; Camacho et al. (2004) J. Clin. Oncology 22(145): Abstract No. 2505 (antibody CP-675206); and Mokyr et al. (1998) Cancer Res. 58:5301-5304; anti-CTLA-4 antibodies disclosed in WO2013/173223; apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, anti-CS1 antibody, elotuzumab, anti-KIR2DL 1/2/3 antibody, lirilumab, anti-CD 137 antibody, urelumab, anti-GITR antibody, TRX518, anti-PD-L1 antibody, BMS-936559, MSB0010718C, MPDL3280A, anti-PD-L2 antibody, anti-ILT1 antibody, anti-ILT2 antibody, anti-ILT3 antibody, anti-ILT4 antibody, anti-ILT5 antibody, anti-ILT6 antibody, anti-ILT7 antibody, anti-ILT8 antibody, anti-CD40 antibody, anti-OX40 antibody, anti-CD 137 antibody, anti-KIR2DL1 antibody, anti-KIR2DL2/3 antibody, anti-KIR2DL4 antibody, anti-KIR2DL5A antibody, anti-KIR2DL5B antibody, anti-KIR3DL1 antibody, anti-KIR3DL2 antibody, anti-KIR3DL3 antibody, anti-NKG2A antibody, anti-NKG2C antibody, and/or an anti-NKG2E antibody.

IX. Kits and Articles of Manufacture

Also provided are kits for producing the $^{18}$F-radiolabeled targeting compositions described herein and instructions for use. Kits typically include a packaged combination of reagents in predetermined amounts with instructions and a label indicating the intended use of the contents of the kit. The term label includes any writing, or recorded material supplied on or with the kit, or which otherwise accompanies the kit.

For example, in some embodiments, the kit contains the reagents necessary for the prosthetic group in condition to be fluorinated on site with $^{18}$F, and then linking the radiolabeled prosthetic group to the BFC-linked targeting molecule (e.g., protein or peptide) prior to administration.

In certain embodiments, a kit comprises one or more reagents necessary for forming an $^{18}$F labeled in vivo imaging agent, such as a [$^{18}$F]-[targeting molecule]-4PEG-DBCO-FPPEGA, as further described herein. For example, a kit may comprise a first vial comprising [targeting molecule]-4PEG-DBCO and a second vial comprising [$^{18}$F] FPPEGA. A kit may comprise a first vial comprising [targeting molecule]-4PEG-DBCO, a second vial comprising un unlabeled precursor of [$^{18}$F]FPPEGA, such as 4-PEG-tosyl-azide, and optionally a third vial comprising $^{18}$F (e.g., in O$^{18}$ water). The kits may further comprise vials, solutions and optionally additional reagents necessary for the manufacture of [$^{18}$F]-[targeting molecule]-4PEG-DBCO-FPPEGA.

In some embodiments, the kit can further contain at least one additional reagent (e.g., pharmaceutically acceptable carrier). In some embodiments, the kit includes the reaction precursors to be used to generate the labeled probe according to the methods disclosed herein. The components of the kit can be tailored to the particular biological condition to be monitored as described herein. The kit can further include appropriate buffers and reagents known in the art for administering various combinations of the components listed above to the host cell or host organism. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. Suitable containers include, for example, bottles, vials, syringes, and test tubes. The containers may be formed from a variety of materials such as glass or plastic. It may further include other materials desirable from a commercial and user standpoint, including other buffers, diluents, filters, needles, syringes, and package inserts with instructions for use.

X. Uses

Methods of imaging using $^{18}$F-labeled targeting agents are provided herein. Positron emission tomography (PET) tracers such as the present $^{18}$F-radiolabeled protein-based PET probes can be used with currently available PET technology for use in exploratory and diagnostic imaging applications in vitro and in vivo. Imaging techniques and equipment for $^{18}$F imaging by PET scanning are well known in the art (see, e.g., U.S. Pat. Nos. 6,358,489; 6,953,567; Page et al., Nuclear Medicine And Biology, 21:911-919, 1994; Choi et al., Cancer Research 55:5323-5329, 1995; Zalutsky et al., J. Nuclear Med., 33:575-582, 1992) and any such known PET imaging technique or apparatus may be utilized.

In vivo applications of the imaging methods provided herein include disease diagnosis, monitoring of disease progression, prognosis, determining likelihood of a subject to respond to a treatment, determining eligibility to a treatment, monitoring of clinical response to therapy, clinical evaluation and dose selection of therapeutic compounds, preclinical studies of potential drug candidates in animal models, and the study of regional distribution and concentration of target molecules in tissues and organs. In vitro applications include screening of drug candidates in cell assays (e.g., competition assays, affinity assays, etc.)

In some embodiments, the $^{18}$F-labeled targeting agents can be used to determine the relationship between level of tissue occupancy by candidate therapeutic compounds and clinical efficacy in patients; to determine dose selection for clinical trials of drug candidates prior to initiation of long term clinical studies; and to compare potencies of different drug candidates.

In some embodiments, the $^{18}$F-radiolabeled targeting compound is used in a method for in in vivo imaging normal or diseased tissues and/or organs (e.g., lungs, heart, kidneys, liver, and skin). For example, the $^{18}$F-radiolabeled targeting compound is administered to a subject in an amount effective to result in uptake of the $^{18}$F-radiolabeled targeting compound into the cells or tissue of interest. The subject is then introduced to an appropriate imaging system (e.g., PET system) for a sufficient amount of time to allow detection of the $^{18}$F-radiolabeled targeting compound. The location of the detected signal from the $^{18}$F-radiolabeled targeting compound can be correlated with the location of the cells or tissue of interest. In some embodiments, the dimensions of the location can be determined as well. In vivo imaging is described herein. See also U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference.

Accordingly, in certain aspects, provided is a method of obtaining an image of an $^{18}$F-radiolabeled protein-based probe, the method comprising administering the $^{18}$F-radiolabeled protein-based probe to a subject, and imaging in vivo the distribution of the $^{18}$F-radiolabeled protein-based probe by PET.

In certain embodiments, the subject is a mammal, for example, a human, dog, cat, ape, monkey, rat, or mouse.

In certain aspects, provided is a method of diagnosing the presence of a disease in a subject, the method comprising administering to a subject in need thereof an $^{18}$F-radiolabeled protein-based probe which binds to a target molecule associated with the presence of the disease, and obtaining a radio-image of at least a portion of the subject to detect the presence or absence of the $^{18}$F-radiolabeled protein-based probe.

In some embodiments, the disease is a solid cancer, hematopoietic cancer, hematological cancer, autoimmune disease, neurodegenerative disease, cardiovascular disease or pathogenic infection.

PET imaging with an $^{18}$F-radiolabeled targeting compound may be used to qualitatively or quantitatively detect the targeting compound. An $^{18}$F-radiolabeled targeting compound imaging agent may be used as a biomarker, and the presence or absence of a positive signal in a subject may be indicative that, e.g., the subject would be responsive to a given therapy, e.g., a cancer therapy, or that the subject is responding or not to a therapy.

In some embodiments, the steps of this method can be repeated at determined intervals so that the location and/or size of the disease can be monitored as a function of time and/or treatment. In certain embodiments, the $^{18}$F-radiolabeled targeting compound can be used in a subject undergoing treatment (e.g., chemotherapy, etc.), to aid in visualizing response to the treatment. For example, the $^{18}$F-radiolabeled targeting compound is typically visualized and sized prior to treatment, and periodically (e.g., daily, weekly, monthly, intervals in between these, and the like) during treatment to monitor the progression or regression of the disease in the patient.

Accordingly, in certain aspects, provided is a method of monitoring the progress of a disease in a subject in need thereof, the method comprising administering to the subject an $^{18}$F-radiolabeled protein-based probe which binds to a target molecule associated with the presence of the disease at a first time point and obtaining an image of at least a portion of the subject to determine the amount of diseased cells or tissue, and administering to the subject the $^{18}$F-radiolabeled protein-based probe at one or more subsequent time points and obtaining an image of at least a portion of the subject at each subsequent time point (e.g., same portion as the first time point).

In certain embodiments, the size of a tumor can be monitored in a subject undergoing cancer therapy (e.g., chemotherapy, radiotherapy) and the extent of regression of the tumor can be monitored in real-time based on detection of $^{18}$F-radiolabeled tumor targeting.

In some embodiments, the methods herein are used to evaluate the patient's response to therapy. In some embodiments, the methods are used to select or modify the dosage of therapeutic compounds. In some embodiments, the methods are used to monitor the uptake of the $^{18}$F-radiolabeled targeting compound in normal tissues to analyze toxicity or patient to patient variation. In some embodiments, the methods are used to monitor drug efficacy or to detect drug resistance.

In some embodiments, the radiolabeled compounds are administered to mammals, preferably humans, in a pharmaceutical composition, either alone or in combination with pharmaceutically acceptable carriers or diluents according to standard pharmaceutical practice. Such compositions can be administered orally or parenterally, including the intravenous, intramuscular, intraperitoneal, subcutaneous, rectal and topical routes of administration. In certain embodiments, administration is intravenous. In certain embodiments the radiolabeled compound is administered via intravenous injection within less than one hour of synthesis.

In some embodiments, the biological activity of the $^{18}$F-radiolabeled targeting agent in vivo may be measured in terms of organ-specific uptake by biodistribution studies and dynamic small animal PET imaging studies in an appropriate animal model. For example, for biodistribution studies, a group of animals are injected with the $^{18}$F-radiolabeled targeting agent and the subsets of the animals are sacrificed at one or more time intervals (e.g., 5 min., 10 min., 30 min., 60 min., 2 h). Organs and tissues of interest are rapidly excised and weighed, and radioactivity determined. Accumulated radioactivity in organs and selected tissues is calculated as the percentage of injected dose (% ID).

In some embodiments, the $^{18}$F-radiolabeled targeting agent provided herein is used in vitro as a screening tool to select compounds for use in treating tissues or cells. For example, in some embodiments, diseased cells are incubated with the $^{18}$F-radiolabeled targeting compound during or after exposure to one or more candidate drugs. The ability of the drug candidate to affect the disease can be imaged over time using the $^{18}$F-radiolabeled targeting compound.

For example, the integrity of biological activity of the $^{18}$F-radiolabeled targeting agent in vitro in terms of specific binding to the selected target molecule and uptake of the radiolabeled composition is assessed in a cell line expressing the target molecule. For binding and cell association assays, cells are incubated at 4° C. or 37° C. for an appropriate time with the $^{18}$F-radiolabeled targeting composition. Nonspecific binding is determined by the addition of an excess of unlabeled targeting agent. The extent of specific binding is calculated by subtracting the nonspecific binding from the total binding. Uptake is expressed as a percentage of the total added dose of targeting agent to the cells per microgram of protein (% ID/μg cell protein).

In a related aspect, the present invention provides a diagnostic or radiopharmaceutical composition for in vivo or in vitro, which includes an $^{18}$F-radiolabeled protein-based probe, and a pharmaceutically acceptable carrier.

EXEMPLARY EMBODIMENTS

1. A compound comprising an $^{18}$F-radiolabeled prosthetic group having the structure

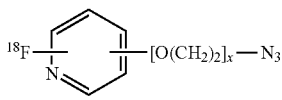

or a pharmaceutically acceptable salt thereof, wherein x is an integer from 1 to 8 and the $^{18}$F-radiolabel is attached ortho to the N atom of the pyridine. 2. The compound of embodiment 1, wherein the $^{18}$F-radiolabeled prosthetic group has the structure

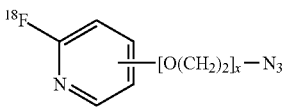

or a pharmaceutically acceptable salt thereof.

3. The compound of embodiments 1 or 2, wherein the $[O(CH_2)_2]_x$ moiety is present in the 1-3 configuration relative to the nitrogen on the pyridine ring.

4. The compound of embodiments 1 or 2, wherein the $[O(CH_2)_2]_x$ moiety is present in the 1-2 configuration relative to the nitrogen on the pyridine ring.

5. The compound of embodiments 1 or 2, wherein the $[O(CH_2)_2]_x$ moiety is present in the 1-4 configuration relative to the nitrogen on the pyridine ring.

6. The compound of embodiment 1, wherein the $^{18}$F-radiolabeled prosthetic group has the structure

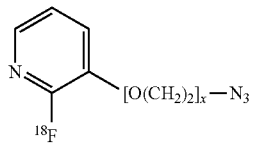

or a pharmaceutically acceptable salt thereof.

7. The compound of any one of the preceding embodiments, wherein x is an integer from 2 to 6, or a pharmaceutically acceptable salt thereof.

8. The compound of embodiment 4, wherein x is an integer from 3 to 5, or a pharmaceutically acceptable salt thereof.

9. The compound of embodiment 4, wherein x is 4, or a pharmaceutically acceptable salt thereof.

10. The compound of embodiment 1, wherein the $^{18}$F-radiolabeled prosthetic group has the structure

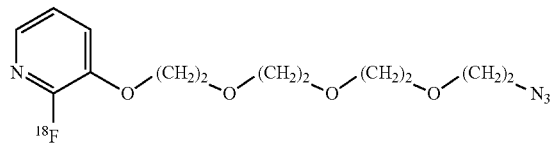

or a pharmaceutically acceptable salt thereof.

11. The compound of any one of the preceding embodiments, wherein the pyridine ring comprises an additional substituent which does not interfere with the fluorination reaction.

12. The compound of embodiment 11, wherein the substituent on the pyridine ring is a $C_{1-6}$ alkyl.

13. The compound of embodiment 12, wherein the substituent is methyl, ethyl or propyl.

14. A compound comprising an $^{18}$F-radiolabeled prosthetic group having the structure

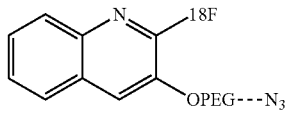

wherein "OPEG" is $[O(CH_2)_2]_x$, and x is an integer from 1 to 8, or a pharmaceutically acceptable salt thereof.

15. The compound of embodiment 14, wherein x is an integer from 2 to 6, or a pharmaceutically acceptable salt thereof.

16. The compound of embodiment 14, wherein x is an integer from 3 to 5, or a pharmaceutically acceptable salt thereof.

17. The compound of embodiment 15, wherein x is 4, or a pharmaceutically acceptable salt thereof.

18. The compound or pharmaceutically acceptable salt thereof of any one of the preceding embodiments which is water soluble.

19. The compound or pharmaceutically acceptable salt thereof of any one of the preceding embodiments which is not volatile.

20. An $^{18}$F-radiolabeled protein-based probe comprising $^{18}$F-radiolabeled prosthetic group, a bifunctional conjugating (BFC) moiety and a protein with the following structure,

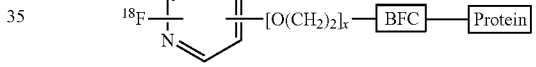

wherein the $^{18}$F is ortho to the N atom, x is an integer from 1 to 8, or pharmaceutically acceptable salt thereof.

21. The $^{18}$F-radiolabeled protein-based probe of embodiment 20, wherein $^{18}$F-radiolabeled prosthetic group has the following structure,

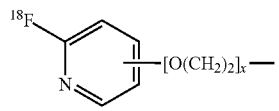

22. The $^{18}$F-radiolabeled protein-based probe of embodiments 20 or 21, wherein the $[O(CH_2)_2]_x$ moiety is present in the 1-3 configuration relative to the nitrogen on the pyridine ring.

23. The $^{18}$F-radiolabeled protein-based probe of embodiments 20 or 21, wherein the $[O(CH_2)_2]_x$ moiety is present in the 1-2 configuration relative to the nitrogen on the pyridine ring.

24. The $^{18}$F-radiolabeled protein-based probe of embodiments 20 or 21, wherein the $[O(CH_2)_2]_x$ moiety is present in the 1-4 configuration relative to the nitrogen on the pyridine ring.

25. The $^{18}$F-radiolabeled protein-based probe of embodiment 20, wherein $^{18}$F-radiolabeled prosthetic group has the following structure,

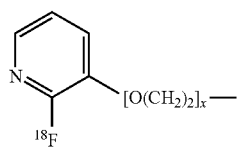

26. The $^{18}$F-radiolabeled protein-based probe of any one of the embodiments 20 to 25, wherein x is an integer from 2 to 6.
27. The $^{18}$F-radiolabeled protein-based probe of embodiment 26, wherein x is an integer from 3 to 5.
28. The $^{18}$F-radiolabeled protein-based probe of embodiment 26, wherein x is 4.
29. The $^{18}$F-radiolabeled protein-based probe of any one of embodiments 20-28, wherein the [O(CH$_2$)$_2$]$_x$ moiety is present in the 1-3 configuration relative to the nitrogen on the pyridine ring.
30. The $^{18}$F-radiolabeled protein-based probe of any one of the embodiments 20-29, wherein the pyridine ring comprises an additional substituent which does not interfere with the fluorination reaction.
31. The $^{18}$F-radiolabeled protein-based probe of embodiment 30, wherein the substituent on the pyridine ring is a C$_{1-6}$ alkyl.
32. The $^{18}$F-radiolabeled protein-based probe of embodiment 31, wherein the substituent is methyl, ethyl or propyl.
33. The $^{18}$F-radiolabeled protein-based probe of embodiment 20, wherein the $^{18}$F-radiolabeled prosthetic group has the structure

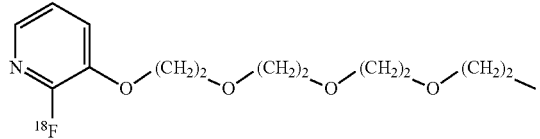

34. An $^{18}$F-radiolabeled protein-based probe comprising $^{18}$F-radiolabeled prosthetic group, a bifunctional conjugating (BFC) moiety and a protein with the following structure

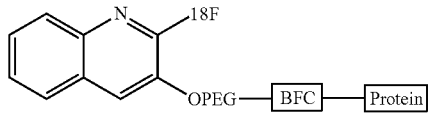

wherein "OPEG" is [O(CH$_2$)$_2$]$_x$, and x is an integer from 1 to 8, or a pharmaceutically acceptable salt thereof.
35. The $^{18}$F-radiolabeled protein-based probe of embodiment 34, wherein x is an integer from 2 to 6, or a pharmaceutically acceptable salt thereof.
36. The $^{18}$F-radiolabeled protein-based probe of embodiment 34, wherein x is an integer from 3 to 5, or a pharmaceutically acceptable salt thereof.
37. The $^{18}$F-radiolabeled protein-based probe of embodiment 34, wherein x is 4, or a pharmaceutically acceptable salt thereof.
38. The $^{18}$F-radiolabeled protein-based probe of any one of embodiments 20 to 37, wherein the BFC is a cyclooctyne comprising a reactive group that forms a covalent bond with an amine, carboxyl, carbonyl or thiol functional group on the protein.

39. The $^{18}$F-radiolabeled protein-based probe of embodiment 38, wherein the cyclooctyne is selected from the group consisting of dibenzocyclooctyne (DIBO), biarylazacyclooctynone (BARAC), dimethoxyazacyclooctyne (DIMAC) and dibenzocyclooctyne (DBCO).
40. The $^{18}$F-radiolabeled protein-based probe of embodiment 39, wherein the cyclooctyne is DBCO.
41. The $^{18}$F-radiolabeled protein-based probe of any one of embodiments 20 to 40, wherein the BFC further comprises a polyethylene glycol (PEG)$_y$ spacer arm, wherein y is an integer from 1 to 8.
42. The $^{18}$F-radiolabeled protein-based probe of embodiment 41, wherein y is an integer from 2 to 6.
43. $^{18}$F-radiolabeled protein-based probe of embodiment 41, wherein y is 4 or 5.
44. The $^{18}$F-radiolabeled protein-based probe of embodiment 39, wherein the BFC is DBCO-PEG4-NHS-Ester, DBCO-Sulfo-NHS-Ester, DBCO-PEG4-Acid, DBCO-PEG4-Amine or DBCO-PEG4-Maleimide.
45. The $^{18}$F-radiolabeled protein-based probe of embodiment 44, wherein the BFC is DBCO-PEG4-Maleimide.
46. The $^{18}$F-radiolabeled protein-based probe of embodiment 45, having the following structure,

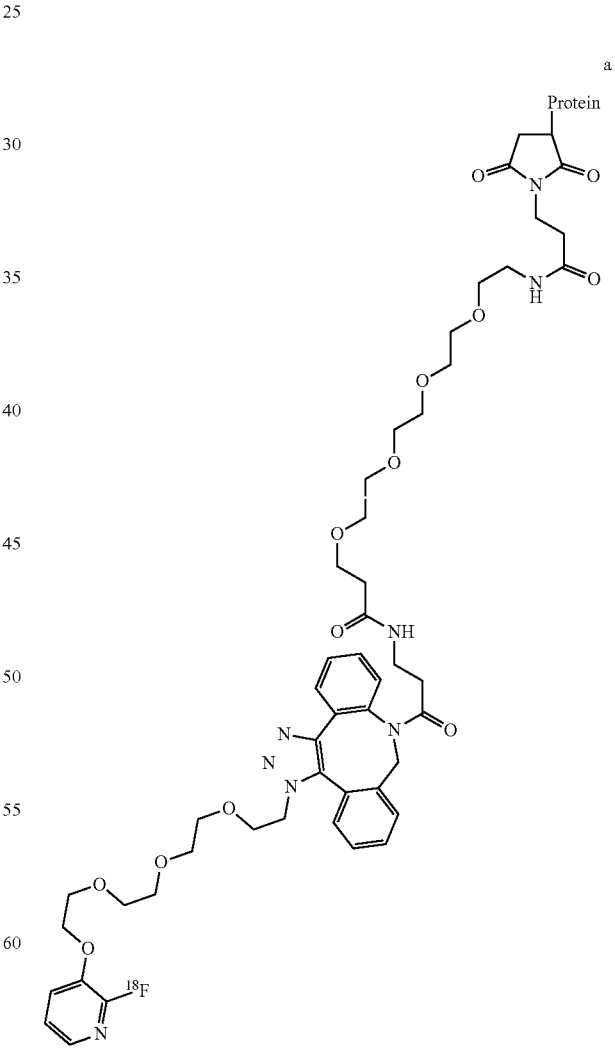

wherein the maleimide group of the BFC is covalently linked to the thiol group on a cysteine residue of the protein.

47. The $^{18}$F-radiolabeled protein-based probe of embodiment 46, wherein the cysteine residue is at the C-terminus of the protein.
48. The $^{18}$F-radiolabeled protein-based probe of any one of embodiments 20 to 47, wherein the protein portion of the probe binds to a biological molecule associated with a disease.
49. The $^{18}$F-radiolabeled protein-based probe of embodiment 48, wherein the disease is selected from the group consisting of solid cancers, hematopoietic cancers, hematological cancers, autoimmune disease, neurodegenerative disease, cardiovascular disease, and pathogenic infection.
50. The $^{18}$F-radiolabeled protein-based probe of any one of embodiments 20 to 49, wherein the protein portion of the probe comprises a ligand.
51. The $^{18}$F-radiolabeled protein-based probe of any one of embodiments 20 to 49, wherein the protein portion of the probe comprises an antibody or antibody fragment.
52. The $^{18}$F-radiolabeled protein-based probe of any one of embodiments 20 to 49, wherein the protein portion of the probe comprises a fibronectin based scaffold (FBS).
53. The $^{18}$F-radiolabeled protein-based probe of any one of embodiments 20 to 52, wherein the probe binds to a tumor-associated antigen.
54. The $^{18}$F-radiolabeled protein-based probe of any one of embodiments 20 to 52, wherein the probe binds to a protein present on a pathogenic organism.
55. The $^{18}$F-radiolabeled protein-based probe of embodiment 54, wherein the pathogenic organism is a virus, bacterium or fungus.
56. A method of obtaining an image of an $^{18}$F-radiolabeled protein-based probe of any one of embodiments 20 to 55, the method comprising,
    a) administering the $^{18}$F-radiolabeled protein-based probe to a subject; and
    b) imaging in vivo the distribution of the $^{18}$F-radiolabeled protein-based probe by positron emission tomography (PET) scanning.
57. The method of embodiment 56, wherein the imaged distribution of the $^{18}$F-radiolabeled protein-based probe is indicative of the presence or absence of a disease.
58. A method of diagnosing the presence of a disease in a subject, the method comprising
    (a) administering to a subject in need thereof an $^{18}$F-radiolabeled protein-based probe of any one of embodiments 20 to 55 which binds to a target molecule associated with the presence of the disease; and
    (b) obtaining an radio-image of at least a portion of the subject to detect the presence or absence of the $^{18}$F-radiolabeled protein-based probe;
wherein the presence and location of the $^{18}$F-radiolabeled protein-based probe above background is indicative of the presence and location of the disease.
59. A method of monitoring the progress of a disease in a subject, the method comprising
    (a) administering to a subject in need thereof an $^{18}$F-radiolabeled protein-based probe of any one of embodiments 20 to 55 which binds to a target molecule associated with the presence of the disease at a first time point and obtaining an image of at least a portion of the subject to determine the amount of the diseased cells or tissue; and
    (b) administering to the subject the $^{18}$F-radiolabeled protein-based probe at one or more subsequent time points and obtaining an image of at least a portion of the subject at each time point; wherein the dimension and location of the diseased cells or tissue at each time point is indicative of the progress of the disease.
60. A method of quantifying diseased cells or tissues in a subject, the method comprising
    (a) administering to a subject having diseased cells or tissues an $^{18}$F-radiolabeled protein-based probe of any one of embodiments 20 to 55 which binds to a target molecule located with the diseased cells or tissues; and
    (b) detecting radioactive emissions of the $^{18}$F in the diseased cells or tissue, wherein the level and distribution of the radioactive emissions in the diseased cells or tissues is a quantitative measure of the diseased cells or tissues.
61. The method of any one of embodiments 58 to 60, wherein the disease is selected from the group consisting of solid cancers, hematopoietic cancers, hematological cancers, autoimmune disease, neurodegenerative disease cardiovascular disease, and pathogenic infection.
62. A method of obtaining a quantitative image of tissues or cells expressing a target protein, the method comprising contacting the cells or tissue with an $^{18}$F-radiolabeled protein-based probe of any one of embodiments 20 to 55 which binds to the target protein, and detecting or quantifying the tissue expressing the target protein using positron emission tomography (PET).
63. A method of screening for an agent for treating a disease comprising the steps of
    (a) contacting cells expressing a target protein associated with the disease with an $^{18}$F-radiolabeled protein-based probe of any one of embodiments 20 to 55 which binds to the target protein in the presence and absence of a candidate agent; and
    (b) imaging the cells in the presence and absence of the candidate agent using positron emission tomography (PET), wherein a decrease in the amount of radioactive emissions in the presence of the candidate agent is indicative of that the agent binds to the target protein.
64. The method any one of embodiments 56 to 63, wherein the $^{18}$F-radiolabeled protein-based probe comprises a ligand.
65. The method any one of embodiments 56 to 63, wherein the $^{18}$F-radiolabeled protein-based probe comprises an antibody or antibody fragment.
66. The method any one of embodiments 56 to 63, wherein the $^{18}$F-radiolabeled protein-based probe comprises a fibronectin based scaffold (FBS).
67. The method any one of embodiments 56 to 63, wherein the $^{18}$F-radiolabeled protein-based probe binds to a tumor-associated antigen.
68. The method any one of embodiments 56 to 63, wherein $^{18}$F-radiolabeled protein-based probe binds to a protein present on a pathogenic organism.
69. The method of embodiment 68, wherein the pathogenic organism is a virus, bacterium or fungus.
70. A pharmaceutical composition comprising the $^{18}$F-radiolabeled protein-based probe of any one of embodiments 20 to 55.
71. A kit comprising the reaction precursors for use in producing the $^{18}$F-radiolabeled protein-based probe of any one of embodiments 20 to 55, and instructions for producing the $^{18}$F-radiolabeled protein-based probe.
72. A method for preparing an $^{18}$F-radiolabeled compound with the following structure,

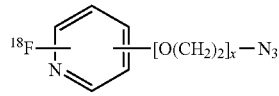

wherein x is an integer from 1 to 8, the method comprising the steps of
(a) providing a solution of a compound a with the following structure:

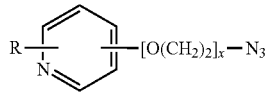

a wherein x is an integer from 1 to 8, and R is NO₂, Br, F or

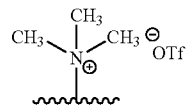

and is ortho to the N atom of the pyridine ring;
(b) providing a mixture of $^{18}$F in $^{18}$O water, 4,7,13,16, 21,24-hexaoxa-1,10-diazabicyclo[8.8.8]hexacosane and a weak base;
c) drying the mixture from step b) to form a solid; and
d) reacting the solution from step a) with the solid from step c) to form the $^{18}$F-labeled compound.

73. The method of embodiment 72, wherein the $^{18}$F-radiolabeled compound has the structure

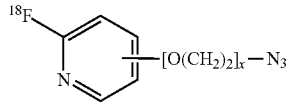

74. The compound of embodiment 72 or 73, wherein the [O(CH₂)₂]$_x$ moiety is present in the 1-3 configuration relative to the nitrogen on the pyridine ring.
75. The compound of embodiment 72 or 73, wherein the [O(CH₂)₂]$_x$ moiety is present in the 1-2 configuration relative to the nitrogen on the pyridine ring.
76. The compound of embodiment 72 or 73, wherein the [O(CH₂)₂]$_x$ moiety is present in the 1-4 configuration relative to the nitrogen on the pyridine ring.
77. The method of embodiment 73, wherein the $^{18}$F-radiolabeled compound has the structure

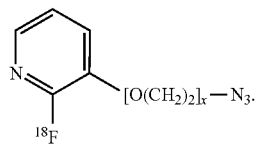

78. The method of any one of embodiments 72 to 77, wherein x is an integer from 2 to 6.
79. The method of embodiment 78, wherein x is an integer from 3 to 5.
80. The method of embodiment 78, wherein x is 4.
81. The method of embodiment 72, wherein the $^{18}$F-radiolabeled prosthetic group has the structure

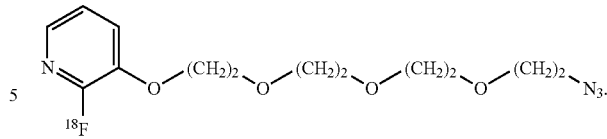

82. A method for preparing an $^{18}$F-labeled compound of the structure

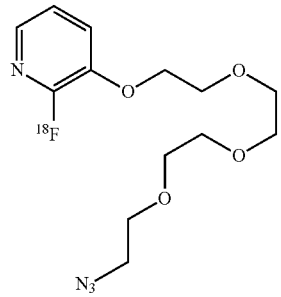 [SMILES: [N-]=[N+]=NCCOCCOCCOCCOc1cccnc1[18F]]

which comprises
a) providing a solution of the compound of the structure

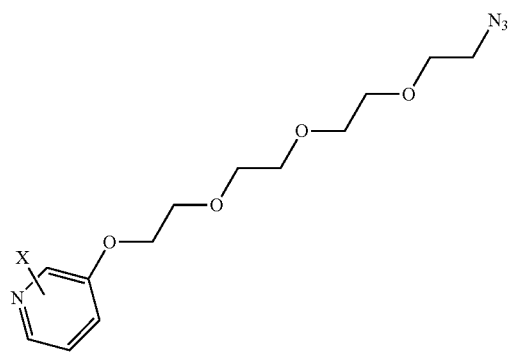

where X is NO₂, Br or

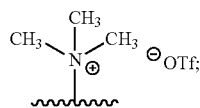

b) providing a mixture of $^{18}$F in $^{18}$O water, 4,7,13,16,21, 24-hexaoxa-1,10-diazabicyclo[8.8.8]hexacosane and weak base;
c) drying the mixture from step b) to form a solid; and
d) reacting the solution from step a) with the solid from step c) to form the $^{18}$F-labeled compound.
83. The method of embodiment 72, wherein R is NO₂ in the starting compound from step a).
84. A method of producing the $^{18}$F-radiolabeled protein-based probe of any one of embodiments 20 to 55, the method comprising coupling the $^{18}$F-radiolabeled prosthetic group of any one of embodiments 1 to 19 with a protein comprising a bifunctional conjugating (BFC) moiety using a bioorthogonal click reaction.
85. The method of embodiment 84, wherein the bioorthogonal click reaction is metal free.

86. The method of embodiment 84 or 85, wherein the BFC coupled to the protein comprises a cyclooctyne.

87. The method of embodiment 86, wherein the cyclooctyne is DBCO-PEG4-Maleimide.

INCORPORATION BY REFERENCE

All documents and references, including patent documents and websites, described herein are individually incorporated by reference to into this document to the same extent as if there were written in this document in full or in part.

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

Example 1

Preparation of 2-(2-(2-(2-azidoethoxy)ethoxy)ethoxy)ethyl 4-methylbenzenesulfonate

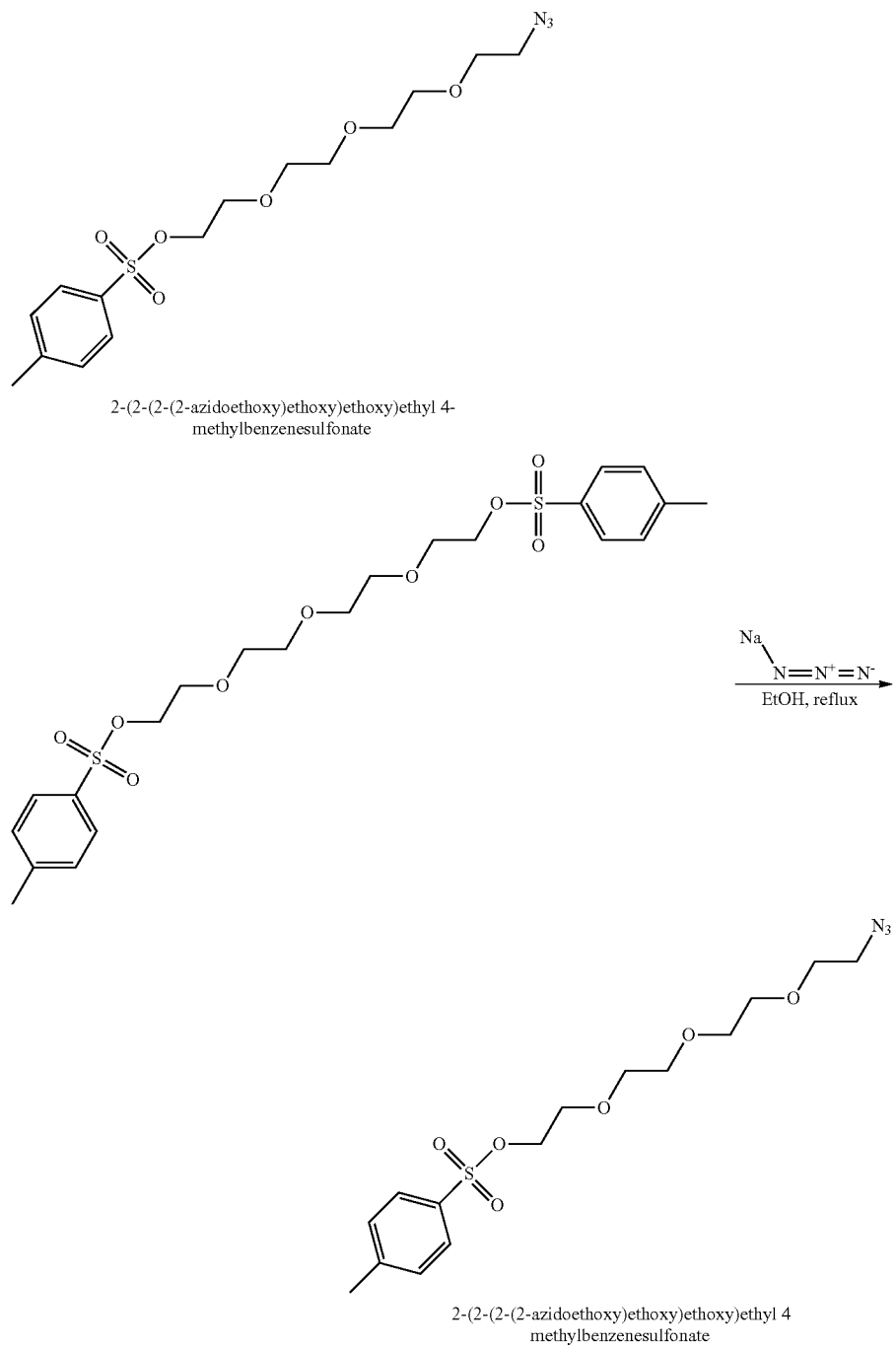

A mixture of ((oxybis(ethane-2,1-diyl))bis(oxy))bis(ethane-2,1-diyl) bis(4-methylbenzenesulfonate) (5 g, 9.95 mmol) and SODIUM AZIDE (0.647 g, 9.95 mmol) were dissolved in ethanol (50 mL) and the reaction was refluxed at 90° C. over a 17 hour period. The solvent was removed using partial vacuum and then loaded onto a 40 gram silica cartridge and was purified using flash chromatography (Isco-CombiFlash—eluted using a linear gradient method starting from 10% ethyl acetate in hexanes going to a 90% ethyl acetate in hexanes over a 45 minute period. The pooled fractions were checked by TLC and combined to give 2-(2-(2-(2-azidoethoxy)ethoxy)ethoxy)ethyl 4-methylbenzenesulfonate as a colorless oil. Due to the reactive nature of the 2-(2-(2-(2-azidoethoxy)ethoxy)ethoxy)ethyl 4-methylbenzenesulfonate product this material was used "as is" without any further characterizations.

Example 2

Preparation of 3-(2-(2-(2-(2-azidoethoxy)ethoxy)ethoxy)ethoxy)-2-fluoropyridine

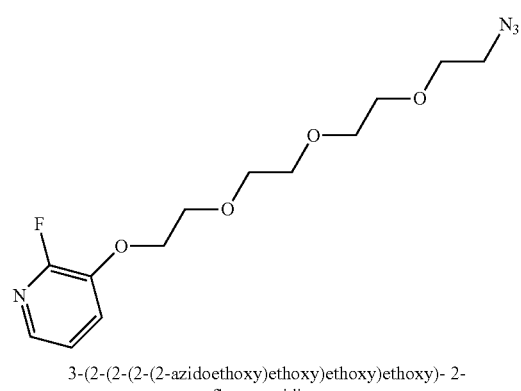

3-(2-(2-(2-(2-azidoethoxy)ethoxy)ethoxy)ethoxy)-2-fluoropyridine

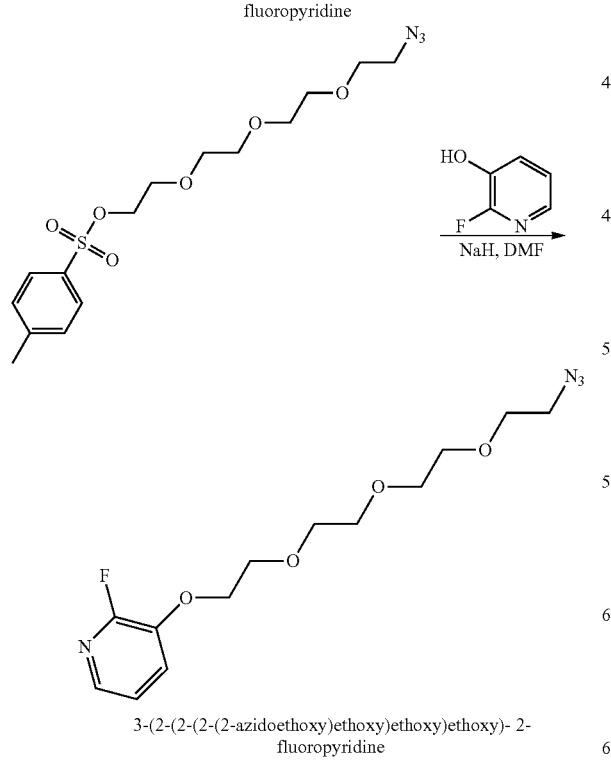

3-(2-(2-(2-(2-azidoethoxy)ethoxy)ethoxy)ethoxy)-2-fluoropyridine

To the suspension of sodium hydride (0.129 g, 3.21 mmol) in DMF (10 mL) at 0° C. was dropwise added a stirring solution of 2-fluoropyridin-3-ol (0.363 g, 3.21 mmol) in DMF (5 mL), then followed by the dropwise addition of the solution of 2-(2-(2-(2-azidoethoxy)ethoxy)ethoxy)ethyl 4-methylbenzenesulfonate (1.00 g, 2.68 mmol) in DMF (5 mL). The suspension was held at 0° C. for 10 min, then brought to ambient temperature for 1 hour, followed by addition heating at 60° C. for 4 hours. Solvent was removed in vacuo. 100 ml of ethyl acetate was added followed by 3 separate wash extractions with concentrated brine solution. The organic layer was dried over sodium sulfate, filtered and concentrated. The crude material was purified using flash chromatography (IscoCombiFlash—eluted with 10-50% EtOAc in Hex) to give a colorless oil. 3-(2-(2-(2-(2-azidoethoxy)ethoxy)ethoxy)ethoxy)-2-fluoropyridine (702 mg, 2.233 mmol, 83% yield) was isolated as a clear oil. $^1$H NMR (400 MHz, CHLOROFORM-d) δ 7.75 (dt, J=4.9, 1.6 Hz, 1H), 7.33 (ddd, J=10.0, 8.1, 1.5 Hz, 1H), 7.10 (ddd, J=7.9, 4.9, 0.7 Hz, 1H), 4.30-4.16 (m, 2H), 3.95-3.83 (m, 2H), 3.80-3.61 (m, 10H), 3.38 (t, J=5.1 Hz, 2H) 13C NMR (101 MHz, CHLOROFORM-d) δ 142.3, 137.7, 137.5, 123.4, 123.4, 121.7, 121.6, 77.3, 76.7, 70.9, 70.7, 70.6, 70.0, 69.4, 69.0, 50.6 19F NMR (400 MHz, CHLOROFORM-d) δ -83.55. HRMS (ESI) Theory: C13H20FN4O4+m/z 315.464; found 315.1463.

Example 3

Preparation of 3-(2-(2-(2-(2-azidoethoxy)ethoxy)ethoxy)ethoxy)-2-nitropyridine

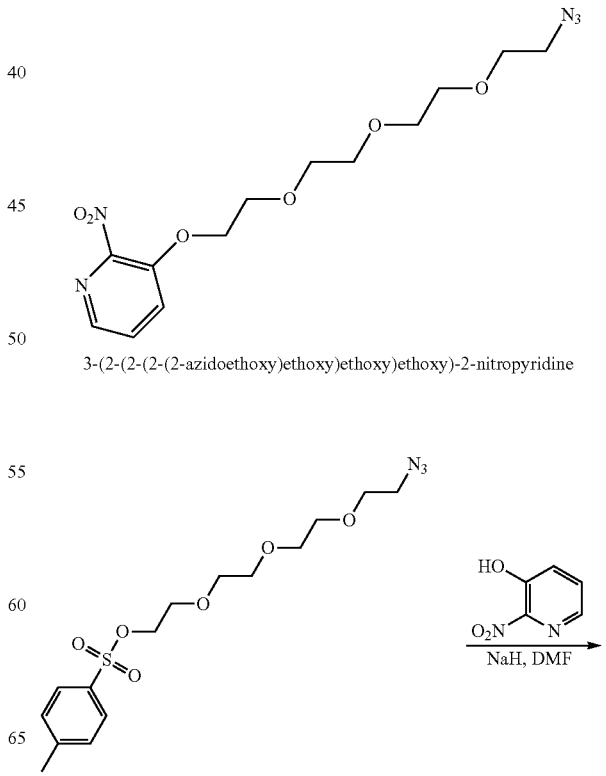

3-(2-(2-(2-(2-azidoethoxy)ethoxy)ethoxy)ethoxy)-2-nitropyridine

-continued

3-(2-(2-(2-(2-azidoethoxy)ethoxy)ethoxy)ethoxy)-2-nitropyridine

Sodium hydride (0.121 g, 3.01 mmol) (60% suspension in oil) was dissolved in DMF (7.0 mL) and the resulting suspension was cooled to 0° C. A solution of 2-nitropyridin-3-ol (0.384 g, 2.74 mmol) in DMF (1.5 mL) was added slowly, followed by the drop wise addition of 2-(2-(2-(2-azidoethoxy)ethoxy)ethoxy)ethyl 4-methylbenzenesulfonate (1.023 g, 2.74 mmol) in DMF (1.5 mL). The suspension was held at 0° C. for 10 minutes, then brought to ambient temperature for 2 hours followed by heating 60° C. for a 72 hour period. Reaction was quenched with 10 ml of DI water, followed by ethyl acetate extraction (3×10 mL). Pooled EtOAc extracts were washed with a concentrated brine solution (10 mL), dried over sodium sulfate, filtered and evaporated under reduced pressure to give a light yellow oil. The crude was purified by flash chromatography. 24 g silica cartridge, 25 mL/min, starting from 10% ethyl acetate in hexanes, followed by a linear change to 50% ethyl acetate in hexanes over a 25 minute period. After this time the gradient was held at this solvent composition for 10 minutes then changed to 100% ethyl acetate over a 10 minute period. 3-(2-(2-(2-(2-azidoethoxy)ethoxy)ethoxy)ethoxy)-2-nitropyridine was eluted between 30-40 minute portion of the chromatogram and the pooled fractions were evaporated under reduced pressure, then under vacuum for 2 hours to give 3-(2-(2-(2-(2-azidoethoxy)ethoxy)ethoxy)ethoxy)-2-nitropyridine (687 mg, 1.973 mmol, 72.0% yield) as a light yellow oil. $^1$H NMR (400 MHz, CHLOROFORM-d) δ 8.11 (dt, J=4.9, 1.6 Hz, 1H), 7.60 (ddd, J=10.0, 8.1, 1.5 Hz, 1H), 7.52 (ddd, J=7.9, 4.9, 0.7 Hz, 1H), 4.30-4.16 (m, 2H), 3.95-3.83 (m, 2H), 3.80-3.61 (m, 10H), 3.38 (t, J=5.1 Hz, 2H) 13C NMR (101 MHz, CHLOROFORM-d) δ 147.3, 139.5, 128.4, 124.4, 71.1, 70.7, 70.6, 70.0, 69.9, 69.3, 50.7. HRMS (ESI) Theory: C13H20N5O6+m/z 342.1408; found 342.1409.

Example 4

Synthesis of 3-(2-(2-(2-(2-azidoethoxy)ethoxy)ethoxy)ethoxy)-2-bromopyridine

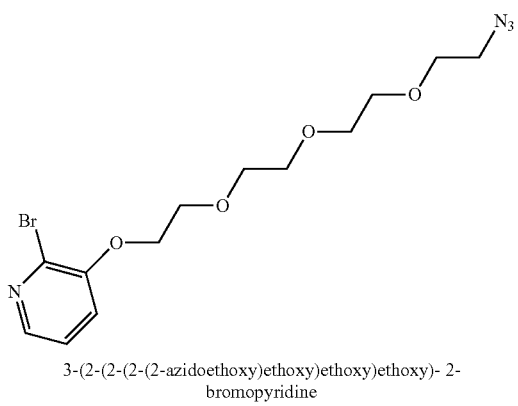

3-(2-(2-(2-(2-azidoethoxy)ethoxy)ethoxy)ethoxy)- 2-bromopyridine

-continued

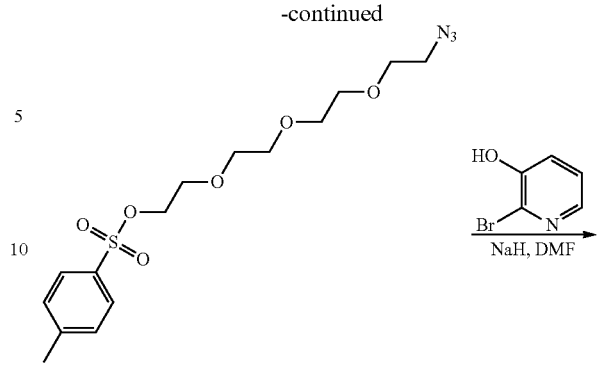

To the suspension of sodium hydride (NaH, 25.7 mg, 0.643 mmol) in dimethylformamide (DMF, 5 mL) at 0° C. was dropwise added a solution of 2-bromopyridin-3-ol (112 mg, 0.643 mmol) in DMF (1 mL), followed by the dropwise addition of the solution of 2-(2-(2-(2-azidoethoxy)ethoxy)ethoxy)ethyl 4-methylbenzenesulfonate (200 mg, 0.536 mmol) in DMF (1 mL). The suspension was held at 0° C. for 10 minutes, then brought to ambient temperature and held for 1 hour, followed by heating to 60° C. for 4 hours. Upon completion of heating, the solvent of the crude reaction mixture was removed in vacuo. The crude reaction was reconstituted in 50 mL of ethyl acetate, washed with 2×50 mL of a aqueous brine solution and the organic layer was dried over magnesium sulfate, filtered and concentrated in vacuo. The crude reaction was purified using reverse-phase HPLC to give 3-(2-(2-(2-(2-azidoethoxy)ethoxy)ethoxy)ethoxy)-2-bromopyridine, TFA (112 mg, 0.229 mmol, 42.7% yield) as a light yellow oil. HRMS ESI m/z (M+H), Theory C13H20BrN4O4 375.0664 found 375.0662; 1H NMR (400 MHz, DMSO-d$_6$) δ 7.97 (dd, J=4.6, 1.5 Hz, 1H), 7.54 (dd, J=8.2, 1.6 Hz, 1H), 7.40 (dd, J=8.1, 4.6 Hz, 1H), 4.24 (dd, J=5.3, 3.9 Hz, 2H), 3.85-3.78 (m, 2H), 3.68-3.62 (m, 2H), 3.62-3.52 (m, 8H), 3.42-3.34 (m, 2H).

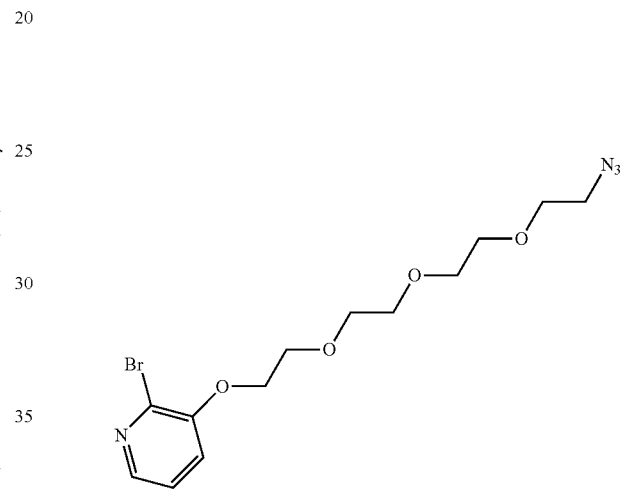

Example 5
Scheme for Synthesis of Trimethylanilium Compound
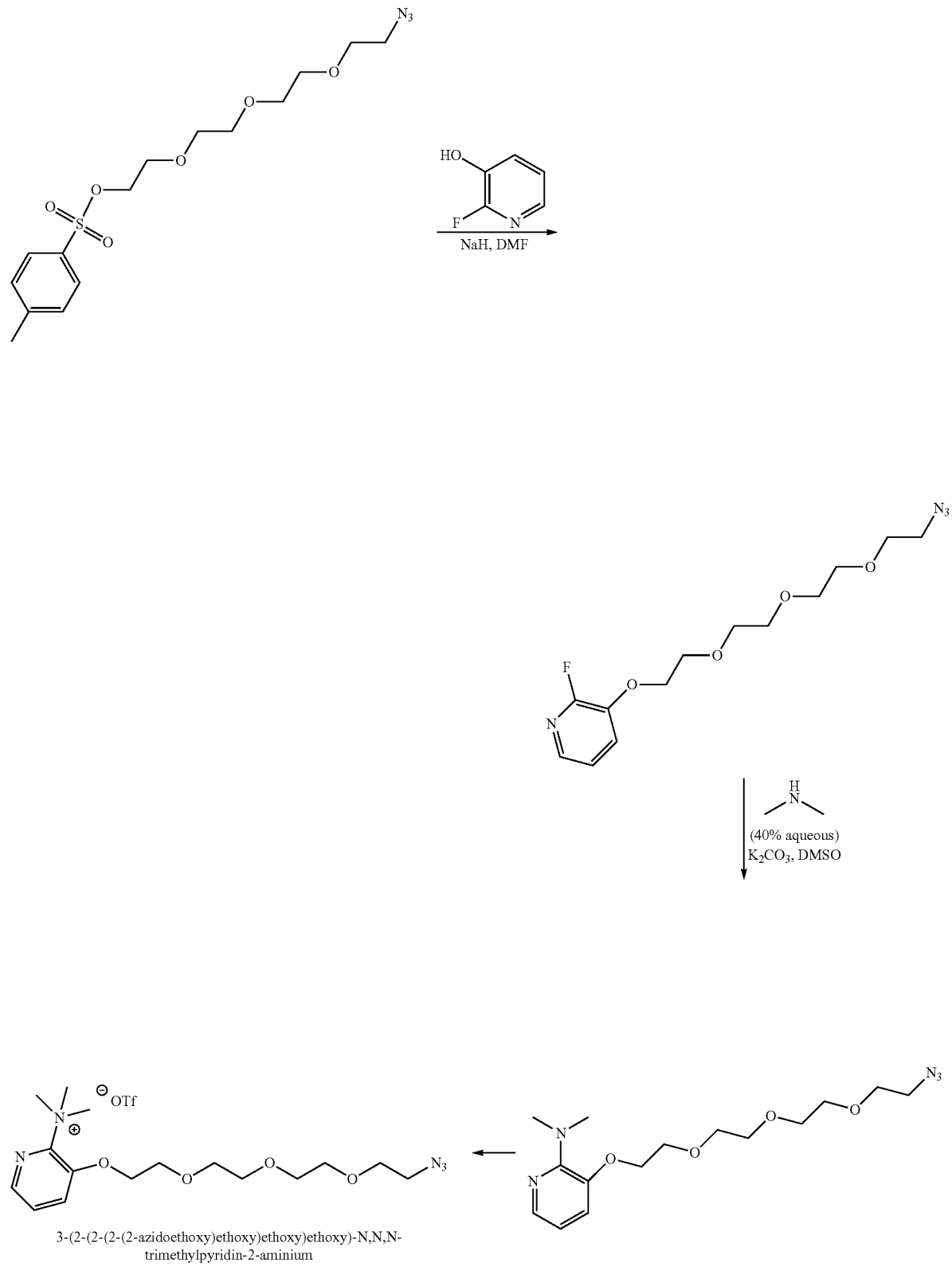
3-(2-(2-(2-(2-azidoethoxy)ethoxy)ethoxy)ethoxy)-N,N,N-trimethylpyridin-2-aminium

Example 6

Synthesis of 3-(2-(2-(2-(2-azidoethoxy)ethoxy)ethoxy)ethoxy)-N,N-dimethylpyridin-2-amine

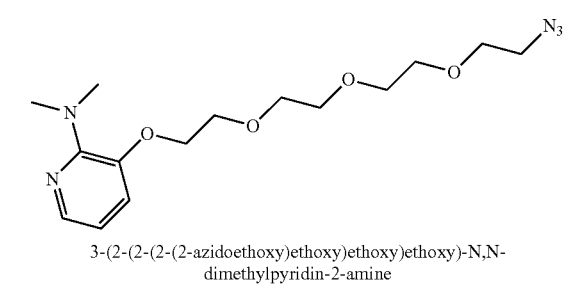

3-(2-(2-(2-(2-azidoethoxy)ethoxy)ethoxy)ethoxy)-N,N-dimethylpyridin-2-amine

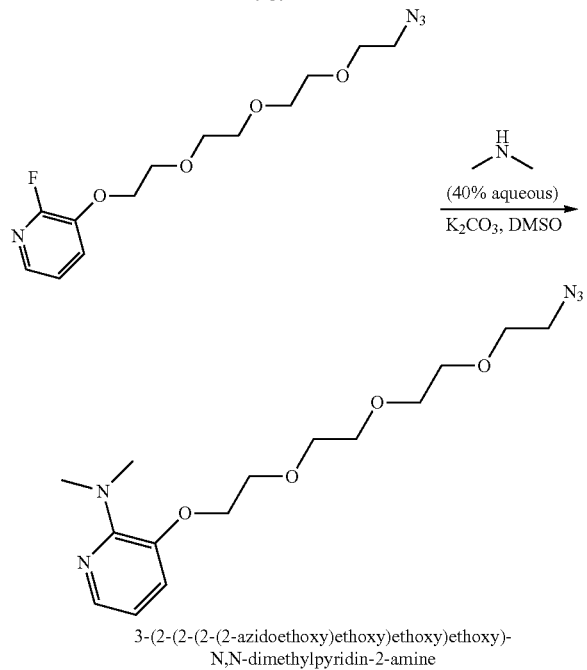

3-(2-(2-(2-(2-azidoethoxy)ethoxy)ethoxy)ethoxy)-N,N-dimethylpyridin-2-amine

A mixture of 3-(2-(2-(2-(2-azidoethoxy)ethoxy)ethoxy)ethoxy)-2-fluoropyridine (160 mg, 0.509 mmol), potassium carbonate (K$_2$CO$_3$, 84 mg, 0.611 mmol) and dimethylamine (40% in water, 0.097 mL, 0.764 mmol) in dimethylsulfoxide (DMSO, 2.5 mL) were heated in a sealed pressure-proof vessel at 110° C. for 14 hours. Upon completion of heating, the solvent of the crude reaction mixture was removed in vacuo. The crude reaction was reconstituted in 50 mL of ethyl acetate, washed with 2×50 mL of a aqueous brine solution and the organic layer was dried over magnesium sulfate, filtered and concentrated in vacuo. The crude reaction was purified using normal-phase chromatography to give 3-(2-(2-(2-(2-azidoethoxy)ethoxy)ethoxy)ethoxy)-N,N-dimethylpyridin-2-amine (140 mg, 0.413 mmol, 81% yield) as a colorless oil. $^1$H NMR (400 MHz, CHLOROFORM-d) δ 7.86 (dd, J=4.9, 1.5 Hz, 1H), 7.02 (dd, J=7.8, 1.5 Hz, 1H), 6.73 (dd, J=7.8, 4.9 Hz, 1H), 4.20-4.07 (m, 2H), 3.98-3.86 (m, 2H), 3.81-3.61 (m, 9H), 3.38 (t, J=5.1 Hz, 2H), 3.13-2.94 (m, 6H), 1.69 (s, 2H). HRMS (ESI) Theory: C15H26N5O4+m/z 340.1980; found 340.1979.

Example 7

Synthesis of 3-(2-(2-(2-(2-azidoethoxy)ethoxy)ethoxy)ethoxy)-N,N,N-trimethylpyridin-2-aminium

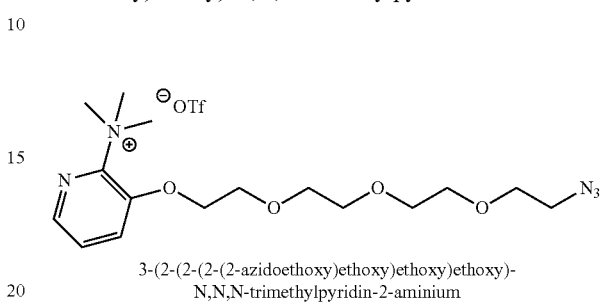

3-(2-(2-(2-(2-azidoethoxy)ethoxy)ethoxy)ethoxy)-N,N,N-trimethylpyridin-2-aminium

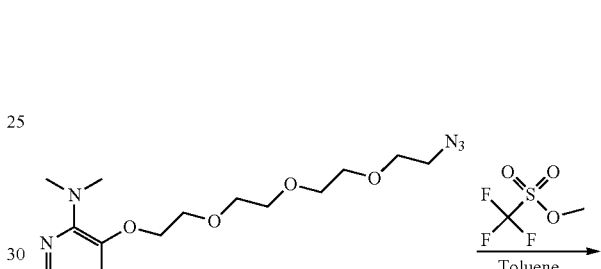

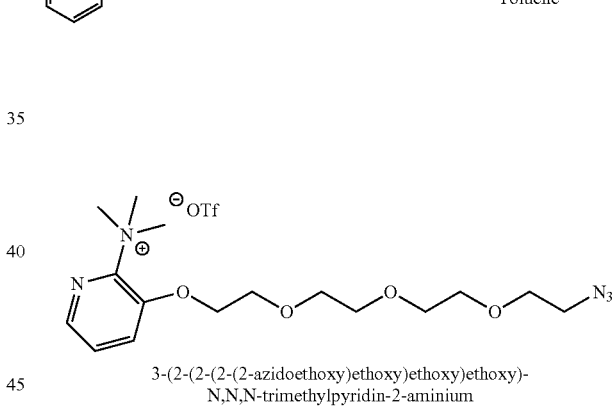

3-(2-(2-(2-(2-azidoethoxy)ethoxy)ethoxy)ethoxy)-N,N,N-trimethylpyridin-2-aminium Methyl trifluoromethanesufonate (0.065 mL, 0.589 mmol) was added to the solution of 3-(2-(2-(2-(2-azidoethoxy)ethoxy)ethoxy)ethoxy)-N,N-dimethylpyridin-2-amine (40 mg, 0.118 mmol) in toluene (1.5 mL) in a sealed container under a steady stream of nitrogen. The reaction mixture was stirred at room temperature over a 14 hour period. The solvent was removed and the resultant residue was washed with 2×10 ml of ether, azeotropically dried with 2×1 ml of dichloromethane and dried under high-pressure vacuum overnight to give 3-(2-(2-(2-(2-azidoethoxy)ethoxy)ethoxy)ethoxy)-N,N,N-trimethylpyridin-2-aminium, trifluoromethanesulfonate salt in quantitative yield as a thick colorless oil. LCMS m/z 354.33; $^1$H NMR (400 MHz, DMSO-d$_6$) δ 8.24-8.17 (m, 1H), 7.98 (d, J=8.3 Hz, 1H), 7.75 (ddd, J=8.2, 4.6, 3.2 Hz, 1H), 4.44 (br. s., 2H), 3.88 (d, J=3.9 Hz, 2H), 3.69-3.45 (m, 21H).

Example 8

The synthesis of the [$^{18F}$]-3-(2-(2-(2-(2-azidoethoxy)ethoxy)ethoxy)ethoxy)-2-fluoropyridine Using 3-(2-(2-(2-(2-azidoethoxy)ethoxy)ethoxy)ethoxy)-N,N,N-trimethylpyridin-2-aminium, trifluoromethanesulfonate Salt

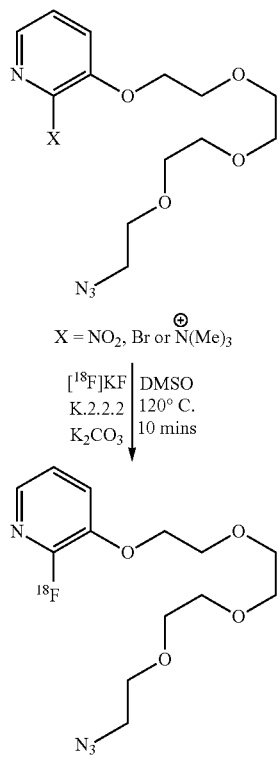

Synthesis of [$^{18}$F]-3-(2-(2-(2-(2-azidoethoxy)ethoxy)ethoxy)ethoxy-2-fluoropyridine An aqueous [$^{18}$F]-Fluoride solution (2.0 ml, 33.3 GBq/900 mCi) was purchased from P.E.T. Net® Pharmaceuticals in West Point Pa. and directly transferred to a Sep-Pak light QMA [The Sep-Pak light QMA cartridge was pre-conditioned sequentially with 5 ml of 0.5 M potassium bicarbonate, 5 ml of deionized water, and 5 ml of MeCN before use.] Upon completion of this transfer, the aqueous [$^{18}$F] fluoride was released from the QMA Sep-Pak by the sequential addition of potassium carbonate (15 mg/ml; 0.1 ml) followed by a mixture of potassium carbonate (30 mg/ml, 0.1 ml), 4,7,13,16,21,24-hexaoxa-1,10-diazabicyclo[8.8.8]hexacosane (15 mg, 0.04 mmol) and 1.2 ml of MeCN. The solvent was evaporated under a gentle stream of nitrogen at 90° C. and vacuum. Azeotropic drying was repeated twice with 1ml portions of acetonitrile to generate the anhydrous K.2.2.2/K[$^{18}$F]F complex. 3-(2-(2-(2-(2-azidoethoxy)ethoxy)ethoxy)ethoxy)-N,N,N-trimethylpyridin-2-aminium, trifluoromethanesulfonate salt (2 mg, 5.6 µmol) was dissolved in 500 microliters of DMSO and added to the dried cryptand. This solution was heated at 120° C. for 10 minutes. After this time the crude reaction mixture was diluted with 3 ml of DI water. The entire contents of the crude reaction mixture was then transferred, loaded and purified using reverse phase HPLC and the following conditions: HPLC Column: Luna C18 250×10 Solvent A: 0.1% TFA in DI water; solvent B: 0.1% TFA in acetonitrile at a flow rate of 4.6 ml/minute using isocratic method 32% B while the UV was monitored at 280 nm. [$^{18}$F]-3-(2-(2-(2-(2-azidoethoxy)ethoxy)ethoxy)ethoxy)-2-fluoropyridine was isolated at the 24 min mark of the chromatogram, and was collect over a 2 minute period. This product was collected into a 100 ml flask that contained 10 ml of DI water and the entire contents were delivered to a Sep-Pak Vac tC18 6 cc 1 g sep pack from Waters. 6.1 GBq/164 mCi of [$^{18}$F]-3-(2-(2-(2-(2-azidoethoxy)ethoxy)ethoxy)ethoxy)-2-fluoropyridine was isolated from this reaction. This was released from the sep-pak using 3 ml of ethanol and this solution was reduced with 98 C heat source, a gentle stream of nitrogen, and vacuum over a 15 minute period until only a film remained in this vial. The final product was reconstituted in 100% 1×PBS buffer and is stable in this media for over 1 hour at 37° C.

The [$^{18}$F]-3-(2-(2-(2-(2-azidoethoxy)ethoxy)ethoxy)ethoxy)-2-fluoropyridine may be used to generate $^{18}$F labeled biologic products by taking advantage of the "click" azide-alkyne reaction with the appropriate biologic containing an alkynes.

Example 9

Production of $^{18}$F-Radiolabeled Protein Using "Click Chemistry"

Figure 5:
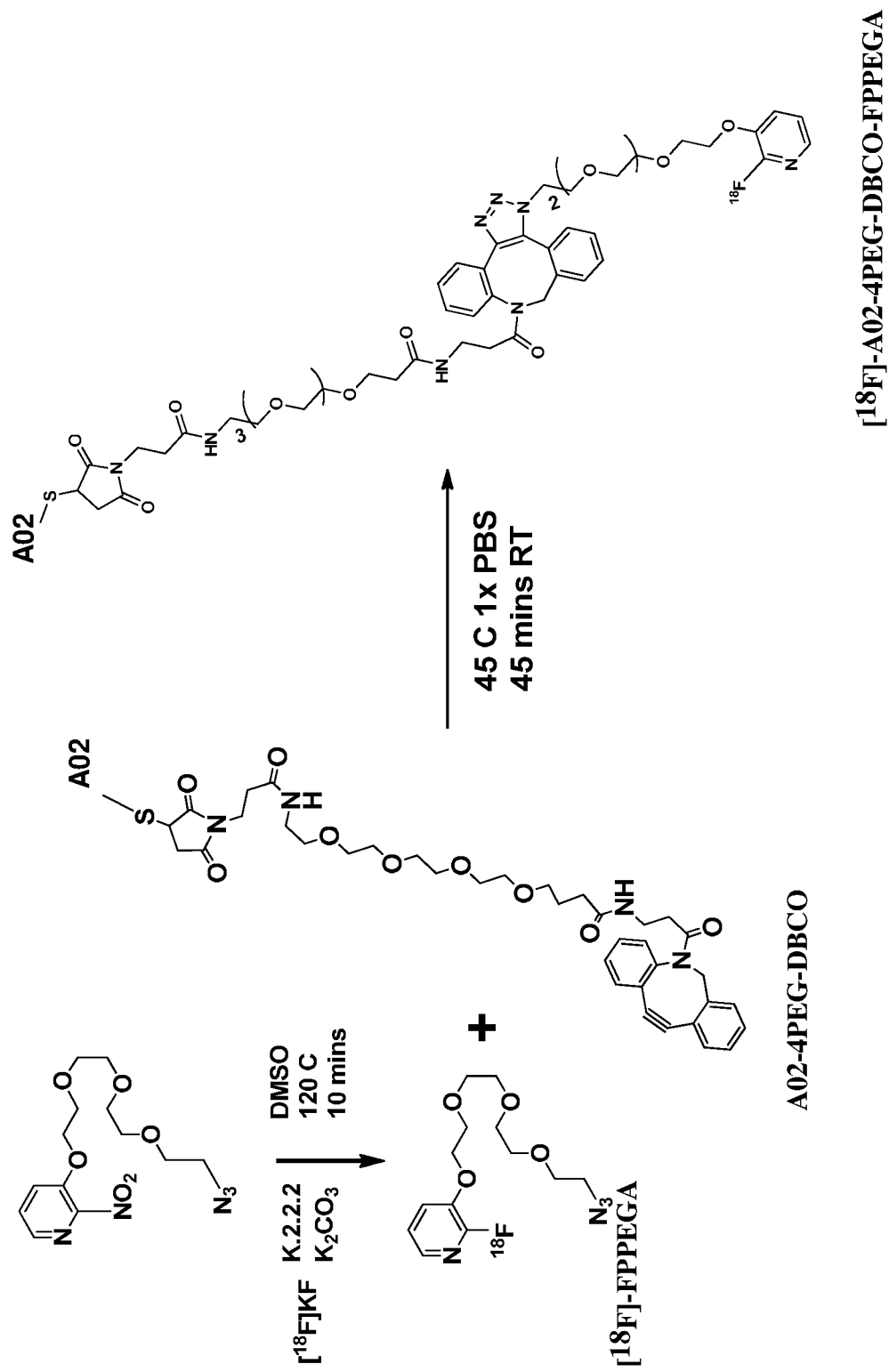
FIG. 5 is a schematic for the production of [$^{18}F$]-radiolabeled-A02-PEG-DBCO-FPPEGA using metal free "click chemistry".

In this example, [$^{18}$F]-3-(2-(2-(2-(2-azidoethoxy)ethoxy)ethoxy)ethoxy)-2-fluoropyridine was used to radiolabel a target protein as illustrated in FIGS. 1 and 5.

A. Fluorination of the 4-PEG-Tosyl-Azide Precursor to Form [$^{18}$F]-FPPEGA 900 mCi of $^{18}$F in $^{18}$O water (3 ml) activity (purchased from IBA Molecular) was transferred directly into a micro vial (no QMA) that contained 4,7,13,16,21,24-hexaoxa-1,10-diazabicyclo[8.8.8]hexacosane (2.8 mg, 7.44 µmol) and potassium carbonate (1.7 mg, 0.012 mmol). An additional 2.0 ml of acetonitrile was transferred into this crude reaction mixture and the entire mixture was azeotropically dried. This was completed by evaporating the solution using a 98° C. oil bath, and applying a gentle stream of N$_2$ and partial vacuum. The solution's volume was reduced to about 2 ml. An additional 2 ml of acetonitrile was added and the process was repeated 3 times over a 40 minute period. When the volume of the liquid was reduced to less than 0.3 ml, a 0.7 ml aliquot of acetonitrile was added and the solution reduced by further azeotropic distillation until the volume was ~0.1 ml. An additional 0.9 ml of acetonitrile was added and this process was completed until a white solid was formed. This process took ~55 minutes. During the final procedure, the vial was removed from the oil bath before the solution had gone to dryness and the residue in the vial was placed under full vacuum (no N$_2$ flow) at room temperature for 20 minutes. Total time for transfer and drying of cryptand mixture was 65 min.

To the dried cryptand mixture was added 3-(2-(2-(2-(2-azidoethoxy)ethoxy)ethoxy)ethoxy)-2-nitropyridine (2 mg, 5.86 µmol) dissolved in 500 microliters of DMSO and this mixture was heated at 120° C. for 10 minutes. After this time the crude reaction mixture was diluted with 3 ml of DI water and the entire contents were then transferred and loaded onto the following HPLC column and conditions: HPLC Column: Luna C18 250×10 mm; Solvent A: 0.1% TFA in DI water; Solvent B: 0.1% TFA in acetonitrile; flow rate 4.6 ml/min; pressure 1820 PSI; isocratic method 32% B; UV—280 nm. The [$^{18}$F]-3-(2-(2-(2-(2-azidoethoxy)ethoxy)

ethoxy)ethoxy)-2-fluoropyridine ([$^{18}$F]-FPPEGA) product was isolated at the 24 minute mark of the chromatogram and was collect over a 2 minute period. This product was collected into a 100 ml flask that contained 15 ml of DI water and the entire contents were delivered to a Sep PakVac tC18 6 cc 1 g sep pack. PN WAT036795. The [$^{18}$F]-FPPEGA was released from the Sep Pak using 2.5 ml of ethanol and this solution was reduced with 98° C. N$_2$ and vacuum over a 15 minute period until dryness. This compound was dissolved in 0.1 ml 1×PBS (phosphate buffered saline). This product was analyzed using a Varian HPLC HPLC Column Luna C18 (2) 4.6×150 mm Solvent A: 0.1% TFA in DI water; Solvent B: 0.1% TFA in acetonitrile; flow rate 1.0 ml/min; gradient method 0 min 90% A 10% B; 15 mins 30% A 70% B; 17 mins 30% A 70% B; 18 mins 90% A 10% B; 20 mins 90% A 10% B; UV—280 nm. 220 mCi of [$^{18}$F]-FPPEGA was isolated.

B. Preparation of E01-4PEG-DBCO

An FBS protein, E01 Adnectin with the following amino acid sequence;

```
                                      (E01; SEQ ID NO: 1)
GVSDVPRDLEVVAATPTSLLISWRAQLSPSFYYRITYGETGGNSPVQEFT

VPNDVMTATISGLKPGVDYTITVYAVTTHGVYFYSPISINYRTPC
``` containing the C-terminal amino acids PC was used.

As maleimide chemistry was used to link the targeting protein to PEG4-DBCO, the E01 Adnectin was first modified by adding a proline followed by a cysteine at its C-terminus using routine recombinant techniques. A 4-fold molar excess of Maleimide-PEG4-DBCO (Click Chemistry Tools) was dissolved in DMSO and added to the purified modified E01 Adnectin in the presence of 1 mM TCEP. Final DMSO concentrations did not exceed 5% in the conjugation mixtures. The conjugation mixture was left at room temperature for one hour before mass spec analysis. After MS confirmation of conjugation, the sample was purified by size-exclusion chromatography using a HiLoad 26/60 Superdex 75 column (GE Healthcare) equilibrated in PBS pH 7.2.

C. Coupling of [$^{18}$F]-FPPEGA to Adnectin 0.2 ml of a 5.4 mg/ml solution of the E01-4PEG-DBCO adnectin solution (prepared as described in Section B) was incubated with 200 mCi of 0.1 ml of the [$^{18}$F]-FPPEGA (Example 1) in 1×PBS buffer. The solution was gently mixed by pipetting the crude reaction up and down several times and was incubated together for 45 minutes at 45° C. or at room temperature. The contents of this crude reaction mixture were purified using a SEC column. Superdex 200 0.5 ml/min 1×PBS buffer and the [$^{18}$F]-E01-4PEG-DBCO-FPPEGA product was isolated at the 37 min mark of the chromatogram over a 2 minute period.

[$^{18}$F]-E01-4PEG-DBCO-FPPEGA was analyzed via SEC with co-injection of non-radioactive standard, RP HPLC using a PLRPS column and gel electrophoresis.

Size Exclusion Chromatography (SEC) was performed with the following parameters:

Superdex 200 column; Solvent 100% 1×PBS buffer; 0.5 ml/min 280 UV;
Reverse phase HPLC
Column: PLRPS 8 micron 1000 A 4.6×250 mm
Solvent A: 0.1% formic acid in DI water
Solvent B: Acetonitrile
Flow rate: 1 ml/min
Pressure: 1351 PSI
Gradient:
0 min 90% A 10% B
30 min 45% A 55% B
32 min 25% A 75% B
36 min 25% A 75% B
50 min 90% A 10% B 15 mCi [$^{18}$F]-E01-4PEG-DBCO-FPPEGA was isolated with a radiochemical purity (RCP) of >99% via both SEC and RP HPLC calculations, and with a specific activity of 0.6 mCi/nmol, when the reaction was conducted at 45° C. When conducting the reaction at room temperature, 5.72 mCi was obtained. Specific activity of the [$^{18}$F]-FPPEGA was 0.512 mCi/nmol and RCP of 85.7% 3 hours post the end of its synthesis, when conducting the reaction at 45° C. or at room temperature, respectively. Specific activity was measured via Nanodrop (see http://www.nanodrop.com). The product co-eluted with non-radioactive standard on both SEC and PLRPS. Gel electrophoresis confirmed an $^{18}$F product consistent with an 11 kDa molecular weight standard.

The $^{18}$F-radiolabeled E01-4PEG-DBCO can be used in a variety of in vitro and/or in vivo imaging applications, including diagnostic imaging, basic research, and radiotherapeutic applications. Specific examples of possible diagnostic imaging and radiotherapeutic applications, include determining the location, the relative activity and/or quantifying of PD-L1 positive tumors, radioimmunoassay of PD-L1 positive tumors, and autoradiography to determine the distribution of PD-L1 positive tumors in a mammal or an organ or tissue sample thereof. In particular, the $^{18}$F-radiolabeled E01-4PEG-DBCO is useful for positron emission tomographic (PET) imaging of PD-L1 positive tumors in the lung, heart, kidneys, liver and skin and other organs of humans and experimental animals. PET imaging using the $^{18}$F-radiolabeled E01-4PEG-DBCO can be used to obtain the following information: relationship between level of tissue occupancy by candidate PD-L1 tumor-treating medicaments and clinical efficacy in patients; dose selection for clinical trials of PD-L1 tumor-treating medicaments prior to initiation of long term clinical studies; comparative potencies of structurally novel PD-L1 tumor-treating medicaments; investigating the influence of PD-L1 tumor-treating medicaments on in vivo transporter affinity and density during the treatment of clinical targets with PD-L1 tumor-treating medicaments; changes in the density and distribution of PD-L1 positive tumors during effective and ineffective treatment.

For example, inhibition of PD-L1 can be calculated based on the change of BP or $V_T$ by equilibrium analysis in the presence of PD-L1 tumor-treating medicament at the various dosing paradigms as compared to the BP or $V_T$ in the unmedicated state. Inhibition curves are generated by plotting the above data vs. the dose (concentration) of PD-L1 tumor-treating medicament. Inhibition of PD-L1 positive tumors is then calculated based on the maximal reduction of PET radioligands $V_T$ or BP that can be achieved by a blocking drug at $E_{max}$, $T_{max}$ or $T_{min}$ and the change of its non-specific volume of distribution ($V_{ND}$) and the BP in the presence of PD-L1 tumor-treating medicaments at the various dosing paradigms as compared to the BP or $V_T$ in the unmedicated state. The ID50 values are obtained by curve fitting the dose-rate/inhibition curves.

D. Alternative Method for Preparing $^{18}$F Labeled Adnectins

A slightly altered method for synthesizing [$^{18}$F]-3-(2-(2-(2-(2-azidoethoxy)ethoxy)ethoxy)ethoxy)-2-fluoropyridine and labelling Adnectins therewith is provided.

900 mCi of fluorine-18 in $^{18}$O water (2 ml) activity was purchased from IBA molecular and delivered into the remote controlled synthesis unit. This sample was transferred directly into a micro vial that contained 4,7,13,16,21,24-hexaoxa-1,10-diazabicyclo[8.8.8]hexacosane (3.2 mg, 8.50 µmol) and potassium carbonate (1.4 mg, 10.13 µmol). An additional 1.5 ml of acetonitrile was transferred into this vial and the entire mixture was azeotropically dried. This solution was then evaporated with by placing the vial into a 90° C. oil bath and applying a gentle stream of $N_2$ and partial vacuum. This was completed by first using partial vacuum for 10 minutes while heating. The total volume of the microvial was reduced to about 2 ml. An additional 2 ml of acetonitrile was added and this process was repeated 3 times over a 40 minute period. When the volume of the liquid was reduced to less than 0.3 ml, 0.7 ml aliquot of acetonitrile was added and the solution reduced by azeotropic distillation until the volume was 0.1 ml, and additional 0.9 MeCN was added and this process was completed until a white solid was formed. During the final procedure, the vial was removed from the oil bath before the solution had gone to dryness and the residue in the vial was placed under full vacuum at room temperature for 20 minutes. 3-(2-(2-(2-(2-azidoethoxy) ethoxy)ethoxy)ethoxy)-2-nitropyridine (2 mg, 5.86 µmol) was dissolved in 500 microliters of DMSO and added to the dried cryptand. This solution was heated at 120° C. for 10 minutes. After this time the crude reaction mixture was diluted with 3 ml of DI water. The entire contents of the crude reaction mixture was then transferred, loaded and purified using reverse phase HPLC and the following conditions: HPLC Column: Luna C18 250×10 Solvent A: 0.1% TFA in DI water; solvent B: 0.1% TFA in acetonitrile at a flow rate of 4.6 ml/minute using isocratic method 32% B while the UV was monitored at 280 nm. [$^{18}$F]-3-(2-(2-(2-(2-azidoethoxy)ethoxy)ethoxy)ethoxy)-2-fluoropyridine was isolated at the 24 min mark of the chromatogram and was collected over a 2 minute period. This product was collected into a 100 ml flask that contained 10 ml of DI water and the entire contents were delivered to a Sep-Pak Vac tC18 6 cc 1 g sep pack from Waters. 224 mCi of [$^{18}$F]-3-(2-(2-(2-(2-azidoethoxy)ethoxy)ethoxy)ethoxy)-2-fluoropyridine was isolated from this reaction. This was released from the sep-pak using 3 ml of ethanol and this solution was reduced with 98° C. heat source, a gentle stream of nitrogen, and vacuum over a 15 minute period until only a film remained in this vial. The final product was reconstituted in 100% 1×PBS buffer and is stable in this media for over 1 hour at 37 C. Using [$^{18}$F]-3-(2-(2-(2-(2-azidoethoxy)ethoxy) ethoxy)ethoxy)-2-fluoropyridine generated several F-18 labeled biologic products by taking advantage of "click" azide-alkyne reaction with the appropriate biologic containing an alkyne.

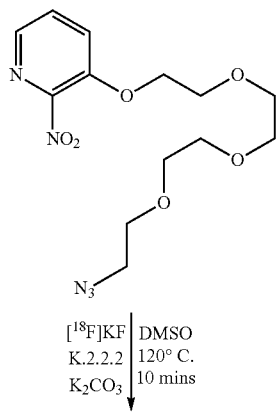

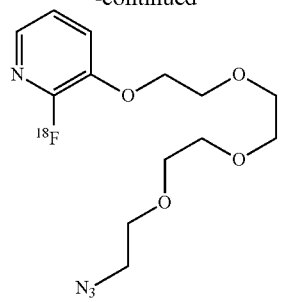

Synthesis of [$^{18}$F]-3-(2-(2-(2-(2-azidoethoxy)ethoxy)ethoxy)ethoxy-2-fluoropyridine Example 10

In Vitro Differentiation of PD-L1-Positive Cells from PD-L1-Negative Cells with an Anti-PD-L1 Adnectin Imaging Agent In this experiment, the $^{18}$F-radiolabeled E01-4PEG-DBCO was tested for its ability to discriminate between PD-L-positive cells and PD-L-negative cells in vitro.

$1\times10^6$ PD-L-positive L2987 human lung carcinoma cells or PD-L-negative HT-29 human colorectal adenocarcinoma cells were placed into 5 mL culture tubes (n=3 tubes per condition). $^{18}$F-radiolabeled E01-4PEG-DBCO solution was prepared in PBS+0.5% BSA at a concentration of 300 nCi/200 µL. Portions of this solution were supplemented with either cold (unlabeled) E01 Adnectin or cold (unlabeled) Adnectin (control) to a final concentration of 450 nM. Cell samples were centrifuged for 5 min at 200×g and then resuspended in 200 µL of the appropriate $^{18}$F-radiolabeled E01-4PEG-DBCO solution and incubated on ice for 1 hour. After the incubation period, cell samples were centrifuged at 200×g and the supernatant was discarded. Cell pellets were resuspended in 1 mL PBS+0.5% BSA and the wash procedure repeated for a total of 3 washes. Following the final wash, cells were again centrifuged at 200×g and the supernatant was discarded. The radioactivity of the remaining cell pellets was then measured by gamma counter.

The results indicated that ell labeling was specific, as evidenced by differential association of $^{18}$F-radiolabeled E01-4PEG-DBCO with PD-L-positive L2987 cells compared to PD-L-negative HT-29 cells (cell associated radioactivity was 44.6× higher in PD-L-positive L2987 cells). Specificity was further confirmed as evidenced by a marked reduction in cell-associated $^{18}$F-radiolabeled E01-4PEG-DBCO when co-incubated with excess 450 nM cold (unlabeled) E01 Adnectin (99.6% reduction). Cell associated $^{18}$F-E01 was minimally reduced (9.9% reduction, not significant) when cells were co-incubated with 450 nM cold (unlabeled) non-PD-L1 binding adnectin.

Taken together, these results demonstrate the ability of the $^{18}$F-radiolabeled E01-4PEG-DBCO to differentiate PD-L1(+) vs. PD-L1(−) cells in vitro.

Example 11

Distinguishing PD-L1-Positive Tumors from PD-L1-Negative Tumors In Vivo with an Anti-PD-L1 Adnectin Imaging Agent In this experiment, the $^{18}$F-radiolabeled PD-L1 Adnectin with the following amino acid sequence:

(A02; SEQ ID NO: 2)
EVVAATPTSLLISW<u>SYDGPIDRY</u>YRITYGETGGNSPVQEFTV<u>PPDQKTAT</u>
ISGLKPGVDYTITVYA<u>VRLEEAHYNREFPI</u>SINYRTPC was produced as described in Example 9, was tested for the ability to discriminate between PD-L1-positive tumors and PD-L-negative tumors in mice.

Mice bearing bilateral xenograft tumors were produced by introducing 1×10$^6$ PD-L1(+) L2987 human lung carcinoma cells and 1.5×10$^6$ PD-L1(−) HT-29 human colon carcinoma cells subcutaneously on opposite sides of the mouse. Once tumors reached approximately 300 mm$^3$ (approximately 2-3 weeks after cell implantation) animals were selected for imaging. For imaging, animals were placed under anesthesia with 2% isoflurane and tail vein catheters were installed. Mice were then placed into a custom animal holder with capacity for 4 animals, where they remained under anesthesia for the duration of the study. The animal holder was transferred to the microPET® F120™ scanner (Siemens Preclinical Solutions, Knoxville, Tenn.). The axial field of view of this instrument is 7.6 cm. With this limitation, animals were positioned such that the scanning region was from immediately in front of the eyes to approximately the base of the tail.

A 10-minute transmission image was first acquired using a $^{57}$Co point source for the purpose of attenuation correction of the final PET images. Following the transmission scan, radiotracer solutions were administered via the previously installed tail vein catheters and a 2 hour emission image was acquired. Injected radiotracer solutions consisted of either approximately 200 µCi $^8$F-radiolabeled A02 or 200 µCi $^{18}$F-radiolabeled A02 supplemented with 3 mg/kg final concentration of cold, unlabeled A02 Adnectin (based on individual animal weight). All injections were formulated in 200 µL saline prior to injection. Exact injected doses were calculated by taking direct measurement of the formulated dose and subtracting the radioactivity remaining in the syringe and the tail vein catheter.

Images were reconstructed using a maximum a posteriori (MAP) algorithm with attenuation correction using the collected transmission images and corrected for radioisotope decay. In the final images, regions of interest (ROIs) were drawn around the tumor boundary using ASIPro software (Siemens Preclinical Solutions). Time-activity curves were calculated for each ROI to yield a quantitative view of radiotracer within the tumor volume over the course of the 2 hour emission image. For final comparison, individual time-activity curves were normalized based on the injected radiotracer dose for each specific animal. Radiotracer uptake was compared across tumors using the final 10 minutes of each time-activity curve (1 hour 50 minutes-2 h post-radiotracer injection). Using this methodology, radiotracer uptake in PD-L1(+) L2987 xenografts was 3.05× that seen PD-L1(−) HT-29 xenografts in animals receiving only the $^{64}$Cu-A01 radiotracer. In animals co-injected with the $^{18}$F-radiolabeled A02 radiotracer and 3 mg/kg unlabeled A02 Adnectin uptake in the PD-L1(+) L2987 xenografts was only 1.04× that seen in PD-L1(−) HT-29 xenografts.

Figure 2:
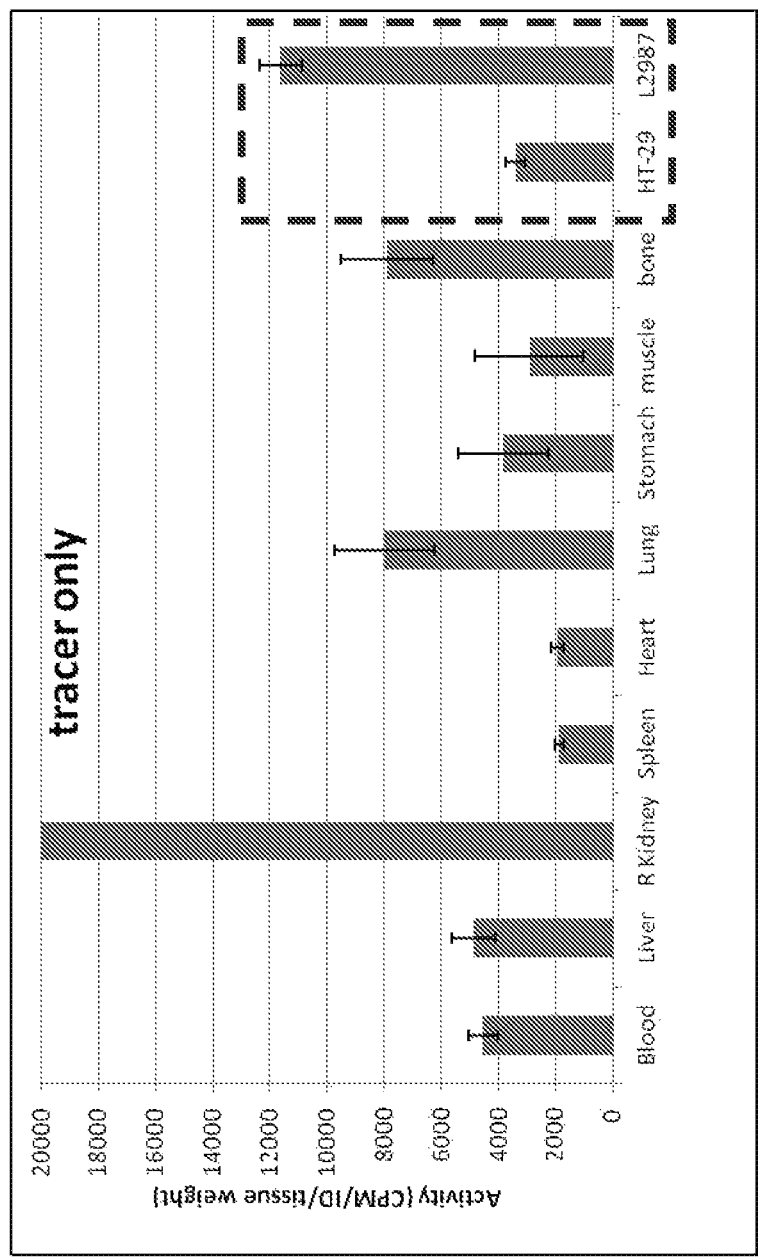
FIG. 2 is a bar graph depicting the tissue distribution of the $^{18}F$-A02 radiotracer in mice bearing bilateral PD-L1(+) L2987 and PD-L1(−) HT-29 xenografts as measured ex vivo by gamma counter.

For some studies, animals were sacrificed via cervical dislocation immediately following imaging. Necropsy was then performed on the animals, and individual tissues were collected (blood, heart, lung, liver, spleen, kidney, muscle, stomach, bone, L2987 tumor, and HT-29 tumor) into pre-weighed tubes. All tissues were then weighed again to determine the weight of each tissue. The radioactivity in each tissue was then directly measured ex vivo using a Perkin-Elmer Wizard3 gamma counter. For all tissues, measured values in counts per minute (CPM) were normalized to the injected radioactive dose for the individual animals and corrected for radioactive decay. These results were then plotted to show the biodistribution of the radiotracer as shown in FIG. 2.

These results demonstrate clear differential uptake of the radiotracer in PD-L1(+) L2987 xenografts compared to PD-L1(−) HT-29 xenografts. Furthermore, the only tissue with higher PD-L1 uptake was the kidney, which is expected as clearance of the $^{18}$F-radiolabeled A02-4PEG-DBCO Adnectin is expected to be via kidney filtration based on the molecular weight of the molecule.

Taken together, these results provide direct visualization of differentiation of PD-L1(+) versus PD-L1(−) xenograft tumors in vivo. Specificity was further demonstrated by co-injection of 3 mg/kg unlabeled anti-PD-L1 A02 adnectin, resulting in a reduction of radiotracer uptake in PD-L1(+) tumors to the level of PD-L1(−) xenografts. A maximum radiotracer uptake ratio of 3.53:1 in hPD-L1(+) L2987 xenografts vs. hPD-L1(−) HT-29 xenografts using the $^{18}$F-A02 Adnectin radiotracer was obtained. This further validates the use of anti-PD-L1 adnectins for visualization of PD-L1 tissue expression using PET imaging. Similar experiments using $^{18}$F as the radionuclide were conducted in mice, and similar results were obtained, reaching.

Example 12

In Vivo Imaging in Cynomolgus Monkeys

The $^{18}$F-radiolabeled E01 imaging agents also showed similar results when performed in cynomolgus monkeys. In these studies, the $^{18}$F-E01 anti-PD-L1, produced as described in Example 9, was tested for the ability to produce high-contrast images in cynomolgus monkeys. The anti-PD-L1 adnectins described here maintain high affinity for cynomolgus PD-L1 (but have low affinity for rodent PD-L1). Furthermore, as the cynomolgus monkeys do not contain PD-L1(+) tumors as in mouse models, imaging performance was assessed primarily on the background levels measured in the images in the context of endogenous PD-L1 expression (with low background enabling the potential for high-sensitivity detection of PD-L1(+) tissues). In these studies, background levels in the resulting PET images were very low, with notable radiotracer accumulation noted mainly in the kidneys, spleen, and bladder.

Cynomolgus male monkeys with a previously installed vascular access port (VAP) were anesthetized with 0.02 mg/kg atropine, 5 mg/kg Telazol and 0.01 mg/kg buprenorphine I.M. (all drawn into a single syringe). An i.v. catheter is then placed in the cephalic vessel for fluid administration during the imaging procedure to maintain hydration. Animals were intubated with an endotracheal tube—usually 3.0 mm and transferred to the imaging bed of a microPET® F220™ PET instrument (Siemens Preclinical Solutions, Knoxville, Tenn.). Anesthesia was maintained with isoflurane and oxygen and I.V. fluids (LRS) were administered at a rate of 6 ml/kg/hr during the imaging procedure. As the axial field of view of the microPET® F220™ instrument is only 7.6 cm, images over 5 distinct bed positions were acquired to create a composite image of the animals from just above the heart through approximately the pelvis.

For each field of view, a 10 minute transmission image was first acquired using a $^{57}$Co point source for the purpose of attenuation correction of the final PET images. Once transmission images were acquired for all bed positions, approximately 1.5 mCi (approximately 0.015 mg/kg) of the $^{18}$F-E01 adnectin radiotracer was administered via the installed VAP. Five minute duration emission scans were then sequentially acquired for each bed position, beginning at position 1 centered approximately at the heart and moving toward the pelvis of the animal. Once images were acquired at each position (1 through 5), the imaging bed was moved back to bed position 1 and the process was repeated. Using this procedure, a total of 5 distinct images were acquired for each bed position over the duration of the imaging study.

Figure 3:
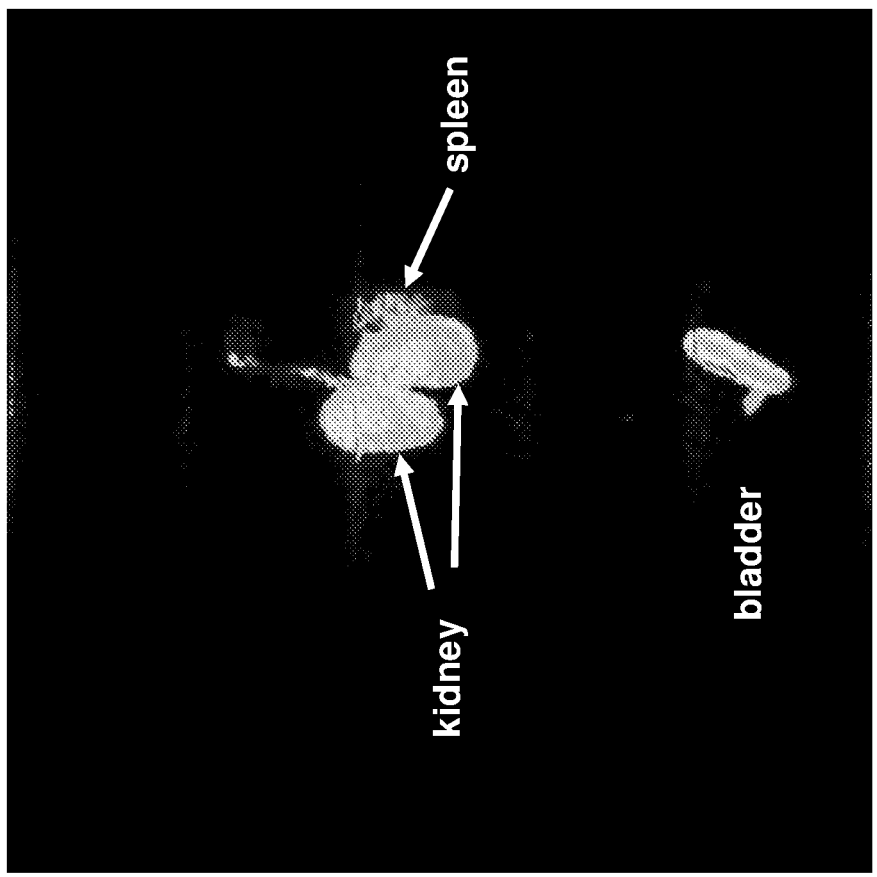
FIG. 3 is a composite image of $^{18}F$-E01 distribution in cynomolgus monkeys.

Individual images were reconstructed using a filtered back projection (FBP) algorithm with attenuation correction using the collected transmission images and corrected for radioisotope decay. Final composite images were then produced by aligning images from all 5 bed positions obtained from a single pass (i.e. a single composite image was produced from each set of sequential images from bed positions 1 through 5) covering the duration of the imaging study (FIG. 3). Final images were visually inspected to note areas of visible radiotracer uptake (i.e. spleen, kidney, bladder) and background tissue (muscle). Background accumulation of $^{18}$F-E01 adnectin was very low, with little signal visible in background tissues such as muscle. Additionally, uptake was verified in the spleen, which is believed to be PD-L1(+) based on mRNA expression. Thus, studies in cynomolgus monkeys demonstrate the potential for high-sensitivity PD-L1 imaging in the context of endogenous PD-L1.

In aggregate, PET studies in rodent and cynomolgus monkey show that $^{18}$F labeled proteins produced according to the methods described herein provide strong and specific probes for in vivo labeling of target positive tissues with the potential for high-sensitivity detection of tissues with low level target expression.

Example 13

In Vitro Autoradiography with [$^{18}$F]-A02 Anti-PD-L1 Adnectin

Human lung tumor tissues were embedded in OCT and chilled in 2-methylbutane for 2-5 minutes until frozen. The samples were stored in −80° C. degree freezer until use. Human xenograft tissues were also included in the assay. Mice bearing bilateral xenografts were produced by introducing 4×10$^6$ PD-L1(+) L2987 cells and 1.5×10$^6$ PD-L1(−) HT-29 t cells subcutaneously into opposite flanks of nu/nu mice. Once resulting xenograft tumors reached appropriate size (approx. 200-300 mm$^3$) mice were anesthetized with 2% isoflurane and sacrificed via cervical dislocation. Fresh tumor tissues were excised, immersed into OCT and chilled in 2-methylbutane for 2-5 minutes until frozen. The tissues were then wrapped in foil/ZIPLOC® bag and stored at −80° C. until use. For all tissues (human lung tumor and xenografts) sections of 5 μm thickness (collected as 2 sections/slide) were cut using a cryostat, thaw-mounted on glass microscope slides, and allowed to air dry for approximately 30 minutes.

Blocking studies with cold (unlabeled) A02 adnectin at 0.025 nM, 0.25 nM, 2.5 nM and 25 nM respectively and 25 nM non-PD-L1 binding adnectin were conducted using the following conditions. The individual slides, 1 slide per concentration, were placed in plastic slide cassettes and pre-incubated in Dako serum-free protein block solution for 30 minutes. Slides were then transferred to glass slide incubation chambers for further incubation. Separately, a stock solution of 0.25 nM $^{18}$F-A02 adnectin was produced by diluting 10.6 μl of the original stock radioligand solution (7064 nM at the time of experiment) with 300 ml of PBS+0.5% BSA. From this stock solution, 40 ml was added to each incubation chamber. One of these chambers contained only the radioligand buffer solution, which is referred to as the total binding section. Other incubation chambers received 40 ml of this stock solution along with the relevant concentration of blocking compound (unlabeled A02 adnectin at 0.025 nM, 0.25 nM, 2.5 nM, or 25 nM or unlabeled adnectin at 25 nM). Slides were incubated in the individual buffer solutions for 1 hour at room temperature to reach maximum binding. After incubation, slides from each treatment group were removed from the incubation solutions and placed in an ice-cold wash buffer (PBS+0.5% BSA) for 3 minutes and rinsed 4 separate times. Slides were then dried under a stream of cold air for approximately 30 minutes. The air-dried slides were exposed by placing the slides onto an imaging plate (BAS-SR 3545S) overnight at room temperature. The imaging plate was scanned using the bioimaging analyzer (Fujifilm Fluorescent Image Analyzer, FLA-9000). The pixel size of the autoradiogram images was 100 am. Image analysis was performed using the Multi-Gauge software. The regions of interest (ROIs) were drawn to surround the entire tumor tissue in all study groups. Autoradiography signal from tissue-associated radioactivity was quantified from these ROIs.

The apparent displacement of the $^{18}$F-A02 adnectin radioligand when compared to the total binding sections was determined for 4 different concentrations (0.025 nM, 0.25 nM, 2.5 nM and 25 nM) of unlabeled A02 adnectin in both human lung tumor sections as well as human xenograft sections. A dose dependent displacement of $^{18}$F-A02 was seen in all tissue sections with the addition of unlabeled A02 adnectin. 25 nM non-PD-L1 binding adnectin showed minimal blockade in all tissues compared to total binding (FIG. 4A).

Figure 4:
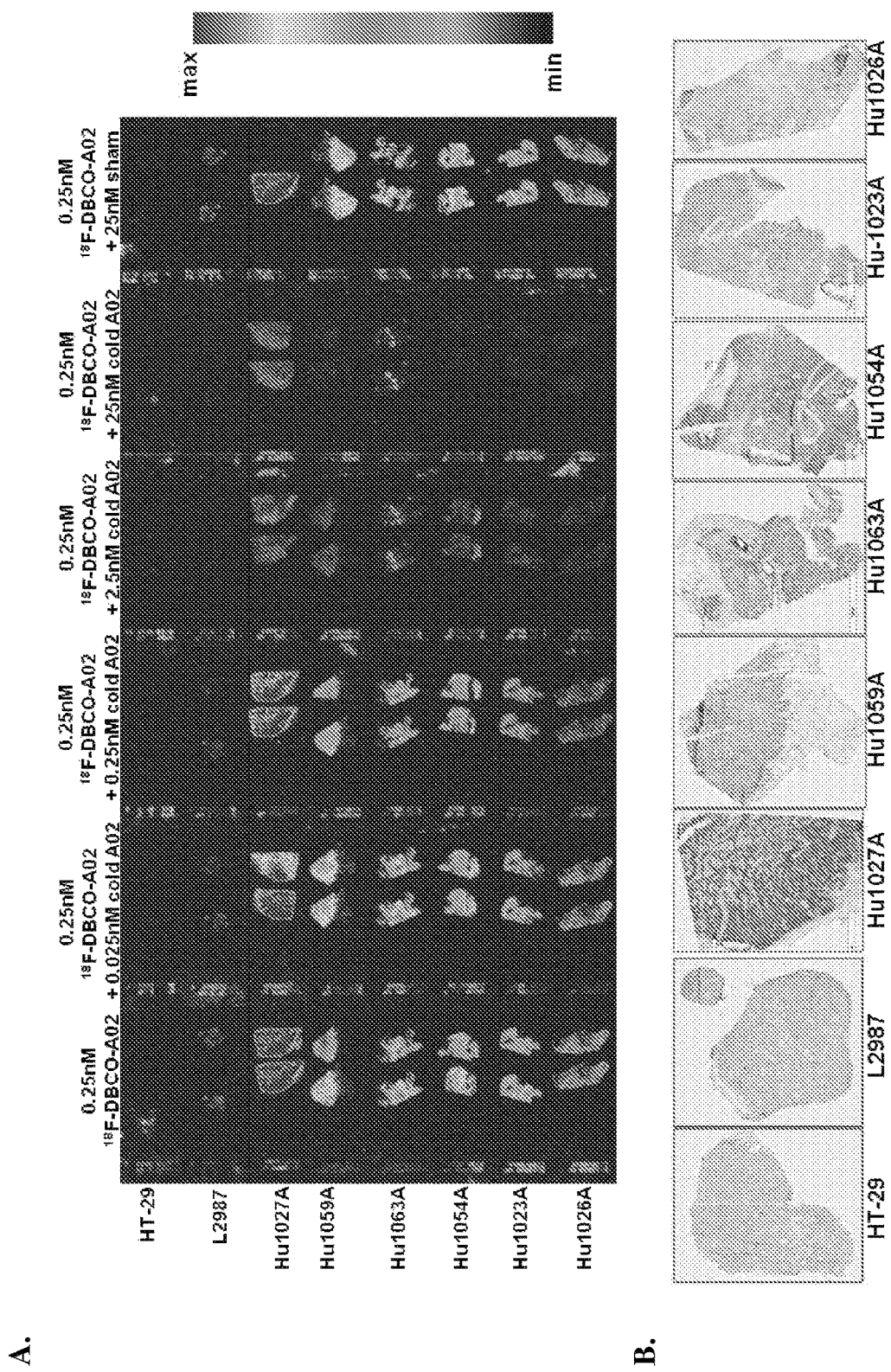
FIGS. 4A and B depict images of in vitro autoradiography of $^{18}F$-A02 in xenograft and human lung tissues.

Serial 5 μm tissue sections from each tissue were subjected to an anti-human-PD-L1 immunohistochemical procedure to verify the level of PD-L1 antigen expression in the samples (FIG. 4B).

Taken together, these results provide direct visualization of PD-L1 in both human lung tumor samples as well as human xenograft tissues. The level of radioligand binding in the individual tissues corresponds with the intensity of PD-L1 staining of frozen sections by IHC. In addition, the dose dependent blockade of the receptor with unlabeled anti-PD-L1 A02 adnectin (and lack of blockade with unlabeled non-PD-L1 binding adnectin), further validates the use of $^{18}$F-A02 for visualization of PD-L1 tissue expression using PET imaging.

Example 14

Automated preparation of [$^{18}$F]-3-(2-(2-(2-(azido-ethoxy)ethoxy)ethoxy)ethoxy)-2-fluoropyridine According to the General Procedure for Radiosynthesis Using Commercial GE TRACERlab FX2 N Synthesis Unit

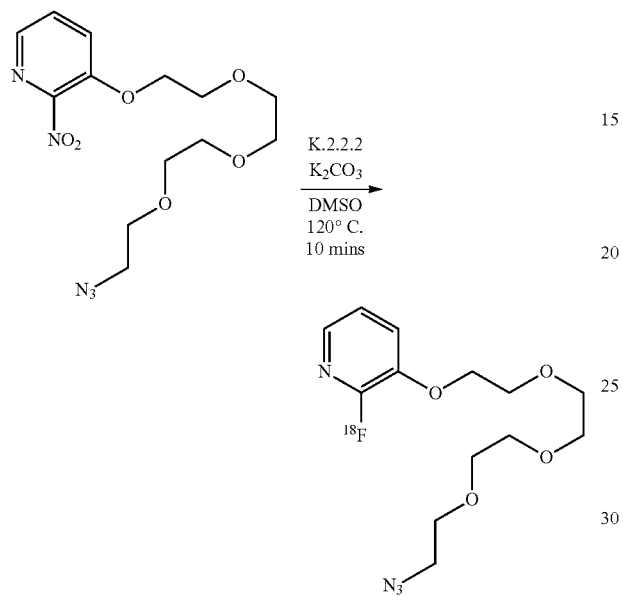

Figure 6:
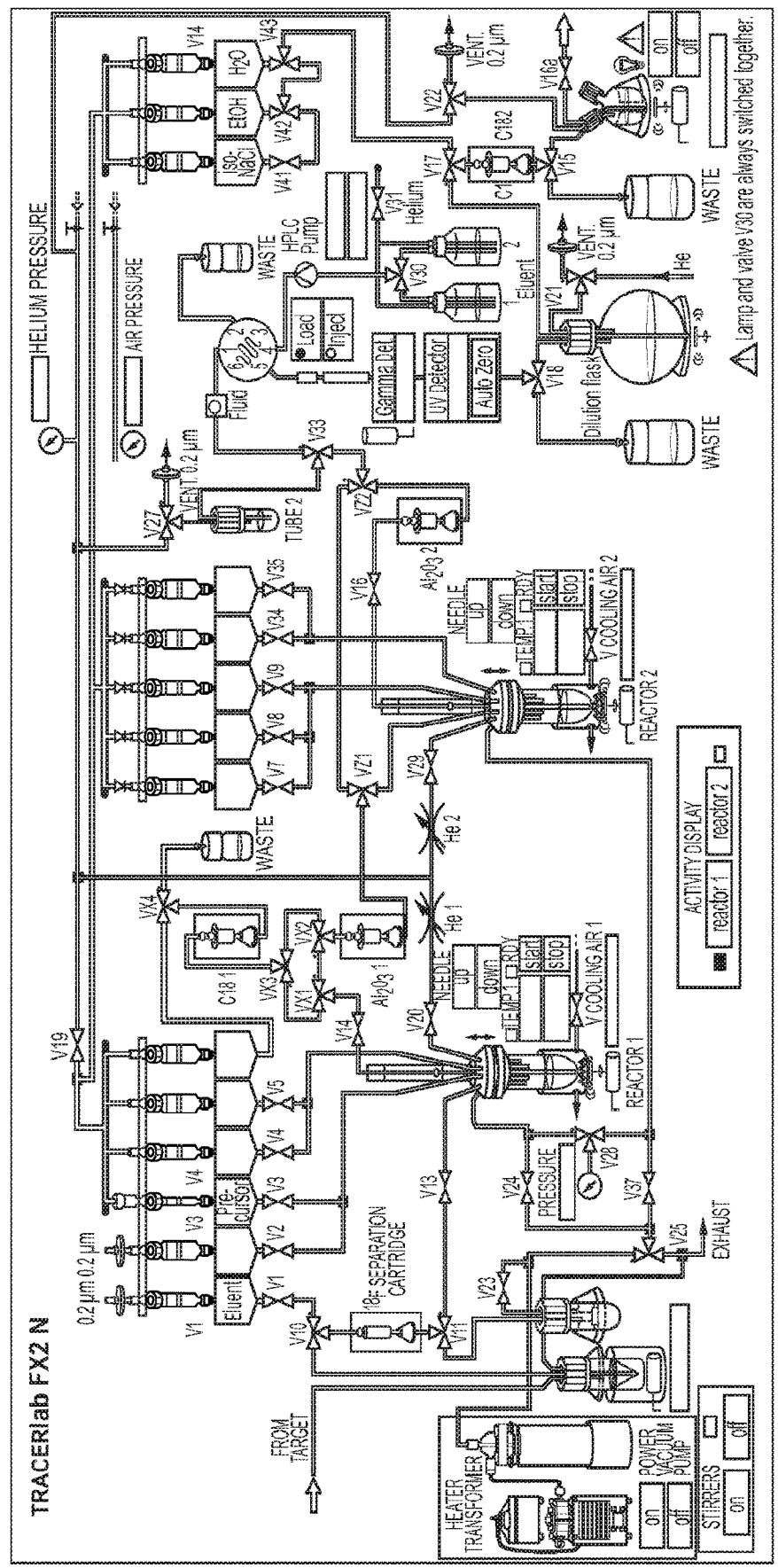
FIG. 6 is a schematic of the GE TRACERlab FX2 N Synthesis module for automated synthesis of [$^{18}F$]-FPPEGA.
Figure 7:
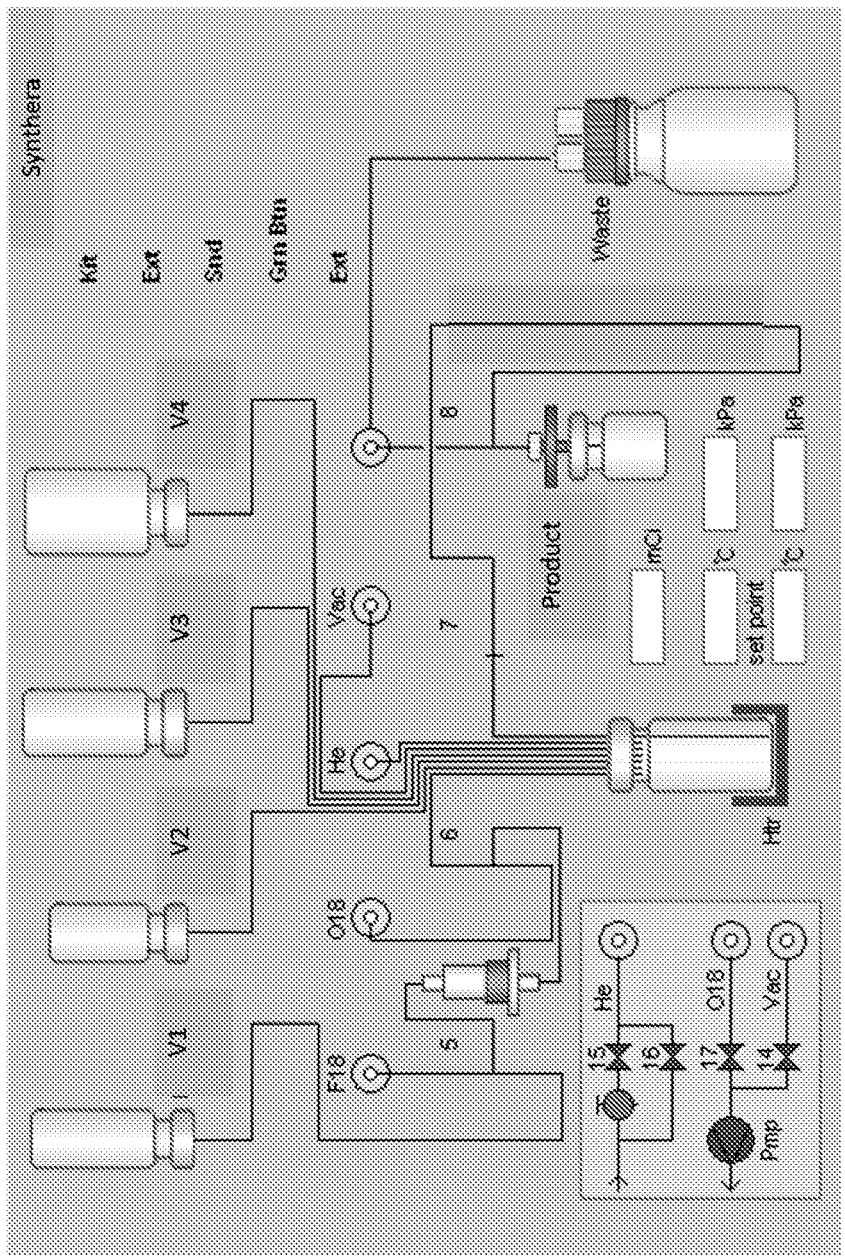
FIG. 7 is a schematic of the Synthera Synthesis module (IBA) for automated synthesis of [$^{18}F$]-FPPEGA.

Procedure:

The automated synthesis of [$^{18}$F]-3-(2-(2-(2-(2-azidoethoxy)ethoxy)ethoxy)ethoxy)-2-fluoropyridine was carried out using a non-cassette type GE TRACERlab FX2 N Synthesis module. The setup of the synthesis unit is summarized in Table 1 and FIG. 6. The aqueous [$^{18}$F]-Fluoride solution (2.0 ml, 29.6 GBq/800 mCi) was delivered to a Sep-Pak light QMA [The Sep-Pak light QMA cartridge was pre-conditioned sequentially with 5 ml of 0.5 M potassium bicarbonate, 5 ml of deionized water, and 5 ml of acetonitrile before use.] Upon completion of this transfer, the aqueous [$^{18}$F] fluoride was released from the QMA Sep-Pak by the addition of the elution mixture (from "VI") into the reactor. The solvent was evaporated under a gentle stream of nitrogen and vacuum. The solution of precursor (from "V3") was added to the dried cryptand residue and this reaction mixture was heated 120° C. for 10 minutes. Then 4 ml of distilled water (from "V4") was added to the crude reaction mixture in the reactor and the mixture is transferred to the 5 ml sample injection loop of the semi-preparative HPLC via a liquid sensor which controls the end of the loading. The mixture was loaded onto the semi-preparative HPLC column (Luna C18(2). 250×10 mm, Phenomenex). A mixture of 35% acetonitrile in an aqueous 0.1% trifluoroacetic acid solution was flushed through the column at a rate of 4.6 ml per minute. The product was collected from this HPLC column into the dilution flask which contained 15 ml distilled water and its entire contents were transferred to a tC18 1 gram, solid phase extraction cartridge. 352 mCi (13 GBq) of [$^{18}$F]-3-(2-(2-(2-(2-azidoethoxy)ethoxy)ethoxy)ethoxy)-2-fluoropyridine was released from this cartridge (from "V14") with 3 ml of ethanol and may be used to generate $^{18}$F labeled biologic products by taking advantage of "click" azide-alkyne reaction with the appropriate biologic containing an alkynes.

TABLE 1

| Vial 1 (V1) | 16 mg K.2.2.2, 3 mg Potassium carbonate, dissolved in 0.1 ml of distilled water and 1.4 ml of acetonitrile |
| --- | --- |
| Vial 3 (V3) | 2 mg 3-(2-(2-(2-(2-azidoethoxy)ethoxy)ethoxy)ethoxy)-2-nitropyridine in 0.5 ml DMSO |
| Vial 4 (V4) | 4 ml of distilled water |
| Vial 14 (V14) | 3 ml of 100% ethanol |
| Dilution Flask | 15 ml of distilled water |
| Cartridge 1 (C1) | tC18 6 cc 1 g sep pack |
| HPLC Column | Luna C18(2), 250 × 10 mm, 5 µm, Phenomenex |
| HPLC Solvent | 35% acetonitrile in an aqueous 0.1% trifluoroacetitic acid solution |
| HPLC flow | 4.6 ml/min |

Example 15

Automated preparation of [$^{18}$F]-3-(2-(2-(2-(2-azido-ethoxy)ethoxy)ethoxy)ethoxy)-2-fluoropyridine According to the General Procedure for Radiosynthesis Using a Commercial IBA Synthera Synthesis Unit

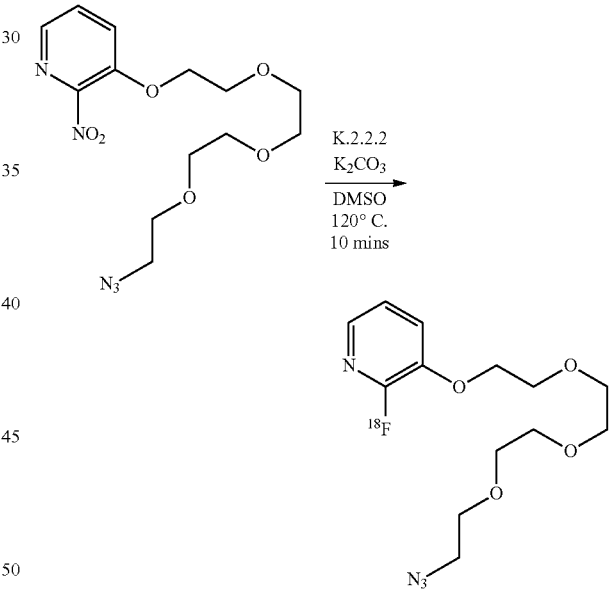

Procedure:

The automated synthesis of [$^{18}$F]-3-(2-(2-(2-(2-azidoethoxy)ethoxy)ethoxy)ethoxy)-2-fluoropyridine was carried out using a cassette type IBA Synthera Synthesis module and an appropriately assembled integrator fluidic processor kit. The integrator fluidic processor (IFP) kit was loaded with appropriate precursors for this synthesis and is summarized in Table 2. The purification was performed on an Varian HPLC unit. The filling of the injection loop of the HPLC was controlled by a steady stream of nitrogen on the HPLC unit. The setup of both automates are summarized in Table 2. The aqueous [$^{18}$F]-Fluoride solution (2.0 ml, 29.6 GBq/800 mCi) was delivered to a Sep-Pak light QMA [The Sep-Pak light QMA cartridge was pre-conditioned sequentially with 5 ml of 0.5 M potassium bicarbonate, 5 ml of deionized water, and 5 ml of acetonitrile before use.] Upon completion of this transfer, the aqueous [$^{18}$F] fluoride was released from the QMA Sep-Pak by the addition of the elution mixture (from "V1") into the reactor. The solvent was evaporated under a gentle stream of nitrogen and vacuum. The solution of precursor (from "V2") was added to the dried cryptand residue and this reaction mixture was heated 120° C. for 10 minutes. Then 3 ml of distilled water (from "V4") was added to the crude reaction mixture in the reactor and the mixture was transferred to the 5 ml sample injection loop of the semi-preparative HPLC via a liquid sensor which controls the end of the loading. The mixture was loaded onto the semi-preparative HPLC column (Luna C18(2). 250×10 mm, Phenomenex). A mixture of 35% acetonitrile in an aqueous 0.1% trifluoroacetic acid solution was flushed through the column at a rate of 4.6 ml per minute. The product was collected from this HPLC column into the dilution flask which contained 15 ml distilled water and its entire contents were transferred to a tC18 1 gram, solid phase extraction cartridge. 325 mCi (12 GBq) of [$^{18}$F]-3-(2-(2-(2-(2-azidoethoxy)ethoxy)ethoxy)ethoxy)-2-fluoropyridine was released from this cartridge with 3 ml of ethanol and may be used to generate $^{18}$F labeled biologic products by taking advantage of "click" azide-alkyne reaction with the appropriate biologic containing an alkynes.

TABLE 2

| | |
|---|---|
| Vial 1 (V1) | 22 mg K.2.2.2, 4 mg Potassium carbonate, dissolved in 0.3 ml of distilled water and 0.3 ml of acetonitrile |
| Vial 2 (V2) | 2 mg 3-(2-(2-(2-(2-azidoethoxy)ethoxy)ethoxy)eth-oxy)-2-nitropyridine in 0.5 ml DMSO |
| Vial 4 (V4) | 3 ml of distilled water |
| Dilution Flask | 15 ml of distilled water |
| Cartridge 1 (C1) | tC18 6 cc 1 g sep pack |
| HPLC Column | Luna C18(2), 250 × 10 mm, 5 μm, Phenomenex |
| HPLC Solvent | 35% acetonitrile in an aqueous 0.1% trifluoroacetitic acid solution |
| HPLC flow | 4.6 ml/min |

Example 16: Pharmacokinetics of [$^{19}$F]-E01 Anti-PD-L1 Adnectin

The following experiment was conducted to compare the pharmacokinetics of $^{19}$F labelled-E01 anti-PD-L1 adnectin and E01-4PEG-DBCO (unlabeled anti-PD-L1-adnectin-DBCO precursor) in cynomolgus monkeys (n=3). This was a cross-over design study with a 2-week washout between doses. Serum samples were collected and analyzed by either a LBA using specific adnectin-binding reagents that do not differentiate E01-4PEG-DBCO from [$^{19}$F]-E01, or LC/MS assays that differentiate between E01-4PEG-DBCO and [$^{19}$F]-E01.

A summary of the PK parameters is shown in Table 3.

TABLE 3

| | [$^{19}$F]-E01 | E01-4PEG-DBCO |
|---|---|---|
| AUC(INF) (μg*h/mL) | 4.72 ± 0.79 | 2.92 ± 0.40 |
| CLTs (mL/min/kg) | 4.54 ± 0.81 | 5.78 ± 0.76 |
| Vss (L/kg) | 0.29 ± 0.05 | 0.40 ± 0.04 |
| T-HALF (h) | 1.69 ± 0.13 | 1.65 ± 0.13 |
| MRT (h) | 1.05 ± 0.06 | 1.14 ± 0.05 |

Following an i.v. dose to cynomolgus monkeys, the CLTs of [$^{19}$F]-E01 was low in both studies. The T-HALF was also short, at about 1.7 hours. The PK of E01-4PEG-DBCO was similar to that of [$^{19}$F]-E01. The PK parameters were also similar by LC/MS.

EQUIVALENTS

Those skilled in the art will recognize, or be able to ascertain using no more than routine experimentation, many equivalents of the specific embodiments described herein. Such equivalents are intended to be encompassed by the following claims.

---

What is claimed is:

1. A method of visualizing a target molecule in a subject, comprising a. administering to the subject an imaging agent that binds specifically to the target molecule at a dose of about 3-10 mCi (100-333 MBq); and b. conducting a PET scan of the subject about 30-120 minutes after step (a), wherein the imaging agent comprises (i) an $^{18}$F-radiolabeled prosthetic group comprising the structure

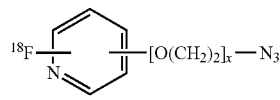

or a pharmaceutically acceptable salt thereof, wherein x is an integer from 1 to 8 the $^{18}$F-radiolabel is attached ortho to the N atom of the pyridine; and (ii) a protein linked to the $^{18}$F-radiolabeled prosthetic group by a bifunctional conjugating (BFC) moiety, wherein the protein is an antibody, an antigen binding fragment of an antibody, or a fibronectin type III (Fn3) domain.

2. The method of claim 1, wherein the subject has at least one tumor.

3. The method of claim 2, comprising determining the level of the target molecule in the at least one tumor of the subject.

4. The method of claim 3, wherein the level of target molecule in the at least one tumor is indicative of whether a subject is likely to respond to a treatment with an immuno-oncology agent.

5. The method of claim 4, wherein the target molecule is human PD-L1, and the immune-oncology agent is a PD-1 or PD-L1 antagonist.

6. The method of claim 5, wherein the PD-1 antagonist is an anti-PD-1 antibody.

7. The method of claim 1, wherein the $^{18}$F-radiolabeled prosthetic group comprises the structure

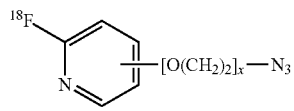

or a pharmaceutically acceptable salt thereof.

8. The method of claim 1, wherein the $^{18}$F-radiolabeled prosthetic group comprises the structure

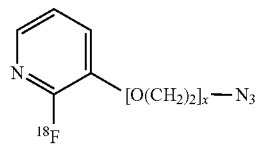

or a pharmaceutically acceptable salt thereof.

9. The method of claim 1, wherein the $^{18}$F-radiolabeled prosthetic group comprises the structure

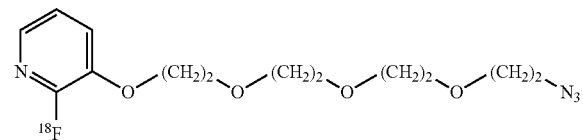

or a pharmaceutically acceptable salt thereof.

10. The method of claim 1, wherein the $^{18}$F-radiolabeled prosthetic group is linked to a fibronectin type III (Fn3) domain.

11. The method of claim 10, wherein $^{18}$F-radiolabeled prosthetic group comprises the following structure,

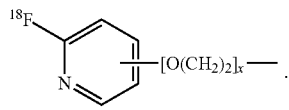

12. The method of claim 10, wherein $^{18}$F-radiolabeled prosthetic group comprises the following structure,

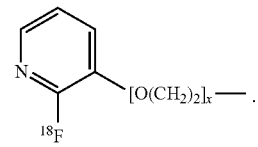

13. The method of claim 10, wherein the $^{18}$F-radiolabeled prosthetic group has the structure

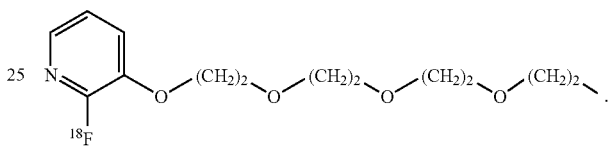

14. The method of claim 10, wherein the imaging agent has the following structure,

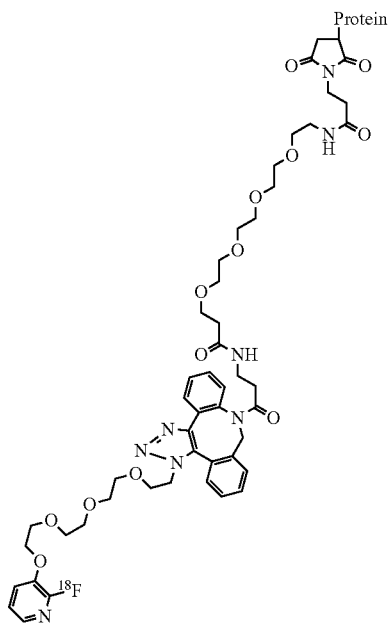

wherein the maleimide group of the BFC is covalently linked to the thiol group on a cysteine residue of the protein.

15. The method of claim 14, wherein the cysteine residue is at the C-terminus of the protein.

16. The method of claim 1, wherein the target molecule is associated with a disease.

17. The method of claim 1, wherein the Fn3 domain is a human $^{10}$Fn3 domain.

18. The method of claim 1, wherein the BFC comprises a cyclooctyne selected from the group consisting of a dibenzocyclooctyne, a biarylazacyclooctynone and a dimethoxyazacyclooctyne.

19. The method of claim 18, wherein the BFC is DBCO-PEG4-NHS-Ester, DBCO-Sulfo-NHS-Ester, DBCO-PEG4-Acid, DBCO-PEG4-Amine or DBCO-PEG4-Maleimide.

20. A method of visualizing a target molecule in a subject, comprising
 a. administering to the subject an imaging agent that binds specifically to the target molecule at a dose of about 3-10 mCi (100-333 MBq); and
 b. conducting a PET scan of the subject about 30-120 minutes after step (a), wherein the imaging agent comprises
   (i) an $^{18}$F-radiolabeled prosthetic group having the structure

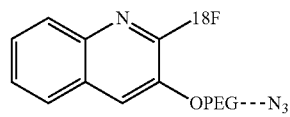

wherein "OPEG" is $[O(CH_2)_2]_x$, and x is an integer from 1 to 8, or a pharmaceutically acceptable salt thereof, and
   (ii) a protein linked to the $^{18}$F-radiolabeled prosthetic group by a bifunctional conjugating (BFC) moiety, wherein the protein is an antibody, an antigen binding fragment of an antibody, or a fibronectin type III (Fn3) domain.

21. The method of claim 20, wherein the $^{18}$F-radiolabeled prosthetic group is linked to a fibronectin type III (Fn3).

* * * * *